United States Patent [19]

Johnson

[11] 4,351,833
[45] Sep. 28, 1982

[54] 9-AMINO-1-HYDROXYOCTAHYDROBEN-ZO[C]QUINOLINES AND DERIVATIVES THEREOF AS ANALGESICS AND ANTI-EMETICS

[75] Inventor: Michael R. Johnson, Gales Ferry, Conn.

[73] Assignee: Pfizer Inc., New York, N.Y.

[21] Appl. No.: 296,745

[22] Filed: Aug. 27, 1981

Related U.S. Application Data

[62] Division of Ser. No. 173,207, Jul. 28, 1980, Pat. No. 4,309,545.

[51] Int. Cl.$^3$ ............................................. C07D 221/12
[52] U.S. Cl. .............................. 424/248.5; 424/248.54; 424/248.55; 424/250; 424/258; 544/126; 544/361; 546/108
[58] Field of Search ................ 546/108; 544/126, 361; 424/250, 263, 248.5, 248.54, 248.55, 258

[56] References Cited

U.S. PATENT DOCUMENTS

| 3,878,219 | 4/1975 | Lee | 424/263 X |
| 3,928,598 | 12/1975 | Archer | 260/345.3 X |
| 4,087,545 | 5/1978 | Archer et al. | 424/283 |
| 4,152,450 | 5/1979 | Day et al. | 424/283 |

FOREIGN PATENT DOCUMENTS 854655  5/1976  Belgium .

OTHER PUBLICATIONS

Hardman et al., *Proc. West. Pharmacol. Soc.*, 14, 14–20, (1971).
Mechoulam and Edery in "Marijuana", edited by Mechoulam, Academic Press, New York, 1973, p. 127.
Paton, in *Ann. Rev. Pharmacol.*, 15, 192, (1975).
Beil, in "Psychotomimetic Drugs", Efron, Ed., Raven Press, New York, 1970, p. 336.
Sallan et al., *New England J. Med.*, 293, 795, (1975).
Borison et al., *New England J. Med.*, 298, 1480, (1978).

*Primary Examiner*—Richard A. Schwartz
*Attorney, Agent, or Firm*—Charles J. Knuth; Paul D. Thomas; Allen Bloom

[57] ABSTRACT

9-Amino-1-hydroxyoctahydrobenzo[c]quinoline derivatives of formula

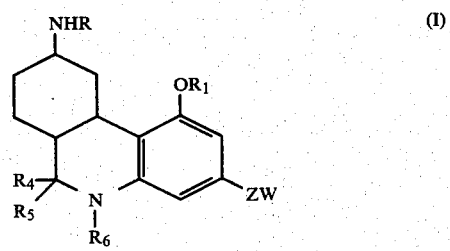

and pharmaceutically acceptable acid addition salts thereof wherein R is hydrogen, $COR_7$ or $SO_2R_8$ where $R_7$ is hydrogen, alkyl, having from one to five carbon atoms; alkenyl and alkynyl each having from two to six carbon atoms; trifluoromethyl, benzyl, furyl, thienyl, pyridyl or $R_9C_6H_4$ where $R_9$ is H, $NH_2$, F, Cl, Br, $CH_3$ or $OCH_3$; $R_8$ is alkyl having from one to five carbon atoms or $R_9C_6H_4$; $R_1$ is hydrogen, benzyl, benzoyl, alkanoyl having from one to five carbon atoms or $-CO-(CH_2)_p-NR_2R_3$ wherein p is 0 or an integer from 1 to 4; each of $R_2$ and $R_3$ when taken individually is hydrogen or alkyl having from one to four carbon atoms; $R_2$ and $R_3$ when taken together with the nitrogen to which they are attached form a 5- or 6-membered heterocyclic ring selected from piperidino, pyrrolo, pyrrolidino, morpholino or N-alkylpiperazino having from one to four carbon atoms in the alkyl group;
$R_4$ is hydrogen, alkyl having from 1 to 6 carbon atoms or $-(CH_2)_z-C_6H_5$ wherein z is an integer from 1 to 4;
$R_5$ is hydrogen, methyl or ethyl;
$R_6$ is hydrogen, $-(CH_2)_y$-carbalkoxy having from one to four carbon atoms in the alkoxy group and wherein y is 0 or an integer from 1 to 4, carbobenzyloxy, formyl, alkanoyl having from two to five carbon atoms, alkyl having from one to six carbon atoms; $-(CH_2)_x-C_6H_5$ wherein x is an integer from 1 to 4; or $-CO(CH_2)_{x-1}-C_6H_5$;
Z is (a) alkylene having from one to nine carbon atoms; (b) $-(alk_1)_m-X-(alk_2)_n-$ wherein each of $(alk_1)$ and $(alk_2)$ is alkylene having from one to nine carbon atoms, with the proviso that the summation of carbon atoms in $(alk_1)$ plus $(alk_2)$ is not greater than nine; each of m and n is 0 or 1; X is O, S, SO and $SO_2$; and W is hydrogen, methyl, pyridyl, piperidyl,

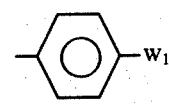

wherein $W_1$ is selected from the group consisting of hydrogen, fluoro and chloro; and

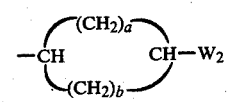

wherein $W_2$ is hydrogen or

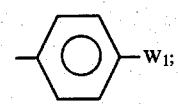

a is an integer from 1 to 5 and b is 0 or an integer from 1 to 5; with the proviso that the sum of a and b is not greater than 5; useful in mammals as analgesics, tranquilizers, anti-emetic agents, diuretics, anticonvulsants, antidiarrheals, antitussives, in treatment of glaucoma, and intermediates therefore.

26 Claims, No Drawings

9-AMINO-1-HYDROXYOCTAHYDROBENZO[C]QUINOLINES AND DERIVATIVES THEREOF AS ANALGESICS AND ANTI-EMETICS

CROSS-REFERENCE TO RELATED APPLICATION

This is a division of application Ser. No. 173,207 filed July 28, 1980, now U.S. Pat. No. 4,309,545.

BACKGROUND OF THE INVENTION

This invention relates to certain novel benzo[c]quinolines and more particularly to certain 9-amino-1-hydroxyoctahydrobenzo[c]quinolines and derivatives thereof, especially certain amide derivatives of the 9-amino group, and pharmaceutically acceptable acid addition salts thereof useful as CNS agents, especially as analgesics and antiemetic agents for use in mammals, including man; methods for their use and pharmaceutical compositions containing them.

An acceptable alternative nomenclature for the herein described compounds of formula (I) is based upon replacement of the root "benzo[c]quinoline" with "phenanthridine." Thus, dl-trans-5,6,6a,7,8,9,10,10a-octahydro-1-acetoxy-9beta-acetamido-6-beta-methyl-3-(5-phenyl-2-pentyloxy)benzo[c]quinoline becomes dl-trans-5,6,6a,7,8,9,10,10a-octahydro-1-acetoxy-9beta-acetamido-6beta-methyl-3-(5-phenyl-2-pentyloxy)-phenanthridine.

Despite the current availability of a number of analgesic agents, the search for new and improved agents continues, thus pointing to the lack of an agent useful for the control of broad levels of pain and accompanied by a minimum of side-effects. The most commonly used agent, aspirin, is of no practical value for the control of severe pain and is known to exhibit various undesirable side-effects. Other, more potent analgesics such as d-propoxyphene, codeine, and morphine, possess addictive liability. The need for improved and potent analgesics is, therefore, evident.

Belgian Patent No. 854,655, granted Nov. 16, 1977, describes compounds of the formulae

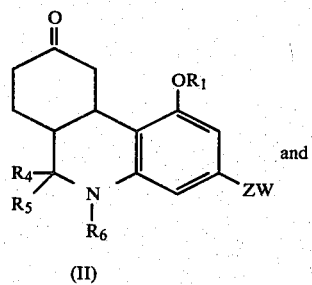

(II)

and

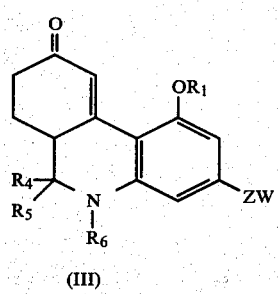

(III)

and the corresponding 9-hydroxy compounds wherein $R_1$, $R_4$, $R_5$, $R_6$, Z and W are as defined herein. The ketones of formula (II) and the corresponding 9-hydroxy compounds are stated to be useful as CNS agents, especially as analgesics and tranquilizers, as hypotensives, diuretics and as agents for treatment of glaucoma. Copending U.S. application Ser. No. 52,324, filed June 26, 1979, discloses compounds of formula (II) and corresponding 1,9 dihydroxy-octahydrobenzo[c]quinolines as antiemetic agents.

The analgesic properties of 9-nor-9beta-hydroxyhexahydrocannabinol and of other cannabinoid structures, such as delta-8-tetrahydrocannabinol (delta-8-THC) and its primary metabolite, 11-hydroxy-delta-8-THC, have been reported by Wilson and May, *Absts. Papers, Am. Chem. Soc.*, 168 Meet., MEDI 11 (1974), *J. Med. Chem.* 17, 475–476 (1974), and *J. Med. Chem.*, 18, 700–703 (1975).

A series of structurally related dibenzo[b,d]pyrans, having at the 9-position substituents such as alkyl, hydroxy and oxo, are disclosed in U.S. Pat. Nos. 3,507,885; 3,636,058; 3,649,650; 3,856,821; 3,928,598; 3,944,673, 3,953,603 and 4,143,139. Particularly of interest is dl-trans-1-hydroxy-3-(1,1-dimethylheptyl)-6,6-dimethyl-6,6a,7,8,10,10a-hexahydro-9H-dibenzo[b,d]pyran-9-one, an antiemetic, antianxiety agent with analgesic properties in animals, now generally referred to as nabilone.

U.S. Pat. No. 4,152,450 discloses certain 3-alkyl-1-hydroxytetrahydro and hexahydrodibenzo[b,d]pyrans, having an amino or amido group at the 9-position, which are useful as analgesics, antidepressants, antianxiety agents and hypotensive agents.

U.S. Pat. No. 3,878,219 discloses 5H-[1]benzopyrano[3,4-d]pyridines useful as analgesics and U.S. Pat. No. 3,888,946 discloses a corresponding class of compounds in which the C-ring is five membered rather than six membered.

Bergel et al., *J. Chem. Soc.*, 286 (1943) investigated the replacement of the pentyl group at the 3-position of 7,8,9,10-tetrahydro-3-pentyl-6,6,9-trimethyl-6H-dibenzo[b,d]pyran-1-ol by alkoxy groups of four to eight carbon atoms and found that these compounds had little or no hashish activity at 10 to 20 mg/kg.

In a more recent study, Loev et al., *J. Med. Chem.*, 16, 1200–1206 (1973) report a comparison of 7,8,9,10-tetrahydro-3-substituted-6,6,9-trimethyl-6H-dibenzo[b,d]-pyran-1-ols in which the 3-substituent is —OCH(CH$_3$)C$_5$H$_{11}$; —CH$_2$CH(CH$_3$)C$_5$H$_{11}$; or —CH(CH$_3$)C$_5$H$_{11}$. The ether side chain containing compound was 50% less active in central nervous system activity than the corresponding compound in which the alkyl side chain is directly attached to the aromatic ring, rather than through an intervening oxygen atom; and 5 times as active as the compound in which oxygen is replaced by methylene.

Hoops et al., *J. Org. Chem.*, 33, 2995–2996 (1968) describe the preparation of the 5-aza analog of delta-6a(10a)-tetrahydrocannabinol referred to therein as 7,8,9,10-tetrahydro-1-hydroxy-5,6,6,9-tetramethyl-3-n-pentylphenanthridine, but report no utility for the compound. Beil, in "Psychomimetic Drugs", edited by Efron, Raven Press, New York, 1970, page 336, reports the compound was "completely inert in animal pharmacology."

Hardman et al., *Proc. West. Pharmacol. Soc.*, 14, 14–20 (1971) reports some pharmacological activity for 7,8,9,10-tetrahydro-1-hydroxy-6,6,9-trimethyl-3-n-pentyl phenanthridine, a 5-aza-delta-6a(10)a-tetrahydrocannabinol.

Mechoulam and Edery in "Marijuana", edited by Mechoulam, Academic Press, New York, 1973, page 127, observe that major structural changes in the tetrahydrocannabinol molecule seem to result in steep reductions in analgesic activity.

Paton, in *Annual Review of Pharmacology*, 15, 192 (1975) presents generalizations on structure-action relationships among cannabinoids. The presence of the gem dimethyl group in the pyran ring is critical for cannabinoid activity and substitution of N for O in the pyran ring removes activity.

U.S. Pat. No. 4,087,545 discloses the antiemetic and antinausea properties of 1-hydroxy-3-alkyl-6,6a,7,8,10,-10a-hexahydro-9H-dibenzo[b,d]pyran-9-ones.

Sallan et al., *N. E. J. Med.* 293, 795 (1975) reported oral delta-9-tetrahydrocannabinol has antiemetic properties in patients receiving cancer chemotherapy.

Delta-9-tetrahydrocannibinol is reported by Shannon et al. (Life Sciences 23, 49–54, 1978) to lack antiemetic effects in apomorphine-induced emesis in the dog. Borison et al., *N. England J. of Med.* 298, 1480 (1978) report the use of unanesthetized cats as an animal model for determining the antiemetic effect of compounds especially in connection with emesis induced by cancer chemotherapy drugs. They found that pretreatment of unanesthetized cats with 1-hydroxy-3-(1',1'-dimethylheptyl)-6,6-dimethyl-6,6a,7,8,10,10a-hexahydro-9H-dibenzo[b,d]pyran-9(8H)-one (nabilone) affords pronounced protection against vomiting per se after injection of antineoplastic drugs.

SUMMARY OF THE INVENTION

It has now been found that certain benzo[c]quinolines, namely, 9-amino-1-hydroxyoctahydro-6H-benzo[c]quinolines and certain amides thereof of formula (I) are effective CNS agents, useful in mammals as tranquilizers, anticonvulsants, diuretics, antidiarrheals, antitussives and agents for treatment of glaucoma; they are particularly effective in mammals, including man, as analgesics and as agents for treatment and prevention of emesis and nausea, especially that induced by antineoplastic drugs. Said invention compounds, which are non-narcotic and free of addiction liability, have the formula

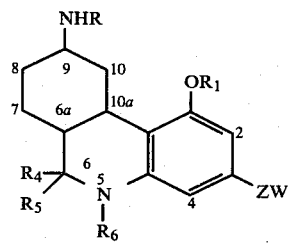

(I)

and pharmaceutically acceptable acid addition salts thereof wherein R is hydrogen, $COR_7$ or $SO_2R_8$ where $R_7$ is a member selected from the group consisting of hydrogen, alkyl, having from one to five carbon atoms; alkenyl and alkynyl each having from two to six carbon atoms, trifluoromethyl, benzyl, furyl, thienyl, pyridyl and $R_9C_6H_4$ where $R_9$ is a member selected from the group consisting of H, $NH_2$, F, Cl, Br, $CH_3$ and $OCH_3$; $R_8$ is alkyl having from one to five carbon atoms or $R_9C_6H_4$;

$R_1$ is selected from the group consisting of hydrogen, benzyl, benzoyl, alkanoyl having from one to five carbon atoms and $—CO—(CH_2)_p—NR_2R_3$ wherein p is 0 or an integer from 1 to 4; each of $R_2$ and $R_3$ when taken individually is selected from the group consisting of hydrogen and alkyl having from one to four carbon atoms; $R_2$ and $R_3$ when taken together with the nitrogen to which they are attached form a 5- or 6-membered heterocyclic ring selected from the group consisting of piperidino, pyrrolo, pyrrolidino, morpholino and N-alkylpiperazino having from one to four carbon atoms in the alkyl group;

$R_4$ is selected from the group consisting of hydrogen, alkyl having from 1 to 6 carbon atoms and $—(CH_2)_z—C_6H_5$ wherein z is an integer from 1 to 4;

$R_5$ is selected from the group consisting of hydrogen, methyl and ethyl;

$R_6$ is selected from the group consisting of hydrogen, $—(CH_2)_y$-carbalkoxy having from one to four carbon atoms in the alkoxy group and wherein y is 0 or an integer from 1 to 4, carbobenzyloxy, formyl, alkanoyl having from two to five carbon atoms, alkyl having from one to six carbon atoms; $—(CH_2)_x—C_6H_5$ wherein x is an integer from 1 to 4; and $—CO(CH_2)_{x-1}—C_6H_5$;

Z is selected from the group consisting of
 (a) alkylene having from one to nine carbon atoms;
 (b) $—(alk_1)_m—X—(alk_2)_n—$ wherein each of $(alk_1)$ and $(alk_2)$ is alkylene having from one to nine carbon atoms, with the proviso that the summation of carbon atoms in $(alk_1)$ plus $(alk_2)$ is not greater than nine; each of m and n is 0 or 1; X is selected from the group consisting of O, S, SO and $SO_2$; and W is selected from the group consisting of hydrogen, methyl, pyridyl, piperidyl,

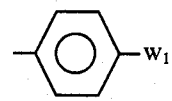

wherein $W_1$ is selected from the group consisting of hydrogen, fluoro and chloro; and

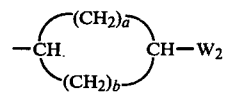

wherein $W_2$ is selected from the group consisting of hydrogen and

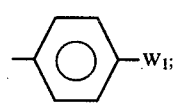

a is an integer from 1 to 5 and b is 0 or an integer from 1 to 5; with the proviso that the sum of a and b is not greater than 5.

Also included in this invention are pharmaceutically acceptable acid addition salts of the compound of formula I. Representative of such salts are mineral acid salts such as the hydrochloride, hydrobromide, sulfate, nitrate, phosphate; organic acid salts such as the citrate, acetate, sulfosalicylate, tartrate, glycolate, malonate, maleate, fumarate, malate, 2-hydroxy-3-naphthoate, pamoate, salicylate, stearate, phthalate, succinate, gluconate, mandelate, lactate and methane sulfonate.

Compounds having the formula I above, contain asymmetric centers at the 9, 6a- and 10a-positions. There may be additional asymmetric centers in the 3-position substituent (-Z-W), the 5-position substituent ($R_6$), the 6-position, and in the 6-position substituents. Diaster-eoisomers with the 9beta-configuration are generally favored over the 9alpha-isomers because of greater (quantitatively) biological activity. For the same reason, the trans(6a,10a)diastereomers of compounds of formula I are generally favored over the cis(6a,10a)-diastereomers. Among the enantiomers of a given compound, one will generally be favored over the other and the racemate because of its greater activity. The enantiomer favored is determined by the procedures described herein. For example, the d-enantiomer of 5,6,6a-beta,7,8,9,10,10a-alpha-octahydro-1-acetoxy-9betaamino-5,6beta-dimethyl-3-(5-phenyl-2-pentyloxy)-benzo[c]quinoline is favored over the 1-enantiomer and the racemate because of its greater analgesic activity.

Among the 3-position (ZW) diastereoisomers, one will generally be favored over the other. For example, compounds of formula (I) wherein ZW is

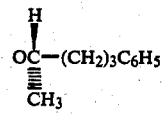

are favored over the corresponding compounds wherein ZW is

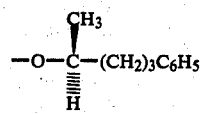

because of their greater analgesic activity. For convenience, the above formula is considered to be generic to and embracive of the racemic modifications of the compounds of this invention, the diastereomeric mixtures, the pure enantiomers and diastereomers thereof. The utility of the racemic mixtures, the diastereomeric mixtures as well as of the pure enantiomers and diastereomers is determined by the biological evaluations described below.

Especially preferred compounds of formula (I) are those wherein R is hydrogen, $COR_7$ or $SO_2R_8$ where $R_7$ is alkyl having from one to five carbon atoms or $CF_3$; $R_8$ is as defined above; $R_1$ is hydrogen or alkanoyl having from one to five carbon atoms; $R_6$ is hydrogen or methyl and each of $R_4$ and $R_6$ are hydrogen or alkyl having from one to six carbon atoms; Z is alkylene or $-(alk_1)_m-X-(alk_2)_n-$ and W is hydrogen or phenyl. A preferred value for X is O.

When Z is $-(alk_1)_m-X-(alk_2)_n-$, a preferred value is $-O-(alk_2)_n-$, and particularly preferred values for ZW are $-OCH(CH_3)(CH_2)_4CH_3$ or $-OCH(CH_3)(CH_2)_3C_6H_5$. When Z is alkylene, preferred values for ZW are $-C(CH_3)_2(CH_2)_5CH_3$ or $-CH(CH_3)(CH_2)_3C_6H_5$.

Particularly preferred are those compounds of formula (I) wherein:
R is $CH_3CO$, $CF_3CO$ or $CH_3SO_2$;
$R_1$ is $CH_3CO$;
$R_4$ is methyl;
$R_5$ is hydrogen;
$R_6$ is hydrogen or methyl;

Z is

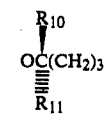

where one of $R_{10}$ and $R_{11}$ is hydrogen and the other is methyl, and

W is phenyl. Most particularly preferred of these is the single enantiomer of absolute configuration [3(1R), 6S, 6aR, 9R, 10aR] of formula (I) wherein R and $R_1$ are $CH_3CO$, $R_4$ is methyl, $R_5$ is hydrogen, $R_6$ is methyl, $R_{10}$ is hydrogen and $R_{11}$ is methyl.

As mentioned above, the compounds of the invention are particularly useful as analgesics, and as antiemetic and antinausea agents for use in mammals, including man. The invention further provides a method for producing analgesia in mammals and a method for prevention and treatment of nausea in a mammal subject to nausea, in each case by oral or parenteral administration of an effective amount of a compound of formula (I) or its pharmaceutically acceptable salt.

Also provided are pharmaceutical compositions for use as analgesics, as well as those suitable for use in prevention and treatment of nausea, comprising an effective amount of compound of the invention and a pharmaceutically acceptable carrier.

The compounds of formula (I) wherein R is hydrogen are also useful as intermediates for preparation of the corresponding compounds wherein R is $COR_7$ or $SO_2R_8$ where $R_7$ and $R_8$ are as defined above.

Further, the invention provides 6 beta-$R_4$-substituted oximes of the formula

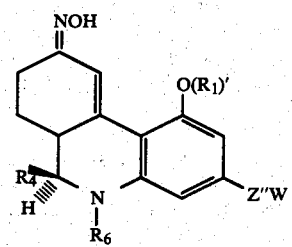

(IV A)

wherein $(R_1)'$ is hydrogen, benzyl, benzoyl or alkanoyl having from one to five carbon atoms; Z" is the same as Z as defined above except that X is limited to oxygen and $R_4$, $R_6$, and W are as previously defined; useful as intermediates in providing compounds of formula (I) having a beta-$R_4$ substituent, a beta-NHR substituent and a trans (6a, 10a) ring structure.

DETAILED DESCRIPTION OF THE INVENTION

The compounds of formula (I) are generally prepared from the corresponding 9-oxo compounds of formula (II) by reductive amination techniques to provide a-9-amino compound (I,R=H) which is further reacted to provide the desired amide as shown below

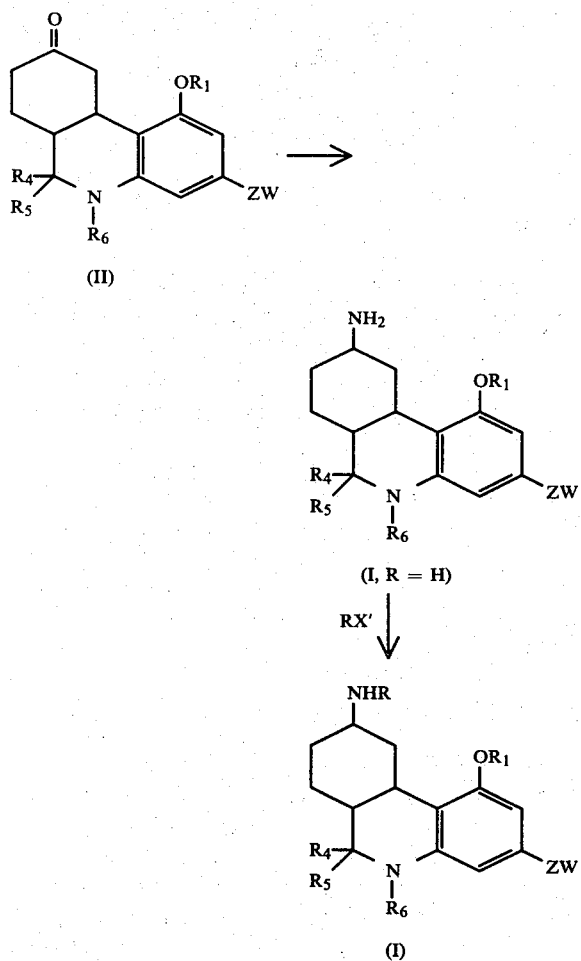

The reagents of formula RX' are common reagents known in the art for converting amines to amides. Preferred RX' are $R_7COR^a$, $(R_7CO)_2O$ and $R_8SO_2R^b$ where $R^a$ is OH, alkoxy having from one to four carbon atoms, Cl or Br; $R^b$ is OH, Cl or Br and $R_7$ and $R_8$ are as defined above.

The conversion of the 9-oxo compounds (II) to the corresponding 9-amino compounds of formula (I, R=H) may be carried out by any of the known reductive amination methods for converting ketones to primary amines. See, for example, "Organic Reactions", 4, 174 (1948); ibid, 5, 301 (1949); Migrdichian, "Organic Synthesis" Reinhold Publ. Co., New York, 1957, Vol. 1, p. 472; and Borch et al., *J. Am. Chem. Soc.,* 93, 2897 (1971). The reaction is carried out in the presence of ammonia or an acid addition salt thereof, and a reducing agent. Preferred reducing agents include hydrogen in the presence of a noble metal catalyst such as, e.g. nickel, palladium, platinum, rhodium or ruthenium; metal hydride reducing agents, for example, sodium cyanoborohydride, sodium borohydride or lithium borohydride; and formic acid. An especially preferred reducing agent is hydrogen in the presence of palladium for reasons of efficiency and economy.

In a typical reaction, e.g., a sulfur-free starting 9-ketone of formula (II), especially those wherein the 1-hydroxy group is protected as an ester or benzyl ether, is reacted with a molar excess of hydrogen and ammonium chloride in the presence of 5% palladium-on-carbon catalyst in an amount equal to about ½ to 2 times the weight of ketone (II) and in the presence of a reaction inert organic solvent, e.g., methanol. The reaction is carried out at atmospheric pressure and ambient temperature until the reaction is substantially complete, ordinarily within from about 8–48 hours. The desired amine is recovered by standard methods, well known in the art.

The product obtained in this manner is a mixture of 9 alpha-amino and 9 beta-amino isomers of formula (I,R=H) which correspond to the starting 9-oxo compound (II) in other structural features except, as will be recognized by one skilled in the art, for those cases wherein the values of $R_1$, $R_4$, $R_6$ and ZW in the compound (II) include one or more benzyl or carbobenzyloxy groups in which said groups are subject to cleavage when the reducing agent employed is hydrogen and a noble metal catalyst. While this mixtiure of 9-amino isomers may be separated prior to introduction of the amido residue R to form the compound of formula (I), it is usually preferred to react the mixture of diastereomers, (I,R=H) with RX' as defined above, to provide the corresponding mixture of diastereomeric amides of formula (I) and to separate the latter mixture.

The separation of 9 alpha-amino and 9 beta-amino diastereomers of formula (I) is brought about by any of the methods known in art for affecting such separations, for example by fractional crystallization or chromatographic techniques. When the latter method is employed, it is preferred to employ column chromatography on silica gel, eluting with solvents such as, for example, ethyl ether, isopropyl ether, tetrahydrofuran, benzene, toluene, cyclohexane, ethyl acetate, methylene chloride, chloroform or mixtures thereof.

The reaction of 9 alpha-amino, 9 beta-amino compounds (I,R=H) or their mixtures to provide the corresponding amides of formula (I) is carried out by a variety of well known methods. For example, in one such method, esters of formula $R_7COR^a$, where $R^a$ is alkoxy having from one to four carbon atoms and $R_7$ is as previously defined, are employed. The amine (I,R=H) is contacted with at least an equimolar amount of ester $R_7COR^a$, preferably a large molar excess, e.g. a solvent amount. The reaction may also employ a base such as alkali metal alkoxide of formula $MOR^a$, where M is sodium or potassium, or a metal hydride such as, e.g. sodium hydride, calcium hydride or potassium hydride.

The compounds of formula (I) wherein R is $R_7CO$ where $R_7$ is other than hydrogen are preferably prepared by acylation of the corresponding amine (I,R=H) with an acid halide of formula $R_7COR^a$ where $R^a$ is Cl or Br; or an acid anhydride, $(R_7CO)_2O$ by methods known in the art. For example in a typical acylation, the 9-amino compound is contacted with at least an equivalent amount, preferably a molar excess, of the appropriate acid halide or acid anhydride in the presence of a reaction inert organic solvent and preferably in the presence of an equivalent amount of an acid acceptor. The reaction can be carried out successfully over a wide range of temperatures; however, temperatures in the range of about −30° to 50° C. and especially −20° to 30° C. are preferred. Examples of reaction inert solvents which are suitable for this reaction are methylene chloride, chloroform, 1,2-dichloroethane, ethyl ether, tetrahydrofuran, dioxan, benzene, toluene, hexane and the like. Examples of suitable acid acceptors which may be employed are tertiary amines such as triethylamine, pyridine, 4-dimethylaminopyridine, N,N- dimethylaniline, N-methylmorpholine and N-ethylpiperidine; and inorganic bases such as sodium hydroxide, potassium carbonate, calcium carbonate, potassium acetate and sodium bicarbonate.

The product is isolated by well known methods such as partitioning between water and water immiscible solvent, suitable washing of the organic phase and evaporation of solvent. The product obtained is often of suitable purity, but is further purified, if desired, by standard means, e.g. crystallization or column chromatography. The latter two methods, alone or in combination, may also be employed to separate mixtures of diastereomers of the desired products.

The sulfonamides of the invention of formula (I) wherein R is $R_8SO_2$ are similarly prepared from the appropriate acid or acid halide of formula $R_8SO_2R^b$, where $R_8$ and $R^b$ are as previously defined. The preferred reagents are the acid halides of the latter formula wherein $R^b$ is Cl or Br. The sulfonylation with the preferred acid halides and 9-amino compound (I,R=H) is carried out and the product isolated as described above for acyl halides and anhydrides.

A preferred method for providing the 9-amino precursors of the amides of formula (I) for those cases where either the 3-substituent (ZW) is a sulfur containing moiety or the starting material of formula (II) contains a desired group susceptible to catalytic reduction, such as a benzyl or benzyloxycarbonyl group, employs the use of sodium cyanoborohydride in the presence of ammonia or an ammonium salt for reductive amination of the 9-oxo compound (II). Generally, equimolar amounts of the starting material of formula (II) and sodium cyanoborohydride are contacted in the presence of molar excess of an ammonium salt, e.g. ammonium acetate or ammonium chloride in reaction inert solvent, e.g. methanol, ethanol or tetrahydrofuran and the resulting mixture is maintained at the reflux temperature of the solvent until the reaction is substantially completed.

An alternate preferred method for reductive amination of sulfur containing starting materials (II), or those containing a benzyl or benzyloxocarbonyl group which one wants to be retained in the product of formula (I), employs formic acid in the presence of ammonium formate or formamide, the well known Leukart reaction. See, e.g. *Organic Reactions* 5, 301 (1949). Typically, the starting ketone (II) is heated in the presence of an excess of formic acid and formamide at the reflux temperature of the mixture while removing the water formed in the reaction until the reaction is substantially completed. The mixture is then cooled and isolated by methods well known in the art.

Another preferred procedure for producing compounds of formula (I) wherein $R_5$ is hydrogen comprises reaction of an enone of formula (III, $R_5$=H) with hydroxylamine, reduction of the intermediate oxime (IV) and subsequent acylation or sulfonylation as outlined below.

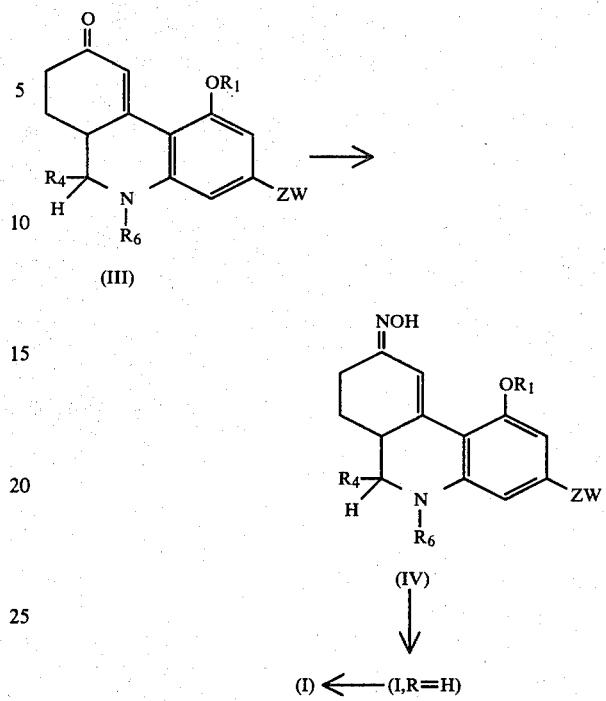

An especially preferred modification of the above procedure is employed to provide compounds of formula (I) wherein Z is alkylene or —(alk$_1$)$_m$—O—(alk$_2$)$_n$— as defined above, having a beta-$R_4$ substituent, a beta-NHR substituent and a trans(6a,10a) ring structure with a high degree of stereoselectivity. It comprises reducing the corresponding formula (III) compound wherein $R_4$ is a beta-substituent and $R_5$ is hydrogen in alcoholic solvent, e.g. methanol or ethanol, with from about ½ to 2 parts by weight of palladium-on-carbon in a hydrogen atmosphere to provide the intermediate 6a,10a-trans-9-beta-amino compound (IA,R=H) and conversion to amide (IA) by acylation or sulfonylation as described above.

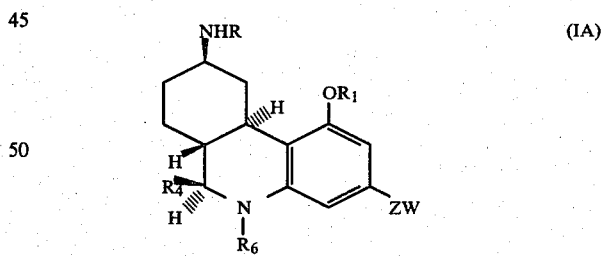

In a typical embodiment of the preferred modification of this process, the appropriate compound of formula (III) dissolved in dry pyridine is contacted with an equimolar amount of hydroxylamine or an acid addition salt thereof such as hydroxylamine hydrochloride. The mixture is stirred at or about room temperature until the formation of oxime is substantially completed. The oxime (IV) is then isolated by standard methods and taken up in an alcoholic solvent, e.g. methanol or ethanol, and hydrogenated in the presence of about an ½ to twice its weight of Pd/C catalyst. The hydrogenation is preferably carried out at room temperature and at pressures ranging from atmospheric pressure up to 50 psi (3.5 kg/cm²) for reasons of economy and efficiency. The catalyst is then removed and the filtrate evaporated to provide the corresponding 9-beta-amino compound (IA,R=H). This is then reacted with the appropriate reagent RX' to provide the desired compound of formula (IA) as described above for compounds of formula (I).

The starting materials of formulae (II) and (III) are prepared according to procedures described in Belgian Patent No. 854,655. A suitable process begins with appropriately substituted anilines, e.g. 3-hydroxy-5-(Z-W-substituted)anilines, (V) or derivatives thereof in which the 3-hydroxy group is protected by a group ($Y_1$) easily removable to regenerate the hydroxy group; e.g. methyl, ethyl, benzyl, substituted benzyl wherein the substituent is, for example, alkyl having from 1 to 4 carbon atoms, halo (Cl, Br, F, I), and alkoxy having from one to four carbon atoms. When Z is —(alk$_1$)$_m$—X—(alk$_2$)$_n$—, $Y_1$ is preferably benzyl or a substituted benzyl group since it can subsequently be removed without detriment to the Z group.

The protected aniline derivative (V) is then converted to a compound of formula (VI) by known technology as described below.

An abbreviated reaction sequence (Flow Sheet A) for preparing representative compounds of formula VIIIA-C beginning with a 3-(protected hydroxy)-5-(Z-W-substituted)aniline (V) wherein —Z—W is OCH$_3$ is given below.

The 5-substituent of formula (V) compounds can be group —Z—W desired in compounds of formulae (II) or (III), or a group readily convertible to said group. When the Z moiety of group —Z—W is —(alk$_1$)$_m$—X—(alk$_2$)$_n$— wherein X is 0 or S and each of m and n is 0, the 5-substituent, when W is hydrogen, is —XH (i.e., OH or SH) or a protected —XH group of the formula —X—$Y_1$ wherein $Y_1$ is as defined above. When, of course, —Z—W is —(alk$_1$)$_m$—X—(alk$_2$)$_n$—W wherein m is 1, n is 0 and W is hydrogen, the 5-substituent becomes —(alk$_1$)$_m$—X—H. The —XH group is advantageously protected in the manner described below.

The appropriate 3-(protected hydroxy)-5-substituted anilines are reacted with an alkyl beta-ketoester in the presence of acetic acid in a reaction-inert solvent such as benzene or toluene at temperatures of from about 50° C. to the reflux temperature of the solvent under conditions which result in removal of by-product water to provide the corresponding beta-[3-protected hydroxy)-5-substituted anilino]-beta-($R_4$)-acrylate (VI).

The alkyl beta-anilino-beta-($R_4$)-acrylate (VI) is then reduced to the corresponding alkyl-3-[(3-protected hydroxy)-5-substituted anilino]-3-($R_4$)-propionate (VII) by, for example, sodium borohydride-acetic acid or catalytic hydrogenation (heterogeneous or homogeneous).

Of course, when the protecting group or groups are benzyl or substituted benzyl, catalytic hydrogenation will result in their removal. For this reason, methyl or

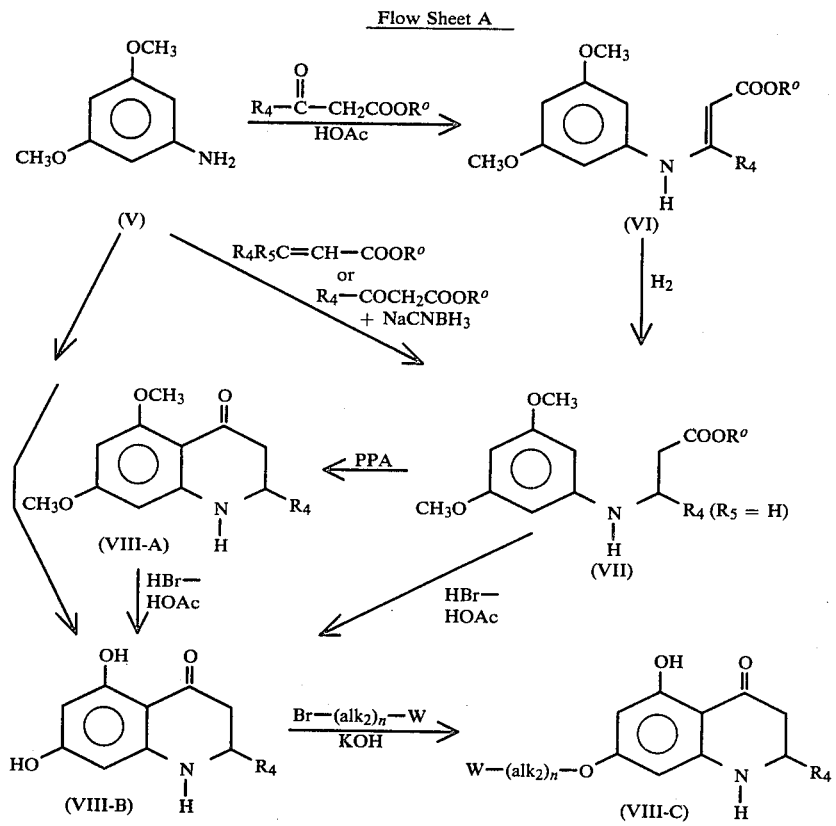

Flow Sheet A $R^o$ in the above flow sheet represents alkyl having from one to six carbon atoms. ($R_5$, for the purpose of illustration in the overall Flow Sheet, is represented as hydrogen. However, in the sequence V→VI or V→VIIIB, $R_5$ can be hydrogen, methyl or ethyl.)

ethyl groups are preferred as protecting groups for the 3- and/or 5-hydroxy groups of formula (V) reactants.

Alternatively, compounds of formula (VII) can be prepared directly from compounds of formula (V) by reaction of formula (V) compounds with an alkyl 3,3-

R4R5-acrylate in acetic acid at temperatures ranging from 0° C. to the reflux temperature.

Alternatively, compounds of formula (VIII-B) can be prepared directly by condensation of equimolar quantities of (V) with the appropriate substituted acrylic acid (R4R5C=CH-COOH) in pyridine hydrochloride at 150°-200° C.

In addition, when the R4,R5 groups are both alkyl, treatment of (V) and the alkyl R4,R5 acrylate in a reaction-inert solvent, e.g. tetrahydrofuran, with mercuric acetate followed by reduction with sodium borohydride gives (VII).

Direct conversion of compounds of formula (V) to compounds of formula (VII) is also conveniently achieved by treating a 3,5-(diprotected hydroxy)aniline hydrochloride with an excess of an alkyl acetoacetate, e.g. ethyl acetoacetate, in the presence of sodium cyanoborohydride in a solvent such as methanol.

The alkyl 3-anilino-3-(R4)-propionate (VII) is then cyclized to the corresponding 2-(R4)-quinolin-4-one (formula VI-A or -B) by means of a suitable cyclizing agent such as polyphosphoric acid (PPA), hydrogen bromide-acetic acid, sulfuric acid, and others known to those skilled in the art.

The ether protecting, or blocking, groups on the 3-(and 5-)hydroxy groups can be removed at the time of cyclization through the use of 48% hydrobromic acid in acetic acid as cyclizing agent and deblocking agent. However, when Z is —(alk$_1$)$_m$—X—(alk$_2$)$_n$— cyclization agents such as polyphosphoric acid or trifluoroacetic acid must be used to avoid cleavage of the ether or thioether linkage. Alternatively, the protecting group (or groups) can be removed subsequent to the cyclization reaction. When the protecting groups are benzyl or substituted benzyl groups, they can be removed by catalytic hydrogenolysis using palladium or platinum supported on carbon or by solvolysis using trifluoroacetic acid. Of course, when group —Z—W contains sulfur, acid debenzylation rather than catalytic debenzylation is used.

Group R6, if not already present in compounds of formula (VIII-A-C), can be introduced into said compounds by reaction with the appropriate Cl-R6 or Br-R6 reactant according to known procedures. Of course, when an acyl, e.g. acetyl, group R6 is desired in products of formulae (I)-(III), such groups are generally introduced at that point in the reaction sequence (Flow Sheet B) following formation of formula (II) or (III) compounds wherein R6 is hydrogen, e.g., by acylation with the appropriate acyl halide according to known procedures.

Compounds of formula (VIII) and, of course, of formula (VIII-A-C), are converted by the following illustrative sequence (Flow Sheet B) to representative compounds of formulae (II) and (III) (R5 and R6=H in the illustration).

Flow Sheet B

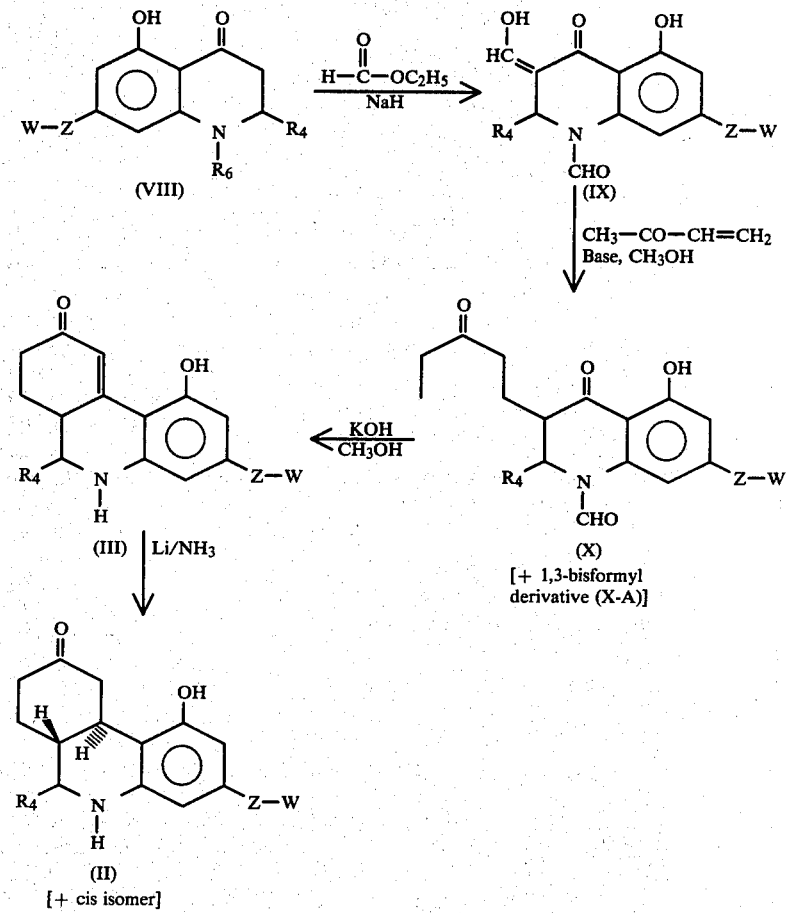

The quinolines of formula (VIII) are converted to hydroxymethylene derivatives of formula (IX) by reaction with ethyl formate and sodium hydride. The bisformylated derivative thus produced is treated with methyl vinyl ketone to give a mixture of the corresponding mono-N-formylated Michael adduct (X) and 1,3-bis-formylated Michael adduct. The two products are conveniently separated by column chromatography on silica gel.

Aldol condensation of the mono-N-formyl compound of formula (X) affords the enone (III).

The enone (III) is converted by Birch reduction to a compound of formula (II). The Birch reduction is favored because it offers stereoselectivity resulting in formation of the desired trans-ketone of formula (II) as the major product.

The hydroxy ketones of formula (II) and (III) (compounds wherein $R_1$ is hydrogen) appear to be rather unstable to oxidation as evidenced by color formation upon standing. They can be stabilized by acylation, particularly acetylation, of the 1-hydroxyl group ($OR_1$) with acetic anhydride in pyridine, and by formation of acid addition salts, e.g., hydrochlorides.

The 1-acyloxy derivatives of formula I ($R_1$ is acyl) are converted to the corresponding hydroxy derivatives ($R_1$=H) by cleavage of the acetyl group by standard methods.

The 3-hydroxy-5-(Z-W-substituted)anilines (XV) are prepared from corresponding 5-(Z-W-substituted)resorcinols via the Bucherer Reaction which comprises reacting the appropriate 5-(Z-W-substituted)resorcinol with aqueous ammonium sulfite or bisulfite. The reaction is conducted in an autoclave at elevated temperatures, e.g. from about 150° to about 230° C. The aniline product is isolated by acidifying the cooled reaction mixture and extracting the acid mixture with, for example, ethyl acetate. The acid solution is neutralized and extracted with a suitable solvent, e.g. chloroform, to recover the aniline product. Alternatively, the aniline product is isolated by extracting the cooled reaction mixture with an appropriate solvent followed by column chromatography of the crude product.

The 5-(Z-W-substituted)resorcinols, if not known, are prepared from 3,5-dihydroxybenzoic acid. The procedure comprises esterifying 3,5-dihydroxybenzoic acid in which the hydroxy groups are protected (e.g., as methyl, ethyl or benzyl ethers); or alternatively, amidating the 3,5-[di(protected hydroxy)]benzoic acid.

The overall abbreviated sequence is illustrated below (Flow Sheet C)

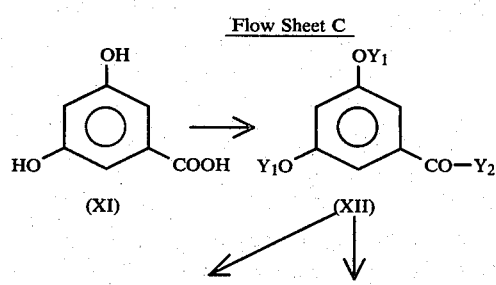

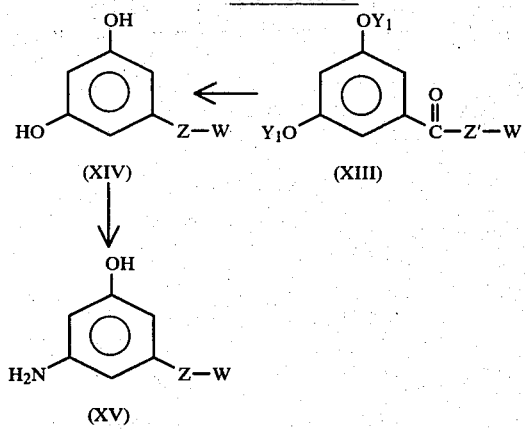

The starting material, 3,5-dihydroxybenzoic acid (XI) is converted to a compound of formula (XII) wherein $Y_2$ represents an alkoxy group, desirably methoxy or ethoxy for ease of preparation, or an amino group; and $Y_1$ is a hydroxy protecting group, by methods described in the literature.

The diprotected benzoic acid derivative (XII) is then converted to a compound of formula (XIV) by known technology. In one procedure (XII) is hydrolyzed to the corresponding acid ($Y_2$=OH), or lithium salt, and reacted with the appropriate alkyl lithium to produce an alkyl disubstituted phenyl ketone ($Y_2$=alkyl). When methyl lithium is used, the resulting acetophenone derivative is treated with a Grignard Reagent (W-Z'-MgBr). The intermediate adduct is hydrolyzed to the corresponding alcohol which is then hydrogenolyzed to replace the hydroxy group with hydrogen. This procedure is especially useful for those compounds wherein Z is alkylene.

The ether groups are deblocked by suitable means: treatment with pyridine hydrochloride ($Y_1$=methyl) or catalytic hydrogenolysis ($Y_1$=benzyl), or by treatment with an acid such as trifluoroacetic acid, hydrochloric, hydrobromic or sulfuric acids. Acid debenzylation is, of course, used when the group —Z—W contains sulfur.

A further method for converting compounds of formula (XII) to those of formula (XIV) comprises reaction of a ketone of formula (XII, $Y_2$=alkyl) with the appropriate triphenyl phosphonium bromide derivative [($C_6H_5$)$_3$P$^+$-Z-W]Br$^-$ in the presence of a base (e.g., sodium hydride). The reaction proceeds via an alkene which is subsequently catalytically hydrogenated to the corresponding alkane (Z-W) and deblocked to the dihydroxy compound (XIV). Of course, when —Z— is $(alk_1)_m$—X—$(alk_2)_n$, X is 0, and when $Y_1$ is benzyl, the catalytic hydrogenation also results in cleavage of the benzyl ethers.

Alternatively, conversion of structure (XII) compounds to those of structure (XIV) can be achieved by the sequence (XII)→(XIII)→(XIV). In this sequence, the diprotected benzamide (XII,$Y_2$=NH$_2$) is converted to the ketone (XIII,Z'=Z less one CH$_2$ group) by reaction with the appropriate Grignard reagent (BrMg-Z'-W) followed by reaction with methyl- or ethyl-magnesium halide to form the corresponding carbinol. Dehydration of the carbinol, e.g., with p-toluenesulfonic acid, affords the corresponding alkene which is then catalytically hydrogenated (Pd/C) to the alkane (XIV).

The ether groups are deblocked (converted to hydroxy) as described above.

When Z is alkylene, $Y_1$ is desirably alkyl having from one to four carbon atoms or benzyl. The function of group $Y_1$ is to protect the hydroxy groups during subsequent reactions. It is its ability to perform a specific function; i.e., protection of the hydroxy groups, rather than its structure which is important. The selection and identification of appropriate protecting groups can easily and readily be made by one skilled in the art.

Preparation of ZW-substituted resorcinols (XIV) is disclosed in detail in U.S. Pat. No. 4,143,139. The suitability and effectiveness of a group as a hydroxy protecting group are determined by employing such a group in the above-illustrated reaction sequences. It should, therefore, be a group which is easily removed to permit restoration of the hydroxy groups. Methyl is favored as a protecting alkyl group since it is easily removed by treatment with pyridine hydrochloride. The benzyl group, if used as a protecting group, is removed by catalytic hydrogenolysis or acid hydrolysis.

When Z is $-(alk_1)_m-X-(alk_2)_n-$, $Y_1$ is preferably benzyl or a substituted benzyl group since it can subsequently be removed without detriment to the Z group.

Formula (XV) compounds can, alternatively, be prepared from 3-amino-5-hydroxybenzoic acids via the procedure of Flow Sheet D below.

Compounds of formula (XVA) wherein $-Z-W$ is $-$alkylene$-W$ or $-(alk_1)-X'-(alk_2)_n-W$ wherein $(alk_1)$, $(alk_2)$, W and n are as defined above and X' is O or S, are obtained by the following sequence (Flow Sheet D).

Flow Sheet D
(Ac = acetyl)

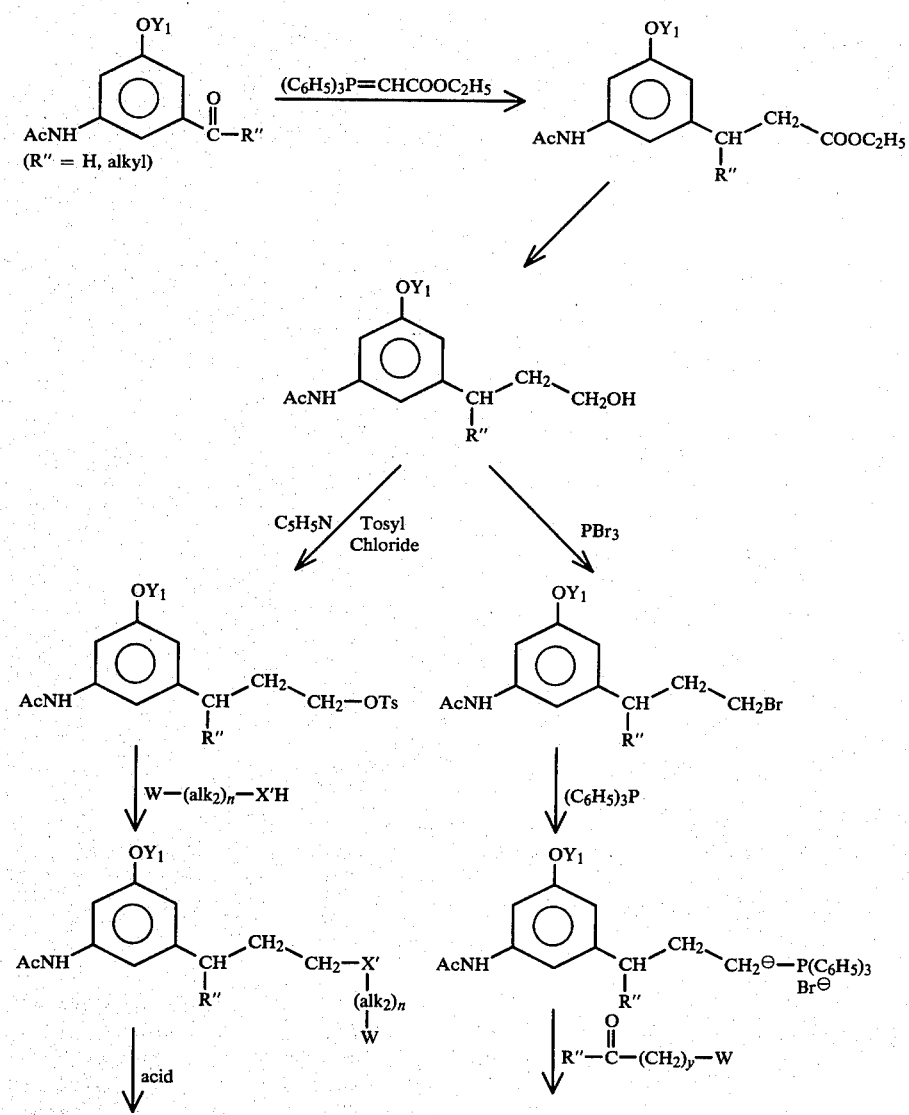

-continued

Flow Sheet D
(Ac = acetyl)

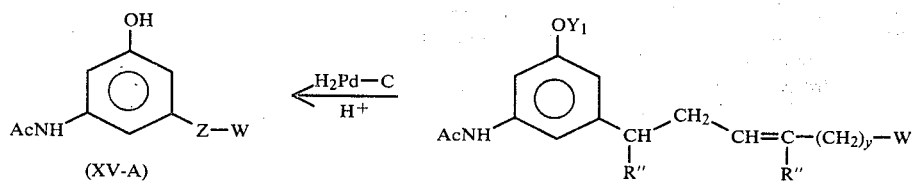

(XV-A)

The first step in the above sequence (the Wittig reaction) provides opportunity, by choice of appropriate reactants, to produce compounds having straight or branched alkylene groups. The amino group is protected by acetylation according to standard procedures. In the given illustration, the value of R" as methyl or ethyl permits formation of a compound having alkyl substitution on the carbon atom adjacent to the phenyl group. Substitution of a methyl or ethyl group at other sites, e.g., the beta-carbon atoms of the alkylene group, is achieved by choice of the appropriate carboalkoxy alkylidene triphenylphosphorane, e.g. $(C_6H_5)_3P=C(R'')—COOC_2H_5$. The unsaturated ester thus produced is reduced to the corresponding saturated alcohol by reaction with lithium aluminum hydride. The presence of a small amount of aluminum chloride sometimes accelerates this reaction. Alternatively, when $Y_1$ is other than benzyl (e.g. methyl), the alcohol is produced by catalytic reduction of the unsaturated ester using palladium-carbon, followed by treatment of the saturated ester thus produced with lithium aluminum hydride. Conversion of the alcohol to the corresponding tosylate or mesylate followed by alkylation of the tosylate or mesylate with an alkali metal salt of the appropriate HX'—(alk$_2$)$_n$—W reactant, and finally removal of the protecting groups ($Y_1$) affords the desired compound (XVA). When X' is sulfur, the protecting group $Y_1$ is methyl.

A variation of the above sequence comprises bromination of the alcohol rather than converting it to a tosylate or mesylate. Phosphorous tribromide is a convenient brominating agent. The bromo derivative is then reacted with the appropriate HX'—(alk$_2$)$_n$—W in the presence of a suitable base (Williamson reaction).

The bromo compounds also serve as valuable intermediates for increasing the chain length of the alkylene moiety in the above sequence to give compounds wherein Z is —alkylene—W. The process comprises treating the bromo derivative with triphenyl phosphine to produce the corresponding triphenylphosphonium bromide. Reaction of the triphenylphosphonium bromide with the appropriate aldehyde or ketone in the presence of a base such as sodium hydride or n-butyl lithium affords an unsaturated derivative which is then catalytically hydrogenated to the corresponding saturated compound.

In this variation, the value of the protecting group ($Y_1$) selected depends upon the particular sequence followed. When the vertical sequence on the right is used, benzyl is the preferred protecting group by reason of the catalytic hydrogenation step. Methyl is the preferred protecting group when the left vertical sequence is followed, since it is conveniently removed by treatment with acid as described herein.

Compounds of formula (I) or (II) wherein —Z—W is —(alk$_1$)$_m$—X—(alk$_2$)$_n$—W and X is —SO— or —SO$_2$— are obtained by oxidation of the corresponding compounds in which X is —S—. Hydrogen peroxide is a convenient agent for oxidation of the thio ethers to sulfoxides. Oxidation of the thio ethers to corresponding sulfones is conveniently accomplished by means of a peracid such as perbenzoic, perphthalic or m-chloroperbenzoic acid. This latter peracid is especially useful since the by-product m-chlorobenzoic acid is easily removed.

Esters of compounds of formulae (I)–(III) wherein $R_1$ is alkanoyl or —CO—(CH$_2$)$_p$—NR$_2$R$_3$ are readily prepared by reacting formulae (I)–(III) compounds wherein $R_1$ is hydrogen with the appropriate alkanoic acid or acid of formula HOOC—(CH$_2$)$_p$—NR$_2$R$_3$ in the presence of a condensing agent such as dicyclohexylcarbodiimide. Alternatively they are prepared by reaction of a formula (I)–(III) compound with the appropriate alkanoic acid chloride or anhydride, e.g., acetyl chloride or acetic anhydride, in the presence of a base such as pyridine.

The presence of a basic group in the ester moiety (OR$_1$) in the compounds of this invention permits formation of acid-addition salts involving said basic group. When the herein described basic esters are prepared via condensation of the appropriate amino acid hydrochloride (or other acid addition salt) with the appropriate compound of formula (I) in the presence of a condensing agent, the hydrochloride salt of the basic ester is produced. Careful neutralization affords the free base. The free base form can then be converted to other acid addition salts by known procedures.

Acid addition salts can, of course, as those skilled in the art will recognize, be formed with the nitrogen of the benzo[c]quinoline system. Such salts are prepared by standard procedures. The basic ester derivatives are, of course, able to form mono- or di-acid addition salts because of their dibasic functionality.

The analgesic properties of the compounds of this invention are determined by tests using thermal nociceptive stimuli, which as the mouse tail flick procedure, or chemical nociceptive stimuli, such as measuring the ability of a compound to suppress phenylbenzoquinone irritant-induced writhing in mice. These tests and others are described below.

Tests Using Thermal Nociceptive Stimuli (a) Mouse Hot Plate Analgesic Testing

The method used is modified after Woolfe and MacDonald, *J. Pharmacol. Exp. Ther.*, 80, 300–307 (1944). A controlled heat stimulus is applied to the feet of mice on a ⅛" thick aluminum plate. A 250 watt reflector infrared heat lamp is placed under the bottom of the aluminum plate. A thermal regulator, connected to thermistors on the plate surface, programs the heat lamp to maintain a constant temperature of 57° C. Each mouse is dropped into a glass cylinder (6½" diameter) resting on the hot plate, and timing is begun when the animal's feet touch the plate. At 0.5 and 2 hours after treatment with the test compound, the mouse is observed for the first "flicking" movements of one or both hind feet, or until 10 seconds elapse without such movements. Morphine has an MPE$_{50}$=4–5.6 mg./kg. (s.c.).

(b) Mouse Tail Flick Analgesic Testing

Tail flick testing in mice is modified after D'Amour and Smith, *J. Pharmacol. Exp. Ther.*, 72, 74–79 (1941), using controlled high intensity heat applied to the tail. Each mouse is placed in a snug-fitting metal cylinder, with the tail protruding through one end. This cylinder is arranged so that the tail lies flat over a concealed heat lamp. At the onset of testing, an aluminum flag over the lamp is drawn back, allowing the light beam to pass through the slit and focus onto the end of the tail. A timer is simultaneously activated. The latency of a sudden flick of the tail is ascertained. Untreated mice usually react within 3–4 seconds after exposure to the lamp. The end point for protection is 10 seconds. Each mouse is tested at 0.5 and 2 hours after treatment with morphine and the test compound. Morphine has an MPE$_{50}$ of 3.2–5.6 mg./kg. (s.c.).

(c) Tail Immersion Procedure

The method is a modification of the receptacle procedure developed by Benbasset, et. al., *Arch. int. Pharmacodyn.*, 122, 434 (1959). Male albino mice (19–21 g.) of the Charles River CD-1 strain are weighed and marked for identification. Five animals are normally used in each drug treatment group with each animal serving as its own control. For general screening purposes, new test agents are first administered at a dose of 56 mg./kg. intraperitoneally or subcutaneously, delivered in a volume of 10 ml./kg. Preceding drug treatment and at 0.5 and 2 hours post drug, each animal is placed in the cylinder. Each cylinder is provided with holes to allow for adequate ventilation and is closed by a round nylon plug through which the animal's tail protrudes. The cylinder is held in an upright position and the tail is completely immersed in the constant temperature waterbath (56° C.). The endpoint for each trail is an energetic jerk or twitch of the tail coupled with a motor response. In some cases, the endpoint may be less vigorous post drug. To prevent undue tissue damage, the trail is terminated and the tail removed from the waterbath within 10 seconds. The response latency is recorded in seconds to the nearest 0.5 second. A vehicle control and a standard of known potency are tested concurrently with screening candidates. If the activity of a test agent has not returned to baseline values at the 2-hour testing point, response latencies are determined at 4 and 6 hours. A final measurement is made at 24 hours if activity is still observed at the end of the test day.

Test Using Chemical Nociceptive Stimuli

Suppression of Phenylbenzoquinone Irritant-Induced Writhing

Groups of 5 Carworth Farms CF-1 mice are pretreated subcutaneously or orally with saline, morphine, codeine or the test compound. Twenty minutes (if treated subcutaneously) or fifty minutes (if treated orally) later, each group is treated with intraperitoneal injection of phenylbenzoquinone, an irritant known to produce abdominal contractions. The mice are observed for 5 minutes for the presence or absence of writhing starting 5 minutes after the injection of the irritant. MPE$_{50}$'s of the drug pretreatments in blocking writhing are ascertained.

Tests Using Pressure Nociceptive Stimuli

Effect on the Haffner Tail Pinch Procedure

A modification of the procedure of Haffner, *Experimentelle Prufung Schmerzstillender. Mittel Deutch Med. Wschr.*, 55, 731–732 (1929) is used to ascertain the effects of the test compound on aggressive attacking responses elicited by a stimulus pinching the tail. Male albino rats (50–60 g.) of the Charles River (Sprague-Dawley) CD-strain are used. Prior to drug treatment, and again at 0.5, 1, 2 and 3 hours after treatment, a Johns Hopkins 2.5-inch "bulldog" clamp is clamped onto the root of the rat's tail. The endpoint at each trail is clear attacking and biting behavior directed toward the offending stimulus, with the latency for attack reported in seconds. The clamp is removed in 30 seconds if attacking has not yet occurred, and the latency of response is recorded as 30 seconds. Morphine is active 17.8 mg./kg. (i.p.).

Tests Using Electrical Nociceptive Stimuli

The "Flinch-Jump" Test

A modification of the flinch-jump procedure of Tenen, *Psychopharmacologia*, 12, 278–285 (1968) is used for determining pain thresholds. Male albino rats (175–200 g.) of the Charles River (Sprague-Dawley) CD strain are used. Prior to receiving the drug, the feet of each rat are dipped into a 20% glycerol/saline solution. The animals are then placed in a chamber and presented with a series of 1-second shocks to the feet which are delivered in increasing intensity at 30-second intervals. These intensities are 0.26, 0.39, 0.52, 0.78, 1.05, 1.31, 1.58, 1.86, 2.13, 2.42, 2.72, and 3.04 mA. Each animal's behavior is rated for the presence of (a) flinch, (b) squeak and (c) jump or rapid forward movement at shock onset. Single upward series of shock intensities are presented to each rat just prior to, and at 0.5, 2, 4 and 24 hours subsequent to drug treatment.

Results of the above tests are recorded as percent maximum possible effect (% MPE). The % MPE of each group is statistically compared to the % MPE of the standard and the predrug control values. The % MPE is calculated as follows:

$$\% \text{ MPE} = \frac{\text{test time} - \text{control time}}{\text{cutoff time} - \text{control time}} \times 100$$

In the table below, the analgesic activity for representative trans-5,6,6a,7,8,9,10,10a-octahydro-1-acetoxy-9-amido-3-(5-phenyl-2-pentyloxy)benzo[c]quinolines of the invention in the phenylbenzoquinone-induced writhing test is reported in terms of MPE$_{50}$, the dose at which half of the maximal possible analgesic effect is observed in a given test.

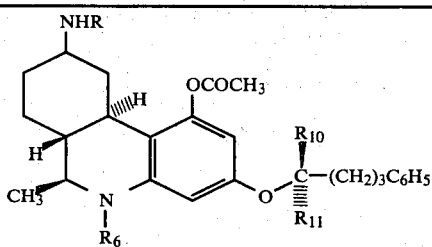

| Compound of Example | —NHR[b] | R6 | R10 | R11 | PBQ Writhing, MPE50 (mg./kg.) |
|---|---|---|---|---|---|
| 2≠[a] | NHCOCH3 ↑ | H | H CH3 | CH3 H | 0.42 |
| 3≠[a] | NHSO2CH3 ↑ | H | H CH3 | CH3 H | 4.25 |
| 4B≠[a] | NHCOCF3 ↑ | H | H CH3 | CH3 H | 77% at 56 mg./kg. |
| 4C≠[a] | NHCO(CH2)3CH3 ↑ | H | H CH3 | CH3 H | 80% at 56 mg./kg. |
| 6≠[a] | NHSO2CH3 ⦃ | H | H CH3 | CH3 H | 35.5 |
| 9≠[a] | NHCOCH3 ≡ | CH3 | H CH3 | CH3 H | 2.67 |
| 10A≠ | NHCOCH3 ↑ | CH3 | CH3 | H | 0.1 |
| 10B≠[a] | NHCOCH3 ↑ | CH3 | H CH3 | CH3 H | 0.01 |
| 11* | NHCOCH3 ↑ | CH3 | H | CH3 | 0.0032 |

≠ racemic mixture
*dextro enantiomer, [α]D + 154.88°
[a] 50/50 mixture of side chain diastereomers at the 3-position.
[b] ↑, indicates beta configuration;

, indicates alpha configuration;

⦃, indicates a mixture of the above.

As mentioned above, the compounds of the invention are especially useful as antiemetic and antinausea agents in mammals. They are particularly useful in preventing emesis and nausea induced by antineoplastic agents.

The antiemetic properties of the compounds of formula (I) are determined in unanesthetized unrestrained cats according to the procedure described in Proc. Soc. Exptl. Biol. and Med., 160, 437–440 (1979).

The compounds of the present invention are active analgesics, antiemetics or antinauseants via oral and parenteral administration and are conveniently administered for either or both of these uses in composition form. Such compositions include a pharmaceutical carrier selected on the basis of the chosen route of administration and standard pharmaceutical practice. For example, they may be administered in the form of tablets, pills, powders or granules containing such excipients as starch, milk sugar, certain types of clay, etc. They may be administered in capsules, in admixtures with the same or equivalent excipients. They may also be administered in the form of oral suspensions, solutions, emulsions, syrups and elixirs which may contain flavoring and coloring agents. For oral administration of the therapeutic agents of this invention, tablets or capsules containing from about 0.01 to about 100 mg. are suitable for most applications.

Suspensions and solutions of these drugs, particularly those wherein $R_1$ is hydroxy, are generally prepared just prior to use in order to avoid problems of stability of the drug (e.g. oxidation) or of suspensions or solution (e.g. precipitation) of the drug upon storage. Compositions suitable for such are generally dry solid compositions which are reconstituted for injectable administration.

The physician will determine the dosage which will be most suitable for an individual patient and it will vary with the age, weight and response of the particular patient and the route of administration. Generally, however, the initial analgesic dosage, as well as the initial dosage for prevention or treatment of nausea, in adults may range from 0.01 to 500 mg. per day in single or divided doses. In many instances, it is not necessary to exceed 100 mg. daily. The favored oral dosage range is from about 0.01 to about 300 mg./day; the preferred range is from about 0.10 to about 50 mg./day. The favored parenteral dose is from about 0.01 to about 100 mg./day; the preferred range from about 0.01 to about 20 mg./day.

EXAMPLE 1 dl-1-Acetoxy-5,6,6a-beta, 7-tetrahydro-6-beta-methyl-3-(5-phenyl-2-pentyloxy)-benzo[c]quinoline-9(8H)oxime To a solution of 10.0 g. (0.023 mole) dl-1-acetoxy-5,6,6a-beta, 7-tetrahydro-6-beta-methyl-3-(5-phenyl-2-pentyloxy)benzo[c]quinoline-9(8H)one (m.p. 136°–140° C., prepared by the method of Belgium Pat. No. 854,655) dissolved in 25 ml. of dry pyridine under nitrogen atmosphere was added 2.36 g. (0.034 mole) hydroxylamine hydrochloride in one portion. The resultant solution was stirred at ambient temperature for 18 hours. The reaction mixture was diluted with 500 ml. ethyl acetate and stirred for 5 minutes with 250 ml. 10% (w/v) hydrochloric acid. The organic phase was separated and washed three more times with 10% hydrochloric acid. Orange solids precipitated with each wash and were filtered before the subsequent wash. The combined orange solids were stirred for 10 minutes in 75 ml. methylene chloride. The solids were filtered and dried in vacuo over phosphorus pentoxide to yield 7.8 g. (75% yield) of the title compound, m.p. 182°–185° C. Mass spectrum (m/e): 448(M+); infrared spectrum (KBr), microns: 2.94 (OH), 6.13 (COO), 6.4 (C=N), 8.0(—O—).

EXAMPLE 2 dl-9-beta-Acetamido-1-acetoxy-5,6,6a-beta, 7,8,9,10,10a-alpha-octahydro-6-beta-methyl-3-(5-phenyl-2-pentyloxy)benzo[c]quinoline hydrochloride dl-1-Acetoxy-5,6,6a-beta, 7-tetrahydro-6-beta-methyl-3-(5-phenyl-2-pentyloxy)benzo[c]quinoline-9(8H)-oxime, 3.2 g. (0.007 mole), was combined with 1.5 g. 5% palladium-on-carbon catalyst and 100 ml. methanol in a pressure bottle and hydrogenated at 50 psi (3.5 kg./cm.²) for three hours. The catalyst was filtered through diatomaceous earth, washing well with methanol. The combined methanol filtrates were evaporated in vacuo leaving a foam which was immediately acetylated by dissolving in 200 ml. methylene chloride and adding first 3.03 g. (0.03 mole=3 equiv.) triethylamine, then 3.66 g. (0.03 mole) 4-dimethylaminopyridine. After the reaction was cooled to 0° C. in an ice-water bath, 3.06 g. (0.03 mole) acetic anhydride was added dropwise under nitrogen atmosphere. After stirring at 0° C. for 30 minutes, the reaction mixture was washed with 4×50 ml. of 10% (w/v) hydrochloric acid, 2×50 ml. water, 1×50 ml. brine, and dried over anhydrous magnesium sulfate. The solvent was evaporated in vacuo to afford a light brown foam (2.7 g.) which was chromatographed on 50 parts by weight of silica gel eluting with ethyl acetate/toluene (1:1 by volume). Similar fractions were combined and the solvent was removed in vacuo. The residual oil was taken up in diethyl ether and acidified with dry hydrogen chloride under a nitrogen atmosphere. The resultant solids were filtered and dried in vacuo yielding 0.91 g. (25% overall for two steps) of title compound, m.p. 188°–190° C.; mass spectrum (m/e): 478 (M+); infrared spectrum (KBr), microns: 5.6 ($CH_3CO$), 5.96 ($CH_3CONH$); $^1$H-NMR ($CDCl_3$) ppm (delta): 2.06 (—$NHCOCH_3$), 2.5 ($CH_3CO$).

When the above procedure is repeated but 6.5 g. of Pd/C catalyst is employed and the hydrogenation is carried out at atmospheric pressure, the results are substantially unchanged.

EXAMPLE 3 dl-9-beta-Methylsulfonylamino-1-acetoxy-5,6,6a-beta, 7,8,9,10,10a-alpha-octahydro-6-beta-methyl-3-(5-phenyl-2-pentyloxy)benzo[c]quinoline dl-1-Acetoxy-5,6,6a-beta, 7-tetrahydro-6-beta-methyl-3-(5-phenyl-2-pentyloxy)benzo[c]quinoline-9(8H)-oxime, 0.8 g. (0.0018 mole) was combined with 0.4 g. of 5% palladium-on-carbon catalyst in 40 ml. of methanol and the mixture hydrogenated at 50 psi (3.5 kg./cm.$^2$) for two hours. The catalyst was removed by filtration and the solvent evaporated in vacuo to provide the 6a,10a-trans-9-beta-amino compound as a light tan foam. The foam was dissolved in 30 ml. of methylene chloride, 0.21 g. (0.0021 mole), triethylamine and 0.256 g. (0.0021 mole) 4-dimethylaminopyridine were added, the mixture cooled to 0° C., and 0.24 g. (0.0021 mole) of methanesulfonyl chloride was added dropwise over three minutes. The reaction mixture was stirred at 0° C. under a nitrogen atmosphere for one hour, poured into 50 ml. each of water and methylene chloride. The aqueous layer was extracted with 20 ml. of methylene chloride and the combined organic layers washed with 4×20 ml. of 10% (by weight) hydrochloric acid, 40 ml. of water, 40 ml. of saturated sodium bicarbonate solution, 20 ml. water and 20 ml. of brine. The washed extracts were dried over anhydrous magnesium sulfate and solvent evaporated in vacuo to afford 0.520 g. (56.2%) of crude product which was purified by column chromatography on 20 g. of silica gel, eluting with 3:1 by volume methyl acetate/cyclohexane. The product-containing fractions were combined and evaporated in vacuo to obtain 300 mg. (58% recovery, 32% yield) of purified title compound as a foam. Mass spectrum (m/e): M+ 514. The $^1$H-NMR spectrum ($CDCl_3$) showed that the hydrogen in the 9-position produced a peak at 4.78 delta (m, 1H) indicative of an alpha hydrogen. Thus, the 9-methylsulfonylamino group was in the beta orientation.

EXAMPLE 4

When the procedures of Examples 2 and 3 were carried out but the acetic anhydride or methanesulfonyl chloride employed therein replaced by benzoic anhydride, trifluoroacetic anhydride, valeric acid anhydride or p-toluenesulfonyl chloride, the following compounds were obtained.

A.     dl-9-beta-Benzamido-1-acetoxy-5,6,6a-beta, 7,8,9,10,10a-alpha-octahydro-6-beta-methyl-3-(5-phenyl-2-pentyloxy)benzo[c]quinoline hydrochloride. Mass spectrum (m/e): M+ 540, 518, 497.

Analysis: Calcd. for $C_{34}H_{40}O_4N_2HCl$: C, 70.75; H, 7.16; N, 4.85. Found: C, 71.29; H, 7.04; N, 4.91.

B.     dl-9-beta-Trifluoroacetylamino-1-acetoxy-5,6,6a-beta, 7,8,9,10,10a-alpha-octahydro-6-beta-methyl-3-(5-phenyl-2-pentyloxy)benzo[c]quinoline.     $^1$H-NMR($CDCl_3$) ppm (delta): 1.02–3.15(m), 4.3(s), 4.7(s), 5.72–6.76(m); infrared spectrum (KBr) microns: 3.0, 3.43, 5.65, 5.85, 8.3–8.67 (broad), 12.5, 13.4–13.8, 14.35.

Analysis: Calcd. for $C_{29}H_{35}O_4N_2F_3$: C, 65.40; H, 6.62; N, 5.26. Found: C, 64.20; H, 6.67; N, 4.82.

C.     dl-9-beta-Valeroylamino-1-acetoxy-5,6,6a-beta-7,8,9,10,10a-alpha-octahydro-6-beta-methyl-3-(5-phenyl-2-pentyloxy)benzo[c]quinoline. $^1$H-NMR ($CDCl_3$) ppm (delta): 0.928–3.12(m), 4.3(m,1H), 4.66(m,9-axial H), 5.94(m,2H), 6.83(s,2H aromatic). Mass Spectrum (m/e): M+ 520.

D.     dl-9-beta-(4-methylphenylsulfonyl)amino-1-acetoxy-5,6,6a-beta, 7,8,9,10,10a-alpha-octahydro-6-beta-methyl-3-(5-phenyl-2-pentyloxy)benzo[c]quinoline; tan-yellow crystals (20% yield).

In like manner the appropriate starting material of formula (III) is converted to the corresponding oxime of formula (IV), below, by the procedure of Example 1 and the oxime reduced and acylated by the procedure of Example 2 or reduced and sulfonylated by the procedure of Example 3 to provide the compounds of formula (I), below.

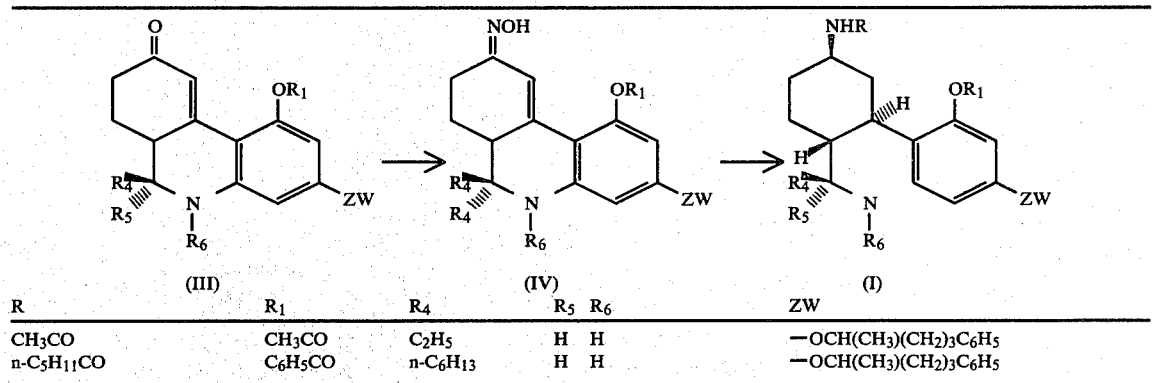

| R | $R_1$ | $R_4$ | $R_5$ | $R_6$ | ZW |
|---|---|---|---|---|---|
| $CH_3CO$ | $CH_3CO$ | $C_2H_5$ | H | H | —$OCH(CH_3)(CH_2)_3C_6H_5$ |
| n-$C_5H_{11}CO$ | $C_6H_5CO$ | n-$C_6H_{13}$ | H | H | —$OCH(CH_3)(CH_2)_3C_6H_5$ |

-continued

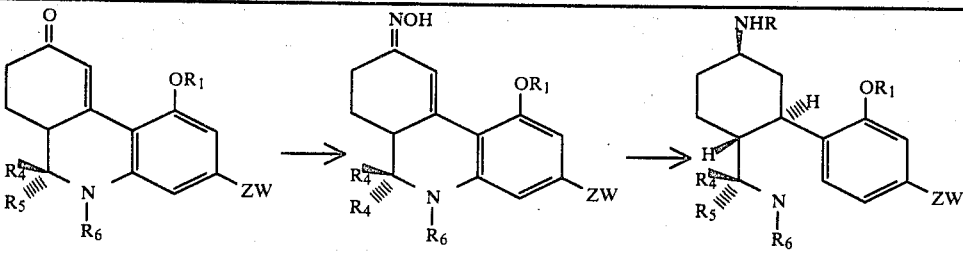

| R | R1 | R4 | R5 | R6 | ZW |
|---|----|----|----|----|----|
| iso-$C_3H_7$CO | $CH_3CH_2$CO | n-$C_5H_{11}$ | H | H | —OCH($CH_3$)($CH_2$)$_3C_6H_5$ |
| $CH_2$=CHCO | $CH_3(CH_2)_2$CO | $CH_3$ | H | H | —OCH($CH_3$)($CH_2$)$_4CH_3$ |
| $CH_3$CH=CHCO | $CH_3(CH_2)_3$CO | n-$C_4H_9$ | H | H | —OCH($CH_3$)($CH_2$)$_3C_6H_5$ |
| $CH_3(CH_2)_2$CH=CHCO | $CH_3$CO | H | H | H | —OCH($CH_3$)($CH_2$)$_3C_6H_5$ |
| $CH_2$=CH($CH_2$)$_4$CO | $C_6H_5$CO | $C_6H_5(CH_2)_2$ | H | H | —OCH($CH_3$)($CH_2$)$_3C_6H_5$ |
| $CH_3CH_2$CH=C($CH_3$)CO | H | $CH_3$ | H | $CH_3$ | —O($CH_2$)$_3C_6H_5$ |
| CH≡CCO | $CH_3$CO | $CH_3$ | H | H | —C($CH_3$)$_2C_6H_5$ |
| CH≡C($CH_2$)$_4$CO | $CH_3$CO | $CH_3$ | H | H | —O($CH_2$)$_2C_6H_5$ |
| $CH_3$C≡C$CH_2$CO | $C_6H_5$CO | H | H | H | —OCH($CH_3$)($CH_2$)$_3C_6H_5$ |
| $CF_3$CO | $CH_3$CO | H | H | H | —OCH($CH_3$)($CH_2$)$_4CH_3$ |
| $C_6H_5$CO | $C_6H_5$CO | n-$C_3H_7$ | H | H | —OCH($CH_3$)($CH_2$)$_3C_6H_5$ |
| $C_6H_5CH_2$CO | $CH_3$CO | $C_6H_5CH_2$ | H | $CH_3(CH_2)_5$ | —$CH_3$ |
| 2-furoyl | $CH_3$CO | $C_6H_5(CH_2)_4$ | H | $CH_3CH_2$ | —$CH_2CH_3$ |
| 3-thenoyl | $CH_3$CO | H | H | ($CH_3$)$_2$CH | —($CH_2$)$_3CH_3$ |
| 4-pyridyl—CO | $CH_3$CO | n-$C_6H_{13}$ | H | $C_6H_5CH_2CH_2$ | —($CH_2$)$_8CH_3$ |
| 4-$NH_2C_6H_4$CO | $CH_3$CO | $CH_3$ | H | $C_6H_5(CH_2)_4$ | —C($CH_3$)$_2$($CH_2$)$_5CH_3$ |
| 3-$FC_6H_4$CO | $C_6H_5$CO | $C_2H_5$ | H | $C_2H_5$ | —$OCH_3$ |
| 2-$ClC_6H_4$CO | $CH_3$CO | H | H | H | —($CH_2$)$_3OC_6H_5$ |
| 4-$BrC_6H_4$CO | $CH_3$CO | $CH_3$ | H | H | —($CH_2$)$_3$O(4-$FC_6H_4$) |
| 2-$CH_3C_6H_4$CO | $CH_3$CO | $CH_3$ | H | H | —($CH_2$)$_3$O—cyclohexyl |
| 4-$CH_3OC_6H_4$CO | $CH_3$CO | $C_2H_5$ | H | H | —($CH_2$)$_3$O—cyclobutyl |
| $CH_3SO_2$ | $CH_3CH_2$CO | H | H | H | —($CH_2$)$_3OCH_3$ |
| $CH_3CH_2SO_2$ | $CH_3$CO | $C_2H_5$ | H | H | —($CH_2$)$_3$O($CH_2$)$_2$(4-$ClC_6H_4$) |
| $CH_3(CH_2)_3SO_2$ | $CH_3$CO | $CH_3$ | H | H | —($CH_2$)$_3$O—[4-(4-$FC_6H_4$)$C_6H_{10}$] |
| ($CH_3$)$_2$CH($CH_2$)$_2SO_2$ | H | $C_2H_5$ | H | H | —($CH_2$)$_3$O($CH_2$)$_2$(4-$ClC_6H_4$) |
| ($CH_3$)$_3$CC$H_2SO_2$ | $CH_3$CO | H | H | H | —($CH_2$)$_3$O($CH_2$)$_2C_6H_5$ |
| $C_6H_5SO_2$ | $C_6H_5$CO | $CH_3$ | H | H | —($CH_2$)$_4$O—(3-piperidyl) |
| 4-$NH_2C_6H_4SO_2$ | $CH_3$CO | H | H | H | —($CH_2$)$_4$O($CH_2$)$_5$—(4-pyridyl) |
| 4-$BrC_6H_4SO_2$ | $CH_3$CO | H | H | $CH_3$ | —CH($CH_3$)($CH_2$)$_3$O($CH_2$)$_2C_6H_5$ |
| 4-$ClC_6H_4SO_2$ | $CH_3$CO | $C_2H_5$ | H | H | —CH($CH_3$)($CH_2$)$_3$O($CH_2$)$_2CH_3$ |
| 4-$FC_6H_4SO_2$ | $CH_3$CO | H | H | H | —($CH_2$)$_3OC_6H_5$ |
| 4-$CH_3C_6H_4SO_2$ | $CH_3$CO | $C_2H_5$ | H | H | —($CH_2$)$_3OCH_2$(4-$FC_6H_4$) |
| 3-$CH_3OC_6H_4SO_2$ | $CH_3$CO | $CH_3$ | H | $CH_3$ | ($CH_2$)$_9CH_3$ |
| 3-furoyl | H | $CH_3$ | H | CHO | OH |
| 2-thenoyl | $C_6H_5$CO | $C_6H_5(CH_2)_3$ | H | $COOCH_3$ | $CH_2OCH_3$ |
| $CH_3$CO | $CH_3$CO | n-$C_3H_7$ | H | $CH_2COOC_2H_5$ | ($CH_2$)$_4C_3H_5$ |
| $CH_3CH_2$CO | $CH_3CH_2$CO | H | H | ($CH_2$)$_2$COO—n-$C_4H_9$ | CH($CH_3$)($CH_2$)$_5C_6H_{11}$ |
| $CH_3(CH_2)_3$CO | $CH_3(CH_2)_2$CO | ($CH_3$)$_2$CHCH$_2$ | H | COO—i-$C_3H_7$ | CH($CH_3$)($CH_2$)$_2C_7H_{13}$ |
| 2-pyridyl | HCO | ($CH_3$)$_2$CH | H | ($CH_2$)$_4$COO—i-$C_4H_9$ | ($CH_2$)$_3C_6H_5$ |
| 3-pyridyl | $CH_3$CO | $C_6H_5CH_2$ | H | $CH_3$CO | CH($CH_3$)$CH_2$—4-$FC_6H_4$ |
| 3-$NH_2C_6H_4$CO | $CH_3(CH_2)_2$CO | H | H | $CH_3CH_2$CO | CH($CH_3$)($CH_2$)$_2$—4-$ClC_6H_4$ |
| 4-$FC_6H_4$CO | ($CH_3$)$_2$CHCO | H | H | $CH_3(CH_2)_3$CO | ($CH_2$)$_3$—2-pyridyl |
| 4-$ClC_6H_4$CO | $CH_3$CO | H | H | $C_6H_5$CO | ($CH_2$)$_4$—4-pyridyl |
| 2-$BrC_6H_4SO_2$ | $CH_3$CO | $CH_3$ | H | $C_6H_5CH_2$CO | CH($CH_3$)($CH_2$)$_2$—4-piperidyl |
| 3-$CH_3C_6H_4SO_2$ | $CH_3$CO | $CH_3$ | H | $C_6H_5(CH_2)_2$CO | ($CH_2$)$_4$—$CH_3$ |
| 2-$CH_3OC_6H_4SO_2$ | $CH_3$CO | $CH_3$ | H | $C_6H_5(CH_2)_3$CO | $CH_2CH_3$ |
| 2-$FC_6H_4SO_2$ | $CH_3$CO | $CH_3$ | H | H | ($CH_2$)$_9C_6H_5$ |
| $CH_3(CH_2)_4SO_2$ | H | $CH_3$ | H | CHO | CH($C_2H_5$)($CH_2$)$_2$O—2-(4-$C_6H_5$)—$C_7H_{14}$ |

When oximes of formula (IV) wherein $R_1$ or $R_6$ are benzyl, $R_6$ is carbobenzyloxy, are reduced with hydrogen and Pd/C by the above methods, the corresponding compounds of formula (I) are obtained wherein $R_1$ and $R_6$ are hydrogen. Similarly, oximes (IV) in which ZW is benzyloxy are converted to compounds (I) wherein ZW is OH.

EXAMPLE 5

Mixtures of diastereomers of 9-amino-1-acetoxy-5,6,6a-beta, 7,8,9,10,10a-alpha-octahydro-6-beta-methyl-3-(5-phenyl-2-pentyloxy)benzo[c]quinoline To 25 ml. of methanol was added 300 mg. of dl-trans-1-acetoxy-5,6,6a-beta, 7,10,10a-alpha-hexahydro-6-beta-methyl-3-(5-phenyl-2-pentyloxy)benzo[c]quinoline-9-(8H)one, 300 mg. of 5% palladium-on-carbon and 480 mg. of ammonium chloride. The mixture was hydrogenated at atmospheric pressure and room temperature for 18 hours. The catalyst was removed by filtration, washed with methylene chloride and the filtrates evaporated in vacuo to provide a colorless crystalline residue. This was stirred with 10 ml. of methylene chloride, filtered to remove ammonium chloride and the filtrate evaporated to dryness. The residue was triturated with 20 ml. of ethyl ether, filtered and the product dried at 56° C. (0.5 mm.) for 24 hours. Yield: 262 mg. (87.3%), m.p. 194°–195.5° C. Mass spectrum (m/e): M+ 436;

infrared spectrum (KBr) microns: 2.80, 2.90, 2.97, 3.43, 5.64, 5.70, 6.13, 6.57, 7.25, 8.20, , (broad), 8.87, 9.65, 12.05 (broad).

Analysis: Calcd. for $C_{27}H_{36}N_2O_3 \cdot HCl$: C, 68.50; H, 7.89; N, 5.93. Found: C, 67.93; H, 7.87; N, 5.97.

EXAMPLE 6

Mixed diastereomers of 9-methylsulfonylamino-1-acetoxy-5,6,6a-beta,7,8,9,10,-10a-alpha-octahydro-6-beta-methyl-3-(5-phenyl-2-pentyloxy)benzo[c]quinoline To 10 ml. of methylene chloride was added 218 mg. (0.5 mmole) of mixed diastereomers of 9-amino-1-acetoxy-5,6,6a-beta,7,8,9,10,10a-alpha-octahydro-6-beta-methyl-3-(5-phenyl-2-pentyloxy)benzo[c]quinoline and 0.083 ml. (0.6 mmole) of triethylamine. The solution was cooled to −20° C. and a solution of 57.3 mg. (0.5 mmole of methanesulfonyl chloride in 5 ml. of methylene chloride was added dropwise over eight minutes. The mixture was allowed to warm to 0° C. over 30 minutes, poured onto 20 ml. of ice/water and 20 ml. of methylene chloride, and the layers separated. The aqueous layer was extracted with the same solvent and the combined organic layers washed with water (20 ml.) saturated sodium bicarbonate solution (20 ml.), water (10 ml.), brine (10 ml.) and dried over anhydrous magnesium sulfate. Evaporation of the dried extract afforded a residue which was chromatographed on 10 g. of silica gel, eluting with 1:3 ethyl ether/cyclohexane. The product-containing fractions were combined, solvent evaporated in vacuo to provide a pink foam which was taken up in 10 ml. of ether and filtered. Evaporation of the filtrate yielded 205 mg. (79.8%) of the desired product. Mass spectrum (m/e): 514 M +, 472, 433, 324, 230, 216, 204, 91; infrared spectrum (KBr) microns: 2.95, 3.00, 3.08, 3.46, 5.60, 5.75, 6.17, 6.35, 6.88, 7.30, 7.55, 8.25, 8.75, 9.70.

Analysis: Calcd. for $C_{28}H_{38}N_2O_5$: C, 65.35; H, 7.44; N, 5.44. Found: C, 65.24; H, 7.37; N, 5.32.

EXAMPLE 7

Mixed diastereomers of 9-acetamido-1-acetoxy-5,6,6a-beta,7,8,9,10,10a-alpha-octahydro-6-beta-methyl-3-(5-phenyl-2-pentyloxy)benzo[c]quinoline The mixed diastereomers of 9-amino-1-acetoxy-5,6,6a-beta,7,8,9,10,10a-alpha-octahydro-6-beta-methyl-3-(5-phenyl-2-pentyloxy)benzo[c]quinoline, 336 mg. (0.77 mmole) was dissolved in 10 ml. of methylene chloride and 0.804 ml. (10 mmole) of pyridine was added. The solution was cooled to −20° C., and a solution of 0.075 ml. (0.77 mmole) acetic anhydride in 5 ml. of methylene chloride was added dropwise over five minutes. The mixture was allowed to warm to 5° C., poured into a mixture of ice water and methylene chloride (20 ml. each) and the product isolated as described in Example 6 to provide 315 mg. of amorphous material (86%). Mass spectrum (m/e): 478 M+, 433, 376, 290, 230, 215, 176, 91; infrared spectrum (KBr) microns: 2.96, 3.43, 3.51, 5.64, 5.72, 6.04, 6.15, 7.28, 8.20 (broad), 8.63.

Analysis: Calcd for $C_{29}H_{38}N_2O_4$: C, 72.77; H, 8.00; N, 5.85. Found: C, 72.58; H, 7.95; N, 5.71.

EXAMPLE 8 dl-9-alpha-Acetamido-1-acetoxy-5,6,6a-beta,7,8,9,10,-10a-alpha-octahydro-6-beta-methyl-3-(5-phenyl-2-pentyloxy)benzo[c]quinoline and the 9-beta-acetylamino diastereomer The procedure of Example 7 was repeated on a 3.4 millimolar scale to provide 1.577 g. of mixed diasteomers. The crude mixture was digested in ethyl ether, filtered and the insoluble material washed with ether and dried at room temperature, 0.05 mm. for 20 hours, to afford 964 mg. of the 9-alpha-acetamido isomer, m.p. 154°–155° C. Mass spectrum (m/e): 478 M+, 377, 360, 290, 230, 91; infrared spectrum (KBr) microns: 2.94, 3.00, 3.42, 5.72, 6.00, 6.14, 6.24, 6.52, 7.27, 8.08, 8.12, 8.64.

Analysis: Calcd. for $C_{29}H_{38}N_2O_4$: C, 72.77; H, 8.00; N, 5.85. Found: C, 72.70; H, 7.87; N, 5.85.

Evaporation of the mother liquor gave a white foam which was identified as a mixture of the 9-alpha-acetamido and 9-beta-acetamido diastereomers. This was purified by column chromatography on 75 g. of silica gel eluting with 9:1 by volume ethyl ether/ethyl acetate. The fractions containing the less polar 9-beta-acetyl-amino isomer were combined, evaporated and dried to provide 58 mg. of product which was identified as the free base of the product obtained in Example 2 as determined by its $^1$H-NMR spectrum in $CDCl_3$, mass spectrum and infrared spectrum (KBr).

Analysis: Calcd. for $C_{29}H_{38}N_2O_4$: C, 72.77; H, 8.00; N, 5.85. Found: C, 72.35; H, 8.15; N, 5.88.

EXAMPLE 9 dl-9-alpha-Acetamido-1-acetoxy-5,6,6a-beta,7,8,9,10,-10a-alpha-octahydro-5,6-beta-dimethyl-3-(5-phenyl-2-pentyloxy)benzo[c]quinoline hydrochloride To a mixture of 475 mg. of 5% palladium-on-carbon and 10 ml. of methanol swept with nitrogen, was added a solution of 475 mg. (0.99 mmole) of dl-9-alpha-acetamido-1-acetoxy-5,6,6a-beta,7,8,9,10,10a-alpha-6-beta-methyl-3-(5-phenyl-2-pentyloxy)benzo[c]quinoline in 10 ml. of methanol, 7.5 ml. of 37% formaldehyde and 0.5 ml. acetic acid. The resulting mixture was hydrogenated at atmospheric temperature and pressure. The theoretical amount of hydrogen (22 ml.) was taken up in 20 minutes. The mixture was filtered and the filtrate poured into a mixture of 100 ml. water and 50 ml. of methylene chloride. The aqueous phase was separated, extracted with 50 ml. of methylene chloride and the combined organic layers were washed with 50 ml. each of sodium bicarbonate solution, water and brine and dried over anhydrous magnesium sulfate. Evaporation of the dried extract afforded a colorless oil which was purified by chromatography on 60 g. of silica gel, eluting with 1.1 by volume toluene/ethyl ether. The product-containing fractions were combined and evaporated to afford a colorless oil which was dissolved in 20 ml. of ether and filtered. The filtrate was treated with an ethyl acetate solution of hydrogen chloride until the mixture was acidic to litmus paper. The precipitated product was collected by filtration and dried at 24° C. (0.05 mm.) for two days, m.p. 115°–116° C. Yield 361 mg. (75.7%). Mass spectrum (m/e): 492 M+, 478, 391, 375, 286, 244, 230, 190; infrared spectrum (KBr) microns: 2.95, 3.45, 4.20 (broad), 5.65, 6.00, 6.14, 6.52, 7.30, 8.35.

Analysis: Calcd. for $C_{30}H_{40}N_2O_4$ HCl: C, 68.08; H, 7.81; N, 5.30. Found: C, 65.97; H, 7.88; N, 5.28.

EXAMPLE 10

Diastereomeric dl-trans-9-beta-Acetamido-1-acetoxy-5,6,6a-beta,7,8,9,10,10a-alpha-octahydro-5,6-beta-dimethyl-3-(1-beta-methyl-4-phenylbutoxy)benzo[c]quinoline hydrochloride and its mixture with the -3-(1-alpha-methyl-4-phenylbutoxy)-diastereomer A mixture of 741 mg. of dl-trans-9-beta-acetamido-1-acetoxy-5,6,6a-beta,7,8,9,10,10a-alpha-octahydro-6-beta-methyl-3-(5-phenyl-2-pentyloxy)benzo[c]quinoline, 25 ml. of freshly distilled tetrahydrofuran, 7.5 ml. of 37% formaldehyde, 550 mg. of 5% palladium-on-carbon and 0.55 ml. of acetic acid was hydrogenated at 40 psi (2.81 kg./cm.$^2$) for one hour. The catalyst was removed by filtration, washing with ethyl acetate. The filtrate was washed with 4×150 ml. of sodium bicarbonate solution, 2×150 ml. water, 200 ml. brine, dried (MgSO$_4$) and the solvent evaporated in vacuo to obtain 800 mg. of colorless foam which contained a mixture of racemic diastereomers of 9-beta-acetamido-1-acetoxy-5,6,6a-beta,7,8,9,10,10a-alpha-octahydro-5,6-beta-dimethyl-3-(1-methyl-4-phenylbutoxy)benzo[c]quinoline. This was chromatographed on a column of silica gel (40 g.) eluting initially with 1:1 by volume ethyl ether/toluene. Fractions of 15 ml. were collected. After 170 fractions were collected, a mixture of ethyl acetate/toluene (1:1 by volume) was employed. A total of 350 fractions were collected.

A. Fractions 171–300 were combined and concentrated to dryness in vacuo to obtain 445 mg. of colorless oil. Addition of ethyl ether to the oil afforded 175 mg. of the free base of the 3-(1-beta-methyl-4-phenylbutoxy)diastereomer; m.p. 120°–121° C. The free base was dissolved in 20 ml. of ethyl acetate and saturated with dry hydrogen chloride. Addition of ether caused precipitation of the hydrochloride salt, 190 mg., m.p. 105°–120° C. This was shown to be the -3-(1-beta-methyl-4-phenylbutoxy)diastereomer (racemic) by $^1$H-NMR spectroscopy.

Analysis: Calcd. for $C_{30}H_{40}O_4N_2$·HCl; C, 68.11; H, 7.81; N, 5.30. Found: C, 67.52; H, 8.01; N, 5.26.

B. The ethereal mother liquor from above was evaporated to dryness to afford 300 mg. of oil. This was dissolved in ether (50 ml.) and the solution saturated with dry hydrogen chloride to give 240 mg. of hydrochloride salt of mixed [3-(1-alpha-methyl- and 1-beta-methyl-4-phenylbutoxy)] diastereomers of the title compound, m.p. 105°–120° C. $^1$H-NMR spectroscopy showed it to be a 50:50 mixture of the two racemic diastereomers.

Analysis: Calcd. for $C_{30}H_{40}O_4N_2$ HCl: C, 68.11; H, 7.81; N, 5.30. Found: C, 67.50; H, 7.58; N, 5.24.

The structure of both of the above isolates was confirmed by mass spectroscopy.

EXAMPLE 11

[3(1R),6S,6aR,9R,10aR]-9-Acetamido-1-acetoxy-5,6,6a,7,8,9,10,10a-octahydro-6-methyl-3-(1-methyl-4-phenylbutoxy)benzo[c]quinoline hydrochloride;

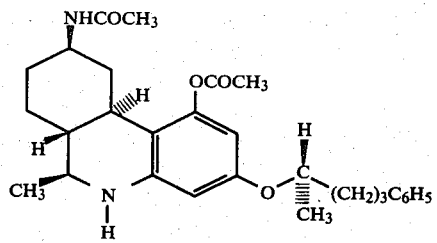

A. (−)[3(1R),6S,6aR]-1-Hydroxy-5,6,6a,7-tetrahydro-6-methyl-3-(1-methyl-4-phenylbutoxy)benzo[c]quinoline-9-(8H)one,$[\alpha]_D^{25}$ −396.37 (c=1, methanol), 0.776 g. (1.98 mmole) was dissolved in 3 ml. of pyridine and 0.206 g. (2.97 mmole) of hydroxylamine hydrochloride was added. The mixture was stirred at room temperature overnight, poured into 50 ml. of ethyl acetate and the resulting solution washed with 0.5 N hydrochloric acid (6×30 ml.), brine (30 ml.) and dried over anhydrous magnesium sulfate. The solvent was evaporated in vacuo to obtain the corresponding oxime which was used immediately in the next step.

B. The oxime thus obtained was dissolved in 25 ml. of methanol; 0.3 g. of 5% palladium-on-carbon was added and the mixture hydrogenated at 50 psi (3.52 kg./cm.$^2$) overnight. The catalyst was removed by filtration and the filtrate evaporated in vacuo. The residue was dissolved in 15 ml. methylene chloride; 0.464 g. (4.55 mmole) triethylamine was added and the solution cooled to 0° C. 0.555 g. (4.55 mmole) 4-dimethylaminopyridine and 0.46 g. (4.55 mmole) of acetic anhydride were added and the resulting mixture stirred at 0° C. under a nitrogen atmosphere for one hour. The mixture was poured into 50 ml. methylene chloride, washed with 0.5 N hydrochloric acid (5×20 ml.), water (20 ml.), brine (20 ml.) and dried over anhydrous magnesium sulfate. The dried solution was evaporated in vacuo, the residue placed on a column of silica gel (50 g., 0.63–0.2 microns) and eluted with 97:3 by volume ethyl ether/methanol. The product fractions were combined and evaporated to a small volume in vacuo. Hydrogen chloride was passed through the concentrate to precipitate 89 mg. of solid product, m.p. 138°–142° C.

Analysis: Calcd. for $C_{29}H_{38}N_2O_4$: C, 67.62; H, 7.63; N, 5.44. Found: C, 68.05; H, 7.55; N, 5.45.

EXAMPLE 12

(+)[3(1R),6S,6aR,9R,10aR]-9-Acetamido-1-acetoxy-5,6,6a,7,8,9,10,10a-octahydro-5,6-dimethyl-3-(1-methyl-4-phenylbutoxy)benzo[c]quinoline;

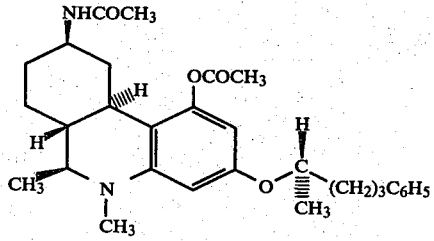

Hydrogenation of a mixture of 0.71 g. (1.48 mmole) of [3(1R),6S,6aR,9R,10aR]-9-acetamido-1-acetoxy-5,6,6a,7,8,9,10,10a-octahydro-6-methyl-3-(1-methyl-4-phenylbutoxy)benzo[c]quinoline, 0.71 g. of 5% Pd/C, 12.0 g. of 37% formaldehyde and 0.7 ml. of acetic acid by the procedure of Example 9 afforded 750 mg. of crude oil. This was purified by column chromatography on 35 g. of 0.04–0.063 micron silica gel eluting with ethyl ether containing 2% by volume of methanol. The product fractions yielded 0.27 g. (37%) of the desired N-methyl compound as a colorless solid, m.p. 120°–122° C. Mass spectrum (m/e) 492 M+, 304, 230; infrared spectrum (KBr) microns: 3.02, 3.41, 5.71, 6.15, 8.17, 13.41, 14.36. $[\alpha]_D^{25}$ +154.88 (c=0.1, methanol).

Analysis: Calcd. for $C_{30}H_{40}N_2O_4$: C, 73.14; H, 8.18; N, 5.69. Found: C, 72.67; H, 8.00; N, 5.58.

EXAMPLE 13 dl-trans-9-Formamido-1-hydroxy-3-(2-heptyloxy)-5,6,6a,7,8,9,10,10a-octahydrobenzo[c]quinoline A. dl-1-Acetoxy-3-(2-heptyloxy)-5,6,6a-beta,7,10,10a-alpha-hexahydrobenzo[c]quinoline-9-(8H)one, m.p. 65.5°–68° C. (prepared by the method of Belgium Patent No. 854,655), 3.73 g. (0.01 mole) and 1.0 g. (0.014 mole) of hydroxylamine hydrochloride are dissolved in 70 ml. of ethanol and 10 ml. of water. The mixture is stirred while 3.8 ml. of 5 N sodium hydroxide is added in one portion. The resulting mixture is heated at reflux for 30 minutes, cooled, poured onto ice and extracted with ethyl ether. The extracts are washed with water, dried over anhydrous magnesium sulfate and evaporated to dryness to provide dl-trans-1-hydroxy-3-(2-heptyloxy)-5,6,6a,7,10,10a-hexahydrobenzo[c]quinoline-9(8H)oxime.

B. A solution of 1.94 g. (5 mmole) of dl-trans-1-hydroxy-3-(2-heptyloxy)-5,6,6a,7,10,10a-hexahydrobenzo[c]quinoline-9(8H)oxime in 100 ml. of ethanol and 25 ml. of anhydrous ammonia and containing 1 g. of Raney nickel is hydrogenated at 100° C. and 50 atmospheres pressure for four hours. The resulting mixture is cooled to room temperature, filtered to remove catalyst and the filtrate evaporated in vacuo. The residue is dissolved in ethyl formate (75 ml.) and the solution heated at reflux overnight. The mixture is evaporated to dryness to obtain the desired product as a mixture of diastereomers which are separated, if desired, by column chromatography on silica gel.

Alternatively, the corresponding 9-acetamido-1-hydroxybenzo[c]quinoline is obtained when the residue obtained upon hydrogenation is acetylated with acetic anhydride by the procedure of Example 7. When a molar excess of acetic anhydride is employed, the corresponding 9-acetamido-1-acetoxybenzo[c]quinoline is obtained.

EXAMPLE 14 dl-9-Amino-1-hydroxy-6-benzyl-6-methyl-3-(8-phenyl-4-thiaoctyl)-5,6,6a,7,8,9,10,10a-octahydrobenzo[c]quinoline A mixture of 5.53 g. (0.01 mole) of dl-1-acetoxy-6-benzyl-6-methyl-3-(8-phenyl-4-thiaoctyl)-5,6,6a,7,10,-10a-hexahydrobenzo[c]quinoline-9(8H)one, 5 ml. formamide and 10 ml. formic acid is heated at reflux under a nitrogen atmosphere while removing water as it forms in the reaction. Additional formic acid is added as required to control deposition of ammonium carbonate in the condenser. When the reaction temperature reaches 195° C., the mixture is cooled, diluted with water and extracted with ethyl acetate. The extract is evaporated to dryness, 5 ml. of concentrated hydrochloric acid is added and the mixture boiled for three hours, cooled, washed with ethyl ether. The aqueous phase is made alkaline with sodium hydroxide solution, extracted with ether and the extracts dried over anhydrous magnesium sulfate. The solvent is evaporated to afford the title compound as a mixture of isomers.

EXAMPLE 15 dl-9-Amino-1-hydroxy-6-methyl-3-(3-methyl-2-octylthio)-5,6,6a,7,8,9,10,10a-octahydrobenzo[c]quinoline To 10 ml. of dry methanol is added 1.51 g. (3.1 mmole) of dl-1-hydroxy-6-methyl-3-(3-methyl-2-octylthio)-5,6,6a,7,10,10a-hexahydrobenzo[c]quinoline-9(8H)one, 2.39 g. (31 mmole) ammonium acetate and 0.272 g. (4.34 mmole) sodium cyanoborohydride, and the resulting mixture is heated at reflux for two days. The resulting mixture is acidified to pH 2 with hydrochloric acid and evaporated to dryness in vacuo. The residue is taken up in water, washed with ethyl ether, the aqueous phase adjusted to pH 12 with sodium hydroxide solution and extracted with ethyl ether. The extracts are washed with brine, dried over anhydrous magnesium sulfate and evaporated to dryness to provide the title compound as a mixture of diastereomers which are separated, if desired, by fractional crystallization followed by column chromatography on silica gel.

When the starting 1-hydroxy-9-keto compound is replaced by an equimolar amount of the corresponding 1-butyryloxy-9-keto-compound in the above procedure and after the reflux period, the reaction mixture is concentrated to a small volume, 200 ml. ethyl ether is added, the resulting mixture washed with ice water and cold brine, the ether extract dried (MgSO4) and evaporated to dryness, dl-9-amino-1-butyryloxy-6-methyl-3-(3-methyl-2-octylthio)-5,6,6a,7,8,9,10,10a-octahydrobenzo[c]quinoline is obtained. It is purified by column chromatography on silica gel.

EXAMPLE 16

The 9-amino compounds provided in Examples 14 and 15 are acylated or sulfonylated by the procedures of Examples 6 and 7 to provide the corresponding 9-acylamino or 9-sulfonylamino compounds employing the following reagents in place of acetic anhydride or methanesulfonyl chloride:
($CH_3CH_2CO$)$_2$O
$CH_3(CH_2)_2COCl$
$CH_3(CH_2)_4COBr$
$CH_2$=$CHCOCl$
$CH_3CH$=$CHCOCl$
$CH_2$=$CH(CH_2)_4COCl$
$CH$≡$CCOCl$
$CH_3C$≡$CCH_2COCl$
$CH$≡$C(CH_2)_4COCl$
($CF_3CO$)$_2$O
$C_6H_5CH_2COBr$

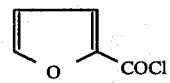

-continued

[structure: thiophene-COCl]

[structure: pyridine-3-COCl]

4-NH$_2$C$_6$H$_4$COCl HCl
2-FC$_6$H$_4$COCl
3-BrC$_6$H$_4$COBr
2-CH$_3$C$_6$H$_4$COCl
4-CH$_3$OC$_6$H$_4$COCl
3-ClC$_6$H$_4$COCl

CH$_3$CH$_2$SO$_2$Cl
CH$_3$(CH$_2$)$_3$SO$_2$Cl
CH$_3$(CH$_2$)$_4$SO$_2$Cl
C$_6$H$_5$SO$_2$Cl
2-NH$_2$C$_6$H$_4$SO$_2$Br HBr
4-FC$_6$H$_4$SO$_2$Cl
2-ClC$_6$H$_4$SO$_2$Cl
4-BrC$_6$H$_4$SO$_2$Cl
4-CH$_3$C$_6$H$_4$SO$_2$Cl
2-CH$_3$OC$_6$H$_4$SO$_2$Br

EXAMPLE 17

Employing the procedures of Examples 5–16, the following compounds of formula (I) are prepared in like manner using the appropriate reagents starting from the corresponding compound of formula (II) by reductive amination and subsequent acylation or sulfonylation.

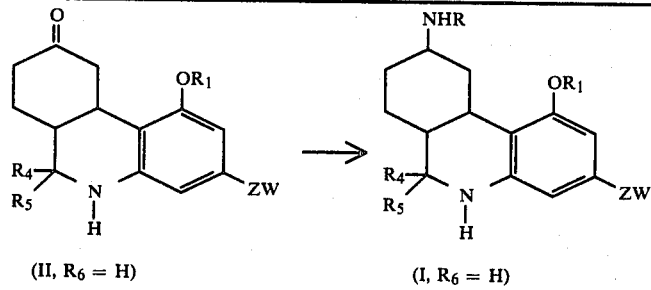

(II, R$_6$ = H) → (I, R$_6$ = H)

In the compounds of formula (I) tabulated below, Z is:
(a) alkylene or
(b) —(alk$_1$)$_m$—X—(alk$_2$)$_n$—, each of which is defined above. (CH$_2$)$_3$S corresponds to —(alk$_1$)—X—; —S(CH$_2$)$_3$ corresponds to —X—(alk$_2$).

| R | R$_1$ | R$_4$ | R$_5$ | Z | W |
|---|---|---|---|---|---|
| CH$_3$CO | CH$_3$CO | H | H | CH(CH$_3$)(CH$_2$)$_3$ | C$_6$H$_5$ |
| CH$_3$CH$_2$CO | CH$_3$CH$_2$CO | C$_2$H$_5$ | H | CH(CH$_3$)(CH$_2$)$_3$ | C$_6$H$_5$ |
| CH$_3$(CH$_2$)$_4$CO | CH$_3$CO | H | H | (CH$_2$)$_2$CH(C$_2$H$_5$) | C$_6$H$_5$ |
| CH$_3$CH=CHCO | C$_6$H$_5$CO | C$_2$H$_5$ | H | (CH$_2$)$_4$ | C$_6$H$_5$ |
| CH$_2$=CHCO | n-C$_4$H$_9$CO | H | H | CH(CH$_3$)(CH$_2$)$_7$ | C$_6$H$_5$ |
| CH$_3$CH=CHCH$_2$CO | CH$_3$CO | H | H | CH$_2$ | C$_6$H$_5$ |
| n-C$_4$H$_9$CO | n-C$_4$H$_9$CO | C$_2$H$_5$ | H | CH(CH$_3$)CH$_2$ | 4-FC$_6$H$_4$ |
| CH≡CCO | CH$_3$CO | C$_2$H$_5$ | H | CH(CH$_3$)(CH$_2$)$_2$ | 4-ClC$_6$H$_4$ |
| CH$_3$C≡CCH$_2$CO | CH$_3$CO | H | H | (CH$_2$)$_3$ | C$_5$H$_9$ |
| CH≡C(CH$_2$)$_4$CO | CH$_3$CH$_2$CO | CH$_3$ | CH$_3$ | CH(CH$_3$)(CH$_2$)$_3$ | C$_6$H$_5$ |
| CF$_3$CO | HCO | H | H | CH(CH$_3$)CH$_2$ | C$_3$H$_5$ |
| C$_6$H$_5$CO | C$_6$H$_5$CO | CH$_3$ | H | CH(CH$_3$)(CH$_2$)$_5$ | C$_6$H$_{11}$ |
| 2-Furoyl | CH$_3$CO | H | H | (CH$_2$)$_8$ | C$_6$H$_{11}$ |
| 3-Furoyl | C$_6$H$_5$CO | H | H | (CH$_2$)$_3$ | 2-pyridyl |
| 2-Thenyl | CH$_3$CO | C$_2$H$_5$ | H | CH(CH$_3$)(CH$_2$)$_2$ | 3-pyridyl |
| 3-Thenyl | CH$_3$CO | CH$_3$ | H | CH(CH$_3$)CH(C$_2$H$_5$)CH$_2$ | 4-pyridyl |
| 2-pyridyl—CO | CH$_3$CO | CH$_3$ | H | CH(C$_2$H$_5$)(CH$_2$)$_2$ | 2-piperidyl |
| 4-pyridyl—CO | C$_6$H$_5$CO | CH$_3$ | H | CH(CH$_3$)(CH$_2$)$_2$CH(CH$_3$) | 4-piperidyl |
| 4-NH$_2$C$_6$H$_4$CO | C$_6$H$_5$CO | CH$_3$ | H | CH(CH$_3$)(CH$_2$)$_2$ | C$_7$H$_{13}$ |
| 2-FC$_6$H$_4$CO | CH$_3$CO | CH$_3$ | H | CH(CH$_3$)CH(CH$_3$)(CH$_2$)$_5$ | H |
| 3-ClC$_6$H$_4$CO | CH$_3$CO | H | H | CH$_2$ | H |
| 4-BrC$_6$H$_4$CO | CH$_3$CO | CH$_3$ | H | (CH$_2$)$_6$ | CH$_3$ |
| 3-CH$_3$C$_6$H$_4$CO | C$_6$H$_5$CO | CH$_3$ | H | (CH$_2$)$_3$ | H |
| 4-CH$_3$OC$_6$H$_4$CO | CH$_3$CO | H | H | CH(CH$_3$) | C$_6$H$_{11}$ |
| CH$_3$SO$_2$ | CH$_3$CO | H | H | (CH$_2$)$_9$—O— | C$_6$H$_5$ |
| C$_2$H$_5$SO$_2$ | CH$_3$CO | CH$_3$ | H | (CH$_2$)$_3$—O— | C$_6$H$_{11}$ |
| n-C$_3$H$_7$SO$_2$ | CH$_3$CO | C$_2$H$_5$ | H | (CH$_2$)$_3$—O— | C$_4$H$_7$ |
| i-C$_3$H$_7$SO$_2$ | HCO | CH$_3$ | H | (CH$_2$)$_3$—O— | 4-(4-FC$_6$H$_4$)C$_6$H$_{10}$ |
| n-C$_4$H$_9$SO$_2$ | CH$_3$CO | C$_2$H$_5$ | H | (CH$_2$)$_3$—O—(CH$_2$)$_2$ | 4-ClC$_6$H$_4$ |
| Sec-C$_4$H$_9$SO$_2$ | HCO | CH$_3$ | H | (CH$_2$)$_3$—O—CH(CH$_3$) | 4-piperidyl |
| i-C$_4$H$_9$SO$_2$ | CH$_3$CO | CH$_3$ | H | (CH$_2$)$_3$—O—CH(CH$_3$)(CH$_2$)$_2$ | C$_6$H$_5$ |
| n-C$_5$H$_{11}$SO$_2$ | CH$_3$CO | H | H | (CH$_2$)$_3$—O—CH(CH$_3$)(CH$_2$)$_2$ | CH$_3$ |
| C$_6$H$_5$SO$_2$ | CH$_3$CO | CH$_3$ | H | CH(CH$_3$)(CH$_2$)$_2$—O—CH$_2$ | CH$_3$ |
| 3-NH$_2$C$_6$H$_4$SO$_2$ | C$_6$H$_5$CO | C$_2$H$_5$ | H | (CH$_2$)$_4$—O—(CH$_2$)$_5$ | 4-pyridyl |
| 4-FC$_6$H$_4$SO$_2$ | C$_6$H$_5$CO | H | H | CH(CH$_3$)(CH$_2$)$_3$—O— | 2-(4-FC$_6$H$_5$)C$_5$H$_8$ |
| 4-ClC$_6$H$_4$SO$_2$ | CH$_3$CO | H | H | CH(C$_2$H$_5$)(CH$_2$)$_2$—O—(CH$_2$)$_4$ | C$_6$H$_5$ |
| 3-BrC$_6$H$_4$SO$_2$ | CH$_3$CO | CH$_3$ | H | CH(C$_2$H$_5$)(CH$_2$)$_2$—O—CH(CH$_3$) | 4-piperidyl |
| 4-CH$_3$C$_6$H$_4$SO$_2$ | CH$_3$CO | H | H | CH(C$_2$H$_5$)(CH$_2$)$_2$O(CH$_2$)$_2$CH(CH$_3$) | C$_7$H$_{13}$ |
| 2-CH$_3$OC$_6$H$_4$SO$_2$ | CH$_3$CO | H | H | CH(C$_2$H$_5$)(CH$_2$)$_2$—O— | 2-(4-ClC$_6$H$_4$)C$_7$H$_{12}$ |
| C$_6$H$_5$SO$_2$ | C$_6$H$_5$CH$_2$ | H | H | (CH$_2$)$_3$—S— | C$_6$H$_5$ |

-continued

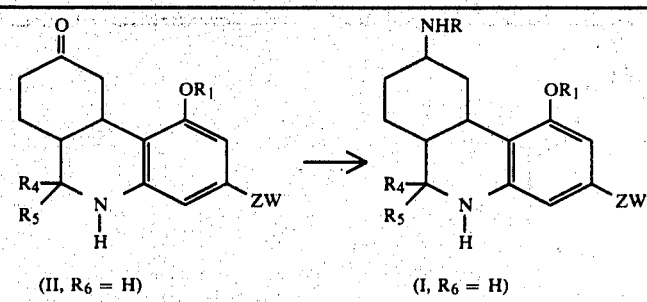

In the compounds of formula (I) tabulated below, Z is:
(a) alkylene or
(b) $-(alk_1)_m-X-(alk_2)_n-$, each of which is defined above. $(CH_2)_3S$ corresponds to $-(alk_1)-X-$; $-S(CH_2)_3$ corresponds to $-X-(alk_2)$.

| R | $R_1$ | $R_4$ | $R_5$ | Z | W |
|---|---|---|---|---|---|
| $CH_3SO_2$ | $C_6H_5CH_2$ | $C_2H_5$ | H | $(CH_2)_3-S-CH_2$ | $4-FC_6H_4$ |
| $CH_3SO_2$ | $CH_3CO$ | $CH_3$ | H | $(CH_2)_3-S-$ | $C_5H_9$ |
| $CH_3SO_2$ | $(CH_3)_2NCO$ | $C_2H_5$ | H | $(CH_2)_3-S-(CH_2)_2$ | $CH_3$ |
| $CH_3SO_2$ | $(C_4H_9)_2NCH_2CO$ | $CH_3$ | H | $CH(CH_3)(CH_2)_2-S-$ | 4-piperidyl |
| $C_6H_5SO_2$ | $(CH_3)_2N(CH_3)_4CO$ | $CH_3$ | H | $CH(CH_3)(CH_2)_2-S-$ | $4-(C_6H_5)C_6H_{10}$ |
| $C_6H_5SO_2$ | $(C_4H_9)_2NCO$ | $CH_3$ | H | $CH(C_2H_5)(CH_2)_2S(CH_2)_2CHCH_3$ | $CH_3$ |
| $C_6H_5CO$ | $(C_2H_5)_2NCO$ | H | H | $CH(CH_3)(CH_2)_3S(CH_2)_4$ | $4-FC_6H_4$ |
| $C_6H_5CO$ | ⟨N-CO⟩ (pyrrolidinyl) | $CH_3$ | H | $CH(CH_3)CH_2O(CH_2)_6$ | $C_6H_5$ |
| $C_6H_5CO$ | ⟨N-CO⟩ (piperidinyl) | $C_6H_5CH_2$ | $C_2H_5$ | $CH_2CH(CH_3)O(CH_2)_2$ | $4-FC_6H_4$ |
| $CH_3CO$ | ⟨O⟩⟨N-CO⟩ (morpholinyl) | $C_6H_5(CH_2)_4$ | $CH_3$ | $C(CH_3)_2(CH_2)_6$ | H |
| $CH_3SO_2$ | HCO | $CH_3$ | $CH_3$ | $CH(CH_3)(CH_2)_3$ | $C_6H_5$ |
| $CH_3SO_2$ | HCO | $C_2H_5$ | $C_2H_5$ | $CH(CH_3)(CH_2)_3$ | $C_6H_5$ |
| $CH_3SO_2$ | HCO | $C_2H_5$ | $CH_3$ | $CH(CH_3)(CH_2)_4$ | $C_6H_5$ |
| $CH_3SO_2$ | HCO | $C_6H_5CH_2$ | H | $(CH_2)_3$ | $C_6H_5$ |
| $CH_3SO_2$ | $CH_3CO$ | $C_6H_5(CH_2)_4$ | H | $(CH_2)_2CH(C_2H_5)$ | $C_6H_5$ |
| $CH_3SO_2$ | $CH_3CO$ | $CH_3$ | $CH_3$ | $C(CH_3)_2$ | $C_6H_5$ |
| $CH_3CO$ | $CH_3CO$ | $CH_3$ | $CH_3$ | $CH(CH_3)(CH_2)_7$ | $C_6H_5$ |
| $CH_3CO$ | $CH_3CO$ | $n-C_4H_9$ | H | $CH_2$ | $C_6H_5$ |
| $CH_3CO$ | $CH_3CO$ | $n-C_6H_{13}$ | $CH_3$ | $CH(CH_3)CH_2$ | $4-FC_6H_4$ |
| $CH_3CO$ | $CH_3CO$ | $C_6H_5(CH_2)_2$ | H | $CH(CH_3)(CH_2)_2CH(CH_3)$ | $C_6H_5$ |
| $CH_3CO$ | $CH_3CO$ | $C_6H_5(CH_2)_3$ | H | $CH(CH_3)(CH_2)_5$ | $C_6H_{11}$ |
| $CH_3CO$ | $CH_3CO$ | $n-C_4H_9$ | $CH_3$ | $(CH_2)_4$ | $C_3H_5$ |
| $CH_3CO$ | $CH_3CO$ | $CH_3$ | $CH_3$ | $(CH_2)_9$ | $C_6H_{11}$ |
| $CH_3CO$ | $CH_3CO$ | $C_6H_5CH_2$ | $CH_3$ | $(CH_2)_3$ | 4-pyridyl |
| $CH_3CO$ | $CH_3CO$ | $C_2H_5$ | $C_2H_5$ | $(CH_2)_4$ | 3-pyridyl |
| $CH_3CO$ | $C_6H_5CO$ | $n-C_5H_{11}$ | H | $CH(C_2H_5)(CH_2)_3$ | 3-pyridyl |
| $CH_3CO$ | $C_6H_5CO$ | $i-C_3H_7$ | H | $CH(CH_3)(CH_2)_2$ | 4-piperidyl |
| $C_6H_5CO$ | $C_6H_5CO$ | $CH_3$ | $CH_3$ | $CH(CH_3)(CH_2)_2$ | $C_7H_{13}$ |
| $C_6H_5CO$ | $C_6H_5CO$ | $CH_3$ | $CH_3$ | $(CH_2)_3-O-$ | $C_6H_5$ |
| $C_6H_5CO$ | $C_6H_5CO$ | $CH_3$ | $CH_3$ | $(CH_2)_3-O-$ | $C_4H_7$ |
| $C_6H_5CO$ | $C_6H_5CO$ | $C_6H_5CH_2$ | H | $(CH_2)_3-O-$ | $CH_3$ |
| $C_6H_5CO$ | $CH_3CO$ | $CH_3$ | $CH_3$ | $(CH_2)_3-O-$ | $4-(4-ClC_6H_4)C_6H_{10}$ |
| $C_6H_5CO$ | ⟨O⟩⟨NCH_2CO⟩ (morpholinyl-CH_2CO) | $C_2H_5$ | $C_2H_5$ | $(CH_2)_3-O-(CH_2)_2$ | $4-ClC_6H_4$ |
| $CH_3CO$ | ⟨N-(CH_2)_4CO⟩ (pyrrolidinyl) | $CH_3$ | $CH_3$ | $(CH_2)_3-O-CH(CH_3)$ | 4-piperidyl |

-continued

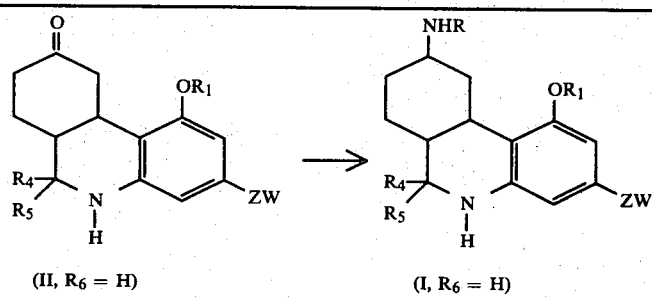

(II, $R_6$ = H) → (I, $R_6$ = H)

In the compounds of formula (I) tabulated below, Z is:
(a) alkylene or
(b) $-(alk_1)_m-X-(alk_2)_n-$, each of which is defined above. $(CH_2)_3S$ corresponds to $-(alk_1)-X-$; $-S(CH_2)_3$ corresponds to $-X-(alk_2)$.

| R | $R_1$ | $R_4$ | $R_5$ | Z | W |
|---|---|---|---|---|---|
| $CH_3CO$ | ⬡N($CH_2)_2CO$ | n-$C_5H_{11}$ | H | $CH(CH_3)(CH_2)_2-O-$ | $C_6H_5$ |
| $CH_3CO$ | ⬠N-CO | $CH_3$ | $CH_3$ | $CH(CH_3)(CH_2)_2-O-CH_2$ | $CH_3$ |
| $CH_3CO$ | ⬠NCO | $CH_3$ | $CH_3$ | $CH(CH_3)(CH_2)_2-O-(CH_2)_4$ | $C_6H_5$ |
| $CH_3CO$ | $CH_3N$⬡N-CO | $CH_3$ | $CH_3$ | $CH(CH_3)(CH_2)_2-O-CH(CH_3)$ | $C_7H_{13}$ |
| $CH_3CO$ | n-$C_4H_9$-N⬡NCO | $CH_3$ | $CH_3$ | $(CH_2)_4O-$ | $C_6H_5$ |
| $CH_3CO$ | $C_2H_5N$⬡N-CO | $C_2H_5$ | $C_2H_5$ | $(CH_2)_4OCH(CH_3)CH_2$ | 3-piperidyl |
| $CH_3CO$ | $CH_3CO$ | $C_2H_5$ | $CH_3$ | $(CH_2)_4-O-CH_2$ | 4-$FC_6H_4$ |
| $CH_3CO$ | $CH_3CO$ | n-$C_3H_7$ | H | $CH(CH_3)(CH_2)_3-O-$ | 2-(4-$FC_6H_4)C_5H_8$ |
| $CH_3CO$ | $CH_3CO$ | $CH_3$ | $CH_3$ | $(CH_2)_3-S-$ | $C_6H_5$ |
| $CH_3CO$ | $CH_3CO$ | $C_2H_5$ | $C_2H_5$ | $(CH_2)_3-S-CH_2$ | 4-$FC_6H_4$ |
| $CH_3CO$ | $CH_3CO$ | $CH_3$ | $CH_3$ | $(CH_2)_3-S-$ | $C_5H_9$ |
| $CH_3CO$ | $CH_3CO$ | $C_6H_5CH_2$ | $CH_3$ | $(CH_2)_3-S-(CH_2)_4$ | $C_6H_5$ |
| $CH_3CO$ | $CH_3CO$ | $CH_3$ | $CH_3$ | $CH(CH_3)(CH_2)_2-S-(CH_2)_4$ | 4-pyridyl |
| $CF_3CO$ | $CH_3CO$ | $C_2H_5$ | $C_2H_5$ | $CH(C_2H_5)(CH_2)_2-SO$ | $C_6H_{11}$ |
| $CF_3CO$ | $CH_3CO$ | n-$C_6H_{13}$ | H | $CH(C_2H_5)(CH_2)_2-S-CH(CH_3)$ | 4-$ClC_6H_4$ |
| $CF_3CO$ | $CH_3CO$ | n-$C_4H_9$ | $CH_3$ | $CH(CH_3)(CH_2)_3-S-(CH_2)_4$ | 4-$FC_6H_4$ |
| $CF_3CO$ | $CH_3CO$ | $CH_3$ | $CH_3$ | $CH(CH_3)CH_2-O-(CH_2)_6$ | $C_6H_5$ |
| $CF_3CO$ | $CH_3CO$ | $C_2H_5$ | $C_2H_5$ | $C(CH_3)_2(CH_2)_6$ | H |
| $CF_3CO$ | $CH_3CO$ | H | H | $OCH_2$ | H |
| $CF_3CO$ | $CH_3CO$ | $CH_3$ | H | $O(CH_2)_2$ | H |
| $CF_3CO$ | $CH_3CO$ | $CH_3$ | H | $O(CH_2)_6$ | H |
| $CF_3CO$ | $CH_3CO$ | $CH_3$ | H | $O(CH_2)_9$ | H |
| $CF_3CO$ | $CH_3CO$ | $C_2H_5$ | H | $OCH_2$ | 4-$ClC_6H_4$ |
| $CH_3SO_2$ | $CH_3CO$ | $CH_3$ | H | $OCH(CH_3)(CH_2)_3$ | $C_6H_5$ |
| $CH_3SO_2$ | $CH_3CO$ | H | H | $OCH(CH_3)CH(CH_3)(CH_2)_4$ | $CH_3$ |
| $CH_3SO_2$ | $CH_3CO$ | $CH_3$ | H | $O(CH_2)_3$ | 4-pyridyl |
| $CH_3SO_2$ | $CH_3CO$ | $CH_3$ | H | $OCH(CH_3)$ | $C_4H_7$ |
| $CH_3SO_2$ | $CH_3CO$ | $CH_3$ | H | $O(CH_2)_3$ | $C_6H_{11}$ |
| $CH_3SO_2$ | $CH_3CO$ | $CH_3$ | H | $O(CH_2)_4$ | $C_7H_{13}$ |
| $CH_3SO_2$ | $CH_3CO$ | H | H | O | $C_6H_5$ |
| $CH_3SO_2$ | $CH_3CO$ | H | H | O | 4-$FC_6H_4$ |
| $CH_3CO$ | $CH_3CO$ | $C_2H_5$ | H | O | $C_5H_9$ |
| $CH_3CO$ | $CH_3CO$ | H | H | O | 2-$(C_6H_5)C_3H_4$ |

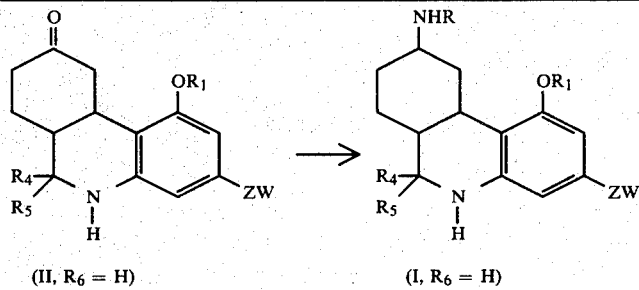

(II, $R_6$ = H)     (I, $R_6$ = H)

In the compounds of formula (I) tabulated below, Z is:
(a) alkylene or
(b) —(alk$_1$)$_m$—X—(alk$_2$)$_n$—, each of which is defined above. (CH$_2$)$_3$S corresponds to —(alk$_1$)—X—; —S(CH$_2$)$_3$ corresponds to —X—(alk$_2$).

| R | R$_1$ | R$_4$ | R$_5$ | Z | W |
|---|---|---|---|---|---|
| CH$_3$CO | CH$_3$CO | C$_2$H$_5$ | H | O | 4-(C$_6$H$_5$)C$_6$H$_{10}$ |
| CH$_3$CO | CH$_3$CO | CH$_3$ | H | O | 4-pyridyl |
| CH$_3$CO | CH$_3$CO | CH$_3$ | H | O | 3-piperidyl |
| CH$_3$CO | CH$_3$CO | H | H | SCH$_2$ | H |
| CH$_3$CO | CH$_3$CO | CH$_3$ | H | S(CH$_2$)$_5$ | H |
| CH$_3$CO | CH$_3$CO | H | H | S(CH$_2$)$_9$ | H |
| CH$_3$CO | CH$_3$CO | H | H | SCH(CH$_3$)(CH$_2$)$_3$ | H |
| CH$_3$CO | CH$_3$CO | CH$_3$ | H | SCH$_2$ | C$_3$H$_5$ |
| CH$_3$CO | CH$_3$CO | H | H | SCH$_2$ | C$_6$H$_{11}$ |
| CH$_3$CO | CH$_3$CO | CH$_3$ | H | S(CH$_2$)$_3$ | C$_6$H$_{11}$ |
| CH$_3$CO | CH$_3$CO | C$_2$H$_5$ | H | S(CH$_2$)$_4$ | C$_7$H$_{13}$ |
| CH$_3$CO | CH$_3$CO | H | H | SCH(CH$_3$)CH(CH$_3$)(CH$_2$)$_4$ | CH$_3$ |
| CH$_3$CO | CH$_3$CO | CH$_3$ | H | SC(CH$_3$)$_2$(CH$_2$)$_5$ | CH$_3$ |
| CH$_3$CO | CH$_3$CO | CH$_3$ | H | SCH$_2$ | C$_6$H$_5$ |
| CH$_3$CO | CH$_3$CO | CH$_3$ | H | SCH$_2$ | 4-FC$_6$H$_4$ |
| CH$_3$CO | CH$_3$CO | CH$_3$ | H | SCH(CH$_3$)CH$_2$ | 2-pyridyl |
| CH$_3$CO | CH$_3$CO | CH$_3$ | H | S | C$_6$H$_{11}$ |
| CH$_3$CO | CH$_3$CO | H | H | S | C$_6$H$_5$ |
| CH$_3$CO | CH$_3$CO | H | H | S | 4-pyridyl |
| CH$_3$CO | CH$_3$CO | CH$_3$ | H | S | C$_7$H$_{13}$ |
| CH$_3$CO | CH$_3$CO | CH$_3$ | H | S | 4-(C$_6$H$_5$)C$_6$H$_{10}$ |
| CH$_3$CO | CH$_3$CO | H | H | S | 4-ClC$_6$H$_4$ |
| CH$_3$CO | CH$_3$CO | H | H | SCH(CH$_3$)(CH$_2$)$_4$ | CH$_3$ |
| CH$_3$CO | CH$_3$CO | C$_2$H$_5$ | H | S(CH$_2$)$_4$ | CH$_3$ |
| CH$_3$CO | CH$_3$CO | CH$_3$ | CH$_3$ | OCH$_2$ | H |
| CH$_3$CO | CH$_3$CO | CH$_3$ | CH$_3$ | O(CH$_2$)$_9$ | H |
| CH$_3$CO | CH$_3$CO | CH$_3$ | CH$_3$ | OCH(CH$_3$)(CH$_2$)$_3$ | CH$_3$ |
| CH$_3$CO | CH$_3$CO | C$_6$H$_5$CH$_2$ | CH$_3$ | OCH(CH$_3$)(CH$_2$)$_3$ | 3-pyridyl |
| CH$_3$CO | CH$_3$CO | n-C$_4$H$_9$ | CH$_3$ | O | C$_6$H$_5$ |
| CH$_3$CO | CH$_3$CO | C$_6$H$_5$(CH$_2$)$_4$ | CH$_3$ | O | 4-FC$_6$H$_4$ |
| CH$_3$CO | CH$_3$CO | CH$_3$ | CH$_3$ | O | C$_5$H$_9$ |
| CH$_3$CO | CH$_3$CO | C$_2$H$_5$ | C$_2$H$_5$ | O | C$_7$H$_{13}$ |
| CH$_3$CO | CH$_3$CO | CH$_3$ | CH$_3$ | O | 3-(C$_6$H$_5$)C$_7$H$_{12}$ |
| CH$_3$CO | CH$_3$CO | CH$_3$ | CH$_3$ | S | 4-ClC$_6$H$_4$ |
| CH$_3$CO | CH$_3$CO | CH$_3$ | CH$_3$ | S | C$_7$H$_{13}$ |
| CH$_3$CO | CH$_3$CO | CH$_3$ | CH$_3$ | S | 4-(C$_6$H$_5$)C$_6$H$_{10}$ |
| CH$_3$CO | CH$_3$CO | n-C$_6$H$_{13}$ | CH$_3$ | S | C$_6$H$_5$ |
| CH$_3$CO | CH$_3$CO | C$_6$H$_5$CH$_2$ | CH$_3$ | S | C$_6$H$_5$ |
| CH$_3$CO | CH$_3$CO | C$_2$H$_5$ | C$_2$H$_5$ | SCH$_2$ | H |
| CH$_3$CO | CH$_3$CO | CH$_3$ | CH$_3$ | S(CH$_2$)$_9$ | CH$_3$ |
| CH$_3$CO | CH$_3$CO | CH$_3$ | CH$_3$ | SC(CH$_3$)$_2$(CH$_2$)$_6$ | CH$_3$ |
| CH$_3$CO | CH$_3$CO | C$_6$H$_5$CH$_2$ | H | SC(CH$_3$)$_2$(CH$_2$)$_6$ | H |
| CH$_3$CO | CH$_3$CO | C$_6$H$_5$(CH$_2$)$_2$ | CH$_3$ | S | H |
| CH$_3$CO | CH$_3$CO | n-C$_3$H$_7$ | H | OC(CH$_3$)$_2$(CH$_2$)$_6$ | H |
| CH$_3$CO | CH$_3$CO | i-C$_4$H$_9$ | C$_2$H$_5$ | OCH$_2$ | 4-pyridyl |
| CH$_3$CO | CH$_3$CO | C$_6$H$_5$(CH$_2$)$_4$ | CH$_3$ | O(CH$_2$)$_4$ | CH$_3$ |
| CH$_3$CO | CH$_3$CO | C$_6$H$_5$(CH$_2$)$_3$ | C$_2$H$_5$ | S | C$_6$H$_5$ |
| CH$_3$CO | CH$_3$CO | CH$_3$ | CH$_3$ | O(CH$_2$)$_6$ | 4-FC$_6$H$_4$ |
| CH$_3$CO | CH$_3$CO | CH$_3$ | CH$_3$ | SCH$_2$ | C$_6$H$_{11}$ |
| CH$_3$CO | CH$_3$CO | H | H | OCH(CH$_3$)(CH$_2$)$_5$ | H |
| i-C$_4$H$_9$CO | CH$_3$CO | CH$_3$ | CH$_3$ | OCH(CH$_3$)(CH$_2$)$_5$ | H |
| n-C$_5$H$_{11}$CO | CH$_3$CO | n-C$_3$H$_7$ | CH$_3$ | OCH(CH$_3$)(CH$_2$)$_5$ | H |
| CH$_3$SO$_2$ | CH$_3$CO | n-C$_6$H$_{13}$ | H | OCH(CH$_3$)(CH$_2$)$_5$ | H |
| CH$_3$CO | CH$_3$CO | H | H | C(CH$_3$)$_2$(CH$_2$)$_6$ | H |
| n-C$_3$H$_7$CO | n-C$_3$H$_7$CO | CH$_3$ | H | C(CH$_3$)$_2$(CH$_2$)$_6$ | H |
| n-C$_5$H$_{11}$CO | n-C$_5$H$_{11}$CO | n-C$_6$H$_{13}$ | CH$_3$ | C(CH$_3$)$_2$(CH$_2$)$_6$ | H |
| CF$_3$CO | i-C$_4$H$_9$CO | n-C$_4$H$_9$ | H | C(CH$_3$)$_2$(CH$_2$)$_6$ | H |
| 4-CH$_3$C$_6$H$_4$SO$_2$ | n-C$_4$H$_9$CO | i-C$_3$H$_7$ | CH$_3$ | C(CH$_3$)$_2$(CH$_2$)$_6$ | H |
| CH$_3$CO | CH$_3$CO | CH$_3$ | H | CH(CH$_3$)(CH$_2$)$_3$ | C$_6$H$_5$ |
| CF$_3$SO$_2$ | C$_2$H$_5$CO | C$_2$H$_5$ | CH$_3$ | CH(CH$_3$)(CH$_2$)$_3$ | C$_6$H$_5$ |

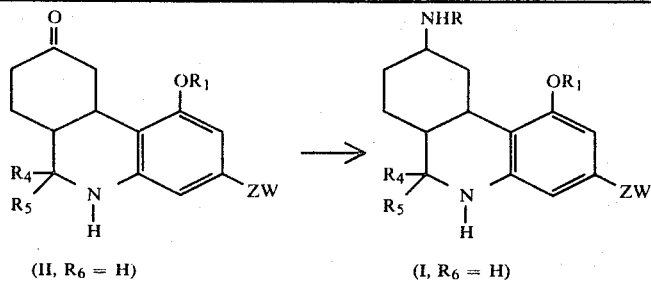

(II, R₆ = H) → (I, R₆ = H)

In the compounds of formula (I) tabulated below, Z is:
(a) alkylene or
(b) —(alk₁)$_m$—X—(alk₂)$_n$—, each of which is defined above. (CH₂)₃S corresponds to —(alk₁)—X—;  —S(CH₂)₃ corresponds to —X—(alk₂).

| R | R₁ | R₄ | R₅ | Z | W |
|---|---|---|---|---|---|
| n-C₅H₁₁CO | n-C₅H₁₁CO | n-C₆H₁₃ | H | CH(CH₃)(CH₂)₃ | C₆H₅ |

EXAMPLE 18

The following compounds of formula (I) are also prepared by the methods of Example 17 starting with the appropriate 5-substituted compounds of formula (II).

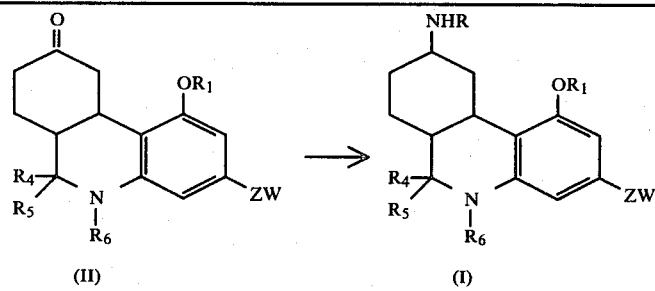

(II) → (I)

| R | R₁ | R₄ | R₅ | ZW | R₆ |
|---|---|---|---|---|---|
| CH₃SO₂ | CH₃CO | H | H | O(CH₂)₃CH₃ | CH₃ |
| CH₃CO | CH₃CO | H | H | OCH(CH₃)₂ | C₂H₅ |
| C₆H₅CO | C₆H₅CO | C₂H₅ | H | OCH₂C₆H₅ | CH₂C₆H₅ |
| CH₃CO | CH₃CO | H | H | O(CH₂)₂C₆H₅ | CH₂COOCH₃ |
| 2-Furoyl | CH₃CO | C₂H₅ | H | O(CH₂)₃—3-pyridyl | n-C₄H₉ |
| CF₃CO | n-C₄H₉CO | CH₃ | H | S(CH₂)₂CH₃ | (CH₂)₂CO₂C₂H₅ |
| CF₃CO | CH₃CO | CH₃ | H | SCH(CH₃)(CH₂)₄CH₃ | (CH₂)₃CO₂(CH₂)₃CH₃ |
| CF₃CO | CH₃CO | CH₃ | H | SCH(CH₃)(CH₂)₃C₆H₅ | CH₃ |
| n-C₄H₉CO | CH₃CO | CH₃ | H | 4-piperidylthio | CH₂C₆H₅ |
| n-C₅H₁₁CO | CH₃CO | H | H | SC(CH₃)₂(CH₂)₅CH₃ | i-C₃H₇ |
| 2-Thenyl | CH₃CO | CH₃ | H | OCH(CH₃)(CH₂)₄CH₃ | (CH₂)₄C₆H₅ |
| CH₃CO | CH₃CO | CH₃ | H | OCH(CH₃)(CH₂)₃C₆H₅ | CH₂CO₂—i-C₄H₉ |
| CH₃CO | CH₃CO | H | H | OCH(CH₃)(CH₂)₃C₆H₅ | (CH₂)₄CO₂—i-C₃H₇ |
| CH₃CO | CH₃CO | CH₃ | CH₃ | OCH(CH₃)(CH₂)₃—4-FC₆H₄ | n-C₃H₇ |
| CH₃SO₂ | CH₃CO | CH₃ | H | OCH(CH₃)(CH₂)₄CH₃ | n-C₆H₁₃ |
| CH₃SO₂ | CH₃CO | C₂H₅ | H | O(CH₂)₉CH₃ | COOC₂H₅ |
| CH₃SO₂ | CH₃CO | C₆H₅(CH₂)₃ | CH₃ | 4-FC₆H₅—O | CH₂C₆H₅ |
| n-C₄H₉SO₂ | CH₃CO | CH₃ | CH₃ | 4-pyridyloxy | (CH₂)₄C₆H₅ |
| C₂H₅SO₂ | H | CH₃ | CH₃ | O(CH₂)₃C₆H₁₁ | CO₂(CH₂)₃CH₃ |
| C₆H₅SO₂ | H | H | H | (CH₂)₄C₆H₅ | CHO |
| CH₃CO | CH₃CO | H | H | CH(CH₃)(CH₂)₃C₆H₅ | CHO |
| CH₃CH=CHCO | C₆H₅CO | C₂H₅ | H | (CH₂)₃C₅H₉ | CH₃CO |
| 2-Furoyl | CH₃CO | H | H | (CH₂)₉C₆H₁₁ | CH₃(CH₂)₂CO |
| 4-CH₃C₆H₄SO₂ | CH₃CO | CH₃ | CH₃ | CH₂—O—CH₃ | (CH₃)₂CHCH₂CO |
| C₆H₅SO₂ | CH₃CO | CH₃ | H | (CH₂)₄—O—(CH₂)₅C₆H₅ | C₆H₅CO |
| CH₃CO | CH₃CO | CH₃ | CH₃ | OCH₃ | C₆H₅CH₂CO |
| CH₃CO | CH₃CO | CH₃ | H | SC₆H₅ | C₆H₅(CH₂)₂CO |
| CH₃CO | CH₃CO | H | H | (CH₂)₃—S—CH₃ | C₆H₅(CH₂)₃CO |
| CH₃CO | CH₃CO | CH₃ | H | (CH₂)₅S(CH₂)₄C₆H₅ | C₆H₅(CH₂)₃CO |
| CH₃CO | CH₃CO | CH₃ | CH₃ | (CH₂)₄OC₆H₅ | C₆H₅CH₂OCO |
| CH₃CO | CH₃CO | H | H | (CH₂)₄C₃H₅ | C₆H₅CH₂OCO |
| CH₃CO | CH₃CO | H | H | 3-pyridyloxy | COOCH₃ |
| CH₃CO | CH₃CO | C₆H₅CH₂ | H | O(CH₂)₉C₆H₅ | (CH₂)₄CO₂—n-C₄H₉ |
| CH₃CO | CH₃CO | H | H | SC₇H₁₄ | (CH₂)₂CH(CH₃)₂ |
| CH₃CO | CH₃CO | CH₃ | H | 4-(C₆H₅)C₆H₁₀S— | CH(CH₃)₂ |
| CH₃CO | CH₃CO | CH₃ | H | OCH(CH₃)(CH₂)₃C₆H₅ | CHO |

-continued

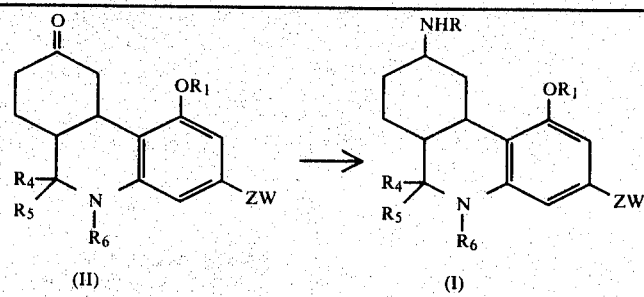

| R | R₁ | R₄ | R₅ | ZW | R₆ |
|---|----|----|----|----|----|
| $CH_3CO$ | $CH_3CO$ | $CH_3$ | H | $OCH(CH_3)(CH_2)_4CH_3$ | $CH_3$ |
| $CF_3CO$ | $CH_3CO$ | $i-C_4H_9$ | $CH_3$ | $OCH(CH_3)(CH_2)_4CH_3$ | $CH_3$ |
| $4-CH_3C_6H_4SO_2$ | $CH_3CO$ | $n-C_5H_{11}$ | $CH_3$ | $OCH(CH_3)(CH_2)_4CH_3$ | $CH_3$ |
| $CH_3SO_2$ | $CH_3CO$ | $C_2H_5$ | H | $C(CH_3)_2(CH_2)_5CH_3$ | $CH_3$ |
| $n-C_5H_{11}SO_2$ | $CH_3CO$ | $CH_3$ | $CH_3$ | $C(CH_3)_2(CH_2)_5CH_3$ | $CH_3$ |
| $n-C_4H_9CO$ | $CH_3CO$ | $(CH_3)_2CH(CH_2)_3$ | $CH_3$ | $C(CH_3)_2(CH_2)_5CH_3$ | $CH_3$ |
| $n-C_4H_9CO$ | $CH_3CO$ | $n-C_4H_9$ | H | $CH(CH_3)(CH_2)_3C_6H_5$ | $CH_3$ |
| $n-C_4H_9SO_2$ | $n-C_5H_{11}CO$ | $n-C_3H_7$ | $CH_3$ | $CH(CH_3)(CH_2)_3C_6H_5$ | $CH_3$ |
| $C_6H_5SO_2$ | $i-C_3H_7CO$ | $n-C_5H_{11}$ | H | $CH(CH_3)(CH_2)_3C_6H_5$ | $CH_3$ |

For those compounds wherein $R_6$ is formyl, alkanoyl, carbobenzyloxy or $C_6H_5(CH_2)_{x-1}CO$ where x is 1–4, and those compounds wherein ZW contains sulfur, the methods of Examples 14 or 15 are employed for preparation of the 9-amino intermediates.

EXAMPLE 19 dl-trans-5,6,6a,7,8,9,10,10a-Octahydro-1-acetoxy-9-acetylamino-5,6,6-trimethyl-3-(cyclohexylmethylthio)-benzo[c]quinoline To a stirred solution of 474 mg. (1.0 mmole) of dl-trans-5,6,6a,7,8,9,10,10a-octahydro-1-acetoxy-9-acetylamino-6,6-dimethyl-3-(cyclohexylmethylthio)-benzo[c]quinoline in 5 ml. acetonitrile cooled to 15° C. is added 0.5 ml. aqueous formaldehyde followed by 100 mg. of sodium cyanoborohydride. Acetic acid is added to maintain a neutral pH until the reaction is complete as evidenced by thin layer chromatography of the mixture. Ice water and ethyl ether are added to the reaction mixture, the ether layer separated and the aqueous layer extracted again with ether. The combined ether layers are dried and evaporated to dryness to afford the title compound.

The compounds prepared in Examples 6, 7, 8, 11, 13, 16 and 17 are converted to the corresponding 5-methyl derivatives of the following formula in like manner.

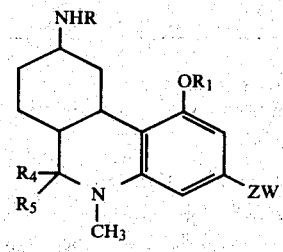

EXAMPLE 20 dl-trans-5,6,6a,7,8,9,10,10a-Octahydro-1-acetoxy-9-beta-acetamido-5-benzoyl-6-betamethyl-3-(5-phenyl-2-pentyloxy)benzo[c]quinoline To a stirred solution of dl-trans-5,6,6a,7,8,9,10,10a-octahydro-1-acetoxy-9-beta-acetamido-6-betamethyl-3-(5-phenyl-2-pentyloxy)benzo[c]quinoline (0.96 g., 2 mmole) in 3 ml. pyridine is added 0.42 g. (3 mmole) benzoyl chloride in 5 ml. chloroform. After stirring at reflux for one hour, the mixture is cooled, poured onto ice and extracted with ethyl ether. The combined ether extracts are washed with water, sodium bicarbonate, dried ($MgSO_4$) and evaporated to dryness to afford the desired product which is purified, if desired, by crystallization.

When the benzoyl chloride is replaced by an equimolar amount of acetyl chloride, propionyl chloride, isobutyryl chloride, valeryl chloride, 2-phenylacetyl bromide or 4-phenylbutyryl chloride, the corresponding compounds are obtained where $R_6$ is $CH_3CO$, $CH_3CH_2CO$, $(CH_3)_2CHCO$, $CH_3(CH_2)_3CO$, $C_6H_5CH_2CO$ or $C_6H_5(CH_2)_3CO$, respectively.

In like manner the compounds provided above wherein $R_6$ is hydrogen are converted to the corresponding benzoyl, acetyl, propionyl, butyryl, isobutyryl, valeryl, 2-phenylacetyl, 3-phenylpropionyl and 4-phenylbutyryl derivatives by reaction with the appropriate acyl chloride or acyl bromide. Use of carbobenzyloxy chloride affords the corresponding compounds wherein $R_6$ is $COOCH_2C_6H_5$.

EXAMPLE 21

[3(1R),6S,6aR,9R,10aR]-9-Acetamido-1-hydroxy-5,6,6a,7,8,9,10,10a-octahydro-5,6-dimethyl-3-(1-methyl-4-phenylbutoxy)benzo[c]quinoline A solution of 165 mg. (+)[3(1R),6S,6aR,9R,10aR]-trans-9-acetamido-1-acetoxy-5,6,6a,7,8,9,10,10a-octahydro-5,6-beta-dimethyl-3-(1-alpha-methyl-4-phenyl-butoxy)benzo[c]quinoline (prepared as described in Example 12) and 46 mg. potassium carbonate in 35 ml. methanol is stirred at room temperature for one hour. The reaction mixture is neutralized with acetic acid, concentrated to dryness in vacuo and the residue taken up in ethyl ether. The ether solution is washed with water, saturated sodium bicarbonate, and brine and dried over anhydrous magnesium sulfate. Evaporation of the ether affords the desired 1-hydroxy compound.

In like manner the compounds of formula (I), wherein $R_1$ is alkanoyl or benzoyl prepared above, are hydrolyzed to the corresponding compounds having the formula below wherein R, $R_4$, $R_5$, $R_6$, Z and W are as defined in the previous examples.

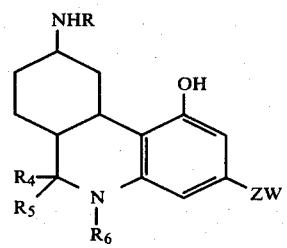

EXAMPLE 22

[3(1R),6S,6aR,9R,10aR]-9-Acetamido-5,6,6a,7,8,9,10,-10a-octahydro-5,6-dimethyl-1-(4-N-piperidylbutyryloxy)-3-(1-methyl-4-phenylbutoxy)benzo[c]quinoline hydrochloride [(I), NHR=beta-NHCOCH$_3$, $R_1$=C$_5$H$_{10}$N(CH$_2$)$_3$CO, $R_4$=beta-CH$_3$, $R_5$=H, $R_6$-CH$_3$,

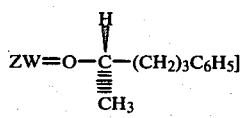

To a 25° C. solution of [3(1R),6S,6aR,9R,10aR]-9-acetamido-1-hydroxy-5,6,6a,7,8,9,10,10a-octahydro-5,6-dimethyl-3-(1-methyl-4-phenyl-butoxy)benzo[c]quinoline, 1.14 g. (2.5 mmole) in 20 ml. methylene chloride is added 4-N-piperidylbutyric acid hydrochloride, 0.52 g. (2.5 mmole) and dicyclohexylcarbodiimide, 0.573 g. (2.78 mmole). The reaction mixture is stirred at 25° C. for 6 hours, cooled at 0° C. overnight and filtered. The filtrate is evaporated and the residue triturated with ethyl ether to afford the desired hydrochloride salt.

Alternatively, the above filtrate is extracted with dilute hydrochloric acid. The aqueous phase is washed with ether, then made alkaline with potassium hydroxide solution. Extraction of the aqueous phase affords the free base of the title compound.

Treatment of this free base with excess hydrogen chloride in ether yields the dihydrochloride salt.

EXAMPLE 23 dl-trans-5,6,6a,7,8,9,10,10a-Octahydro-6-beta-methyl-9-methylsulfonylamino-1-(4-morpholinobutyryloxy)-3-(5-phenyl-2-pentyloxy)benzo[c]quinoline

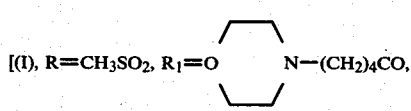

$R_4$=beta—CH$_3$, $R_5$=H, $R_6$=H, ZW=OCH(CH$_3$)(CH$_2$)$_3$C$_6$H$_5$]

To a solution of 708 mg. (1.5 mmole) dl-trans-9-methylsulfonylamino-1-hydroxy-5,6,6a,7,8,9,10,10a-octahydro-6-beta-methyl-3-(5-phenyl-2-pentyloxy)benzo[c]quinoline in 40 ml. of dry methylene chloride is added 315 mg. (1.5 mmole) 4-morpholinobutyric acid hydrochloride, and the mixture is stirred at room temperature under a nitrogen atmosphere. To this is added dropwise 12.5 ml. of 0.1 molar dicyclohexylcarbodiimide in methylene chloride and the resulting mixture is stirred for 24 hours. It is then cooled to 0° C., filtered, the filtrate extracted with 0.1 N hydrochloric acid, the aqueous phase washed with ether, then made alkaline with sodium hydroxide solution and extracted with ether. The ether extracts are dried (MgSO$_4$) and evaporated to dryness to afford the title compound. The product is purified, if desired, by chromatography on silica gel.

Repetition of this procedure, but using the appropriate 1-hydroxy compound provided by the procedure of Example 21 and the appropriate alkanoic acid or acid of formula $R_2R_3H(CH_2)_p$—COOH HCl affords the following compounds:

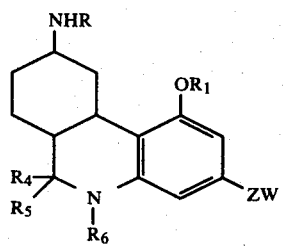

wherein $R_2$, $R_3$ and p are as previously defined; $R_4$, $R_5$, $R_6$, Z and W are as defined in Examples 17–20 and $R_1$ is as defined below.

| $R_1$ |
|---|
| COCH$_2$CH$_3$ |
| CO(CH$_2$)$_2$CH$_3$ |
| CO(CH$_2$)$_3$CH$_3$ |
| COCH$_2$NH$_2$ |
| CO(CH$_2$)$_2$NH$_2$ |
| CO(CH$_2$)$_4$NH$_2$ |
| CO(CH$_2$)N(CH$_3$)$_2$ |
| CO(CH$_2$)$_2$NH(C$_2$H$_5$) |
| CO(CH$_2$)$_4$NHCH$_3$ |
| CONH$_2$ |
| CON(C$_2$H$_5$)$_2$ |
| CON(C$_4$H$_9$)$_2$ |
| CO(CH$_2$)$_3$NH(C$_3$H$_7$) |
| CO(CH$_2$)$_2$N(C$_4$H$_9$)$_2$ |
| COCH$_2$—piperidino |
| COCH$_2$—pyrrolo |
| CO(CH$_2$)$_2$—morpholino |
| CO(CH$_2$)$_2$—N—butylpiperazino |
| CO(CH$_2$)$_3$—pyrrolidino |
| CO—piperidino |
| CO—morpholino |
| CO—pyrrolo |
| CO—N—(methyl)piperazino |
| CO—C$_6$H$_5$ |
| COCH(CH$_3$)(CH$_2$)$_2$—piperidino |

Basic esters are obtained as their hydrochloride salts. Careful neutralization with sodium hydroxide affords the free basic esters.

EXAMPLE 24 dl-9-Acetamido-1-acetoxy-6-methyl-3-(3-methyl-2-octylsulfinyl)-5,6,6a,7,8,9,10,10a-octahydrobenzo[c]quinoline [(I), R=$R_1$=CH$_3$CO, $R_4$=CH$_3$, $R_5$=$R_6$=H, ZW=S(O)C$_9$H$_{19}$]

Equimolar amounts of m-chloroperbenzoic acid and dl-9-acetamido-1-acetoxy-6-methyl-3-(3-methyl-2-octylthio)5,6,6a,7,8,9,10,10a-octahydrobenzo[c]quinoline are added to a mixture of chloroform and acetic acid (2:1 v/v) and the mixture stirred at room temperature for one hour. The reaction mixture is washed with water, the organic phase dried over magnesium sulfate and evaporated to dryness at reduced pressure to give the title compound.

In like manner the thio ethers of Examples 14 through 19 are oxidized to the corresponding sulfoxides.

EXAMPLE 25 dl-9-Acetamido-1-acetoxy-6-methyl-3-(3-methyl-2-octylsulfonyl)-5,6,6a,7,8,9,10,10a-octahydrobenzo[c]quinoline [(I) as in above Example but ZW=SO$_2$C$_9$H$_{19}$]

The procedure of Example 24 is repeated but using two equivalents of m-chloroperbenzoic acid as oxidizing agent per mole of thio ether reactant to give the title sulfone.

Similarly the thio ethers of Examples 14–19 are oxidized to the corresponding sulfonyl derivatives.

EXAMPLE 26

General Hydrochloride Acid Addition Salt Formation

Into an ethereal solution of the appropriate benzo[c]quinoline free base of formula (I) is passed a molar excess of anhydrous hydrogen chloride and the resulting precipitate is separated and recrystallized from an appropriate solvent, e.g. methanol-ether.

Similarly, the free bases of formula (I) are converted to their corresponding hydrobromide, sulfate, nitrate, phosphate, acetate, butyrate, citrate, malonate, maleate, fumarate, malate, glycolate, gluconate, lactate, salicylate, sulfosalicylate, succinate, pamoate and tartarate salts.

EXAMPLE 27

One hundred mg. of dl-trans-5,6,6a-beta,7,8,9,10,10a-alpha-octahydro-1-acetoxy-9-acetamido-5-methyl-6-beta-methyl-3-(5-phenyl-2-pentyloxy)benzo[c]quinoline are intimately mixed and ground with 900 mg. of starch. The mixture is then loaded into telescoping gelatin capsules such that each capsule contains 10 mg. of drug and 90 mg. of starch.

EXAMPLE 28

A tablet base is prepared by blending the ingredients listed below:

| Sucrose | 80.3 parts |
|---|---|
| Tapioca starch | 13.2 parts |
| Magnesium stearate | 6.5 parts |

Sufficient d(+)-trans-1-acetoxy-9-beta-acetamido-5,6,6a-beta,7,8,9,10,10a-alpha-octahydro-5,6-beta-dimethyl-3-(1-alpha-methyl-4-phenylbutoxy)benzo[c]quinoline is blended into this base to provide tablets containing 0.1, 0.5, 1, 5, 10 and 25 mg. of drug.

EXAMPLE 29

Suspensions of dl-trans-5,6,6a-beta,7,8,9,10,10a-alpha-octahydro-1-acetoxy-9-alpha-acetamido-5,6-beta-dimethyl-3-(5-phenyl-2-pentyloxy)benzo[c]quinoline are prepared by adding sufficient amounts of drug to 0.5% methylcellulose to provide suspensions having 0.05, 0.1, 0.5, 1, 5 and 10 mg. of drug per ml.

PREPARATION A

Ethyl dl-3-(3,5-Dimethoxyanilino)butyrate

To a solution of 3,5-dimethoxyaniline hydrochloride (370 g., 1.45 mole), reagent grade methanol (4.5 l.) and ethyl acetoacetate (286.3 g., 2.64 mole) in a 12 liter round bottom, 3 neck flask fitted with mechanical stirrer and reflux condenser is added sodium cyanoborohydride (54 g., 0.73 mole) in one portion. After the refluxing subsides (10 minutes) the mixture is heated on a steam bath for an additional 20 minutes. To the cooled reaction mixture is added additional sodium cyanoborohydride (5.4 g., 0.07 mole) and ethyl acetoacetate (28.6 g., 0.26 mole) and the mixture refluxed for 30 minutes. This latter process is repeated once more.

The reaction mixture is isolated in portions by pouring ca. 500 ml. onto 1 liter of ice-water/500 ml. methylene chloride, separating the layers and back-washing the aqueous phase with additional methylene chloride (100 ml.). (This process is repeated using 500 ml. portions until the entire reaction mixture is worked up.)

The methylene chloride layers are combined and dried (MgSO$_4$), decolorized with charcoal, filtered and evaporated to yield a yellow colored oil.

The excess ethyl acetoacetate is distilled (at 130° C. oil bath temperature and 1–5 mm. pressure) leaving the crude ethyl 3-(3,5-dimethoxyanilino)butyrate (an amber colored viscous oil): 376 g. (72% yield) which is used without further purification.

It has the following spectral characteristics: $^1$H NMR (60 MHz) (CDCl$_3$) ppm (delta): 5.82–6.0 (m,3H, aromatic), 4.20 (q,2H, ester methylene), 3.80–4.00 (m,2H, —NH and

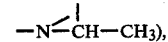

3.78 (s,6H,—OCH$_3$), 2.40–2.55 (m,2H, —CH$_2$COOEt), 1.78 (d,3H,methyl) and 1.29 (t,3H,methyl).

PREPARATION B dl-Ethyl 3-(3,5-Dimethoxyanilino)hexanoate

Following the procedure of Preparation A, condensation of 3,5-dimethoxyaniline hydrochloride and ethyl butyrylacetate gives ethyl dl-3-(3,5-dimethoxyanilino)-hexanoate. It is converted to the hydrochloride salt by addition of hydrogen chloride to a methylene chloride solution thereof; m.p. 127°–129.5° C. Recrystallization from cyclohexane/benzene (5:1) gives the analytical sample, m.p. 126°–128.5° C.

Analysis: Calcd. for C$_{16}$H$_{25}$O$_4$N HCl: C, 57.91; H, 7.90; N, 4.22% Found: C, 57.89; H, 7.74; N, 4.40% m/e-295 (m+)

$^1$H NMR (60 MHz) (CDCl$_3$) ppm (delta): 10.76–11.48 (b, variable, 2H, NH$_2$+), 6.77 (d, J=2 Hz, 2H, meta H's), 6.49, 6.45 (d of d, J=2 Hz, 1H, meta H), 4.08 (q, 2H, OCH$_2$), 3.77 (s, 6H, [OCH$_3$]$_2$), ca. 3.5–4.8 (m, 1H, CH-N), 2.90 (t, 2H, CH$_2$—C=O), ca. 1.4–2.2 (m, 4H, [CH$_2$]$_2$), 1.21 (t, 3H, O—C—CH$_3$), 0.84 (t, 3H, —C—CH$_3$).

PREPARATION C dl-Ethyl 3-[3,4-Dimethoxy-N-ethoxycarbonyl)anilino]butyrate

Method A

Ethyl chloroformate (71.4 ml. 0.75 mole) is added dropwise over a 45 minute period to a mixture of ethyl 3-(3,5-dimethoxyanilino)butyrate (159.8 g., 0.598 mole), methylene chloride (100 ml.), and pyridine (100 ml., 1.24 moles) at 0° C. under a nitrogen atmosphere. The mixture is stirred for 40 minutes following addition of the ethyl chloroformate and is then poured into a mixture of chloroform (750 ml.) and ice-water (500 ml.). The chloroform layer is separated, washed successively with 10% hydrochloric acid (3×500 ml.), saturated aqueous sodium bicarbonate (1×300 ml.) and saturated aqueous sodium chloride (1×400 ml.) and then dried (MgSO$_4$). It is then decolorized with activated charcoal and concentrated under reduced pressure to an oil (215 g.). The product is used as is.

Method B

Under a positive nitrogen atmosphere a mixture of ethyl 3-(3,5-dimethoxyanilino)butyrate (376 g., 1.4 mole), methylene chloride (1.4 liters) and anhydrous potassium carbonate (388.8 g., 2.81 mole) is stirred and cooled in an ice bath to 0°–5° C. Ethyl chloroformate (153 g., 1.41 mole) is added in one portion. The mixture is allowed to warm to room temperature over a period of one hour, ethyl chloroformate (153 g., 1.41 mole) is added once more and the mixture is refluxed on a steam bath for one hour. It is then allowed to cool to room temperature and the potassium carbonate removed by filtration. The red colored filtrate is washed successively with water (2×1000 ml.), brine (1×500 ml.), dried (MgSO$_4$), and then decolorized and evaporated under reduced pressure to afford 439 g. of crude product which is used without further purification.

$^1$H NMR (60 MHz) (CDCl$_3$) ppm (delta): 6.2–6.42 (m, 3H, aromatic), 4.65 (sextet, 1H, —N—CH—, CH$_3$), 4.10–4.15 (2 quartets, 4H, ester methylenes), 3.70 (s, 6H, —OCH$_3$), 2.30–2.60 (m, 2H, —CH$_2$COOEt), 1.00–1.40 (m, 9H, 3 methyl).

PREPARATION D dl-3-[(3,5-Dimethoxy-N-ethoxycarbonyl)anilino]-butyric Acid

Method A

Ethyl 3-[(3,5-dimethoxy-N-ethoxycarbonyl)anilino]-butyrate (202 g., 0.595 mole), aqueous sodium hydroxide (595 ml. of 1 N) and ethanol (595 ml.) are combined and stirred at room temperature overnight. The reaction mixture is concentrated to about 600 ml. volume under reduced pressure, the concentrate diluted with water to 1200 ml. volume and extracted with ethyl acetate (3×750 ml.). The aqueous layer is then acidified with 10% hydrochloric acid to pH 2 and extracted again with ethyl acetate (3×750 ml.). These latter extracts are combined, washed with brine, dried (MgSO$_4$), filtered and concentrated in vacuo to yield the title product as an oil (163.5 g., 88.2%).

Method B

A 5 liter, 3-neck round bottom flask equipped with mechanical stirrer and reflux condenser is charged with a solution of ethyl 3-[(3,5-dimethoxy-N-ethoxycarbonyl)anilino]-butyrate (439 g., 1.41 moles) in ethanol (2 liters). Sodium hydroxide (2 liters of 1 N) is added and the mixture refluxed on a steam bath for 3 hours. The reaction mixture is poured onto 5 liters of ice-water and extracted in one liter portions with diethyl ether 500 ml./portion). The aqueous layer is cooled by adding ca. one liter of ice and then acidified with concentrated hydrochloric acid (1.75 ml., 2.1 moles). It is extracted in portions of one liter with methylene chloride (250 ml./portion). The methylene chloride layers are combined and dried over magnesium sulfate, decolorized with charcoal and evaporated to dryness to yield a viscous yellow oil. Crystallization from ether/cyclohexane (1:2) affords 224 g. (55.3%) of crystalline product, m.p. 78°–80° C. This material is used without further purifications in the following step.

$^1$H NMR (60 MHz) (CDCl$_3$) ppm (delta): 6.24–6.53 (m, 3H, aromatic), 4.65 (sextet, 1H, —N(-COOC$_2$H$_5$)CH(CH$_3$)—CH$_2$COOC$_2$H$_5$), 4.10 (quartet, 2H, ester methylene), 3.78 (s, 6H, OCH$_3$), 2.40–2.60 (m, 2H, —CH$_2$COOH), 1.18 (t), 1.28 (d, 6H, methyl), 10.8 (bs, variable, 1H, COOH).

MS (mol. ion) m/e-311.

An analytical sample, obtained by recrystallization from ethyl acetate/hexane (1:5), melted at 89°–91° C.

Analysis: Calcd for C$_{15}$H$_{21}$O$_6$N: C, 57.86; H, 6.80; N, 4.50%. Found: C, 58.08; H, 6.65; N, 4.46%.

PREPARATION E d- and l-3-[(3,5-Dimethoxy-4-N-ethoxycarbonyl)anilino]-butyric Acids

A mixture of dl-3-[(3,5-dimethoxy-N-ethoxycarbonyl)anilino]butyric acid (136.6 g., 0.44 mole) and l-ephedrine (72.5 g., 0.44 mole) is dissolved in methylene chloride (500 ml.). The methylene chloride is then removed in vacuo to yield the l-ephedrine salt of dl-3-[(3,5-dimethoxy-N-ethoxycarbonyl)anilino]butyric acid as an oil, [alpha]$_D^{25}$ = −20.0 (c=1.0, CHCl$_3$). Addition of ether (1500 ml.) causes crystallization of a white solid which is separated by filtration and dried (102 g.), m.p. 114°–116° C. Recrystallization from ethyl acetate/hexane (1:1) affords 71.1 g. (34%) of the l-ephedrine salt of l-3-[(3,5-dimethoxy-N-ethoxycarbonyl)anilino]butyric acid; m.p. 126°–127° C.

Analysis: Calcd for C$_{25}$H$_{36}$O$_7$N$_2$: C, 63.00; H, 7.61; N, 5.88%. Found: C, 62.87; H, 7.64; N, 5.88%.

[alpha]$_D^{25}$ = −43.5° (c=1.0, CHCl$_3$).

The l-ephedrine salt of the l-isomer is stirred in a mixture of ethyl acetate (1000 ml.) and 10% hydrochloric acid (400 ml.) for ten minutes. The organic phase is separated, washed with 10% hydrochloric acid (2×400 ml.), dried and concentrated under reduced pressure to an oil. Crystallization of the oil from ethyl acetate/hexane (400 ml. of 1:1) affords 34.6 g. of l-3-[(3,5-dimethoxy-N-ethoxycarbonyl)anilino]butyric acid, m.p. 96°–97° C.

Analysis: Calcd for C$_{15}$H$_{21}$O$_6$N: C, 57.86; H, 6.80; N, 4.50%. Found: C, 57.90; H, 6.66; N, 4.45%.

[alpha]$_D^{25}$ = −25.4° (c=1.0, CHCl$_3$).

The mother liquor remaining from recrystallization of the l-ephedrine salt of the l-isomer is treated with hydrochloric acid as described above to give crude d-3-[(3,5-dimethoxy-N-ethoxycarbonyl)anilino]butyric acid. Treatment of the crude acid with d-ephedrine affords, after recrystallization from ether, the d-ephedrine salt of the d-isomer, m.p. 124°–125° C.

Analysis: Calcd for C$_{25}$H$_{36}$O$_7$N$_2$: C, 63.00; H, 7.61; N, 5.88%. Found: C, 62.82; H, 7.47; N, 5.97%.

[alpha]$_D^{25}$ = +44.0° (c=1.0, CHCl$_3$).

The d-ephedrine salt is converted to d-3-[(3,5-dimethoxy-N-ethoxycarbonyl)anilino]butyric acid in the same manner as described above for conversion of the l-ephedrine salt to the free acid. M.p. 96°–97° C. after recrystallization from ethyl acetate/hexane (3:5).

Analysis: Calcd for C$_{15}$H$_{21}$O$_6$N: C, 57.86; H, 6.80; N, 4.50%. Found: C, 57.95; H, 6.57; N, 4.35%.

[alpha]$_D^{25}$ = +25.3° (c=1.0, CHCl$_3$).

PREPARATION F

Methyl 3-(3,5-Dimethoxyanilino)propionate

A mixture of 3,5-dimethoxyaniline (114.9 g., 0.75 mole), methyl acrylate (69.73 g., 0.81 mole) and glacial acetic acid (2 ml.) is refluxed for 20 hours. Reflux is discontinued and the reaction mixture is concentrated and then distilled in vacuo, to yield 106.8 g. (73.9%) of the title product, b.p. 174°–179° C. (0.7 mm.).

$^1$H NMR (60 MHz) (CDCl$_3$) ppm (delta): 5.62–5.95 (m, 3H, aromatic), 4.1 (variable, bs, 1H, —NH), 3.74 (s, 6H, —OCH$_3$), 3.68 (s, 3H, COOCH$_3$), 3.41 and 2.59 (two 2H triplets, —NCH$_2$CH$_2$CO$_2$).

Repetition of this procedure but using the appropriate aniline reactant in place of 3,5-dimethoxyaniline affords the following compounds.

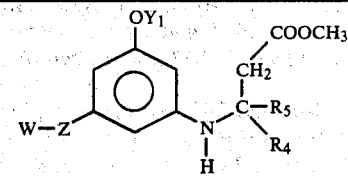

| Y$_1$ | Z—W |
|---|---|
| C$_2$H$_5$ | OC$_2$H$_5$ |
| C$_7$H$_7$ | OC$_7$H$_7$ |
| C$_7$H$_7$ | SCH$_3$ |
| CH$_3$ | SCH$_3$ |
| C$_2$H$_5$ | SCH$_3$ |

PREPARATION G

Methyl 3-(3,5-Dimethoxyanilino)alkanoates

The procedure of Preparation F is repeated but using the appropriate ester R$_4$R$_5$C=CH—COOCH$_3$ in place of methyl acrylate and the appropriate protected aniline reactant to give the following compounds.

When R$_5$ is hydrogen, the same products are obtained by the procedure of Preparation A but using methyl acetoacetate and methyl propionylacetate in place of ethyl acetoacetate and the appropriate protected aniline reactant.

| Y$_1$ | Z—W | R$_4$ | R$_5$ |
|---|---|---|---|
| CH$_3$ | OCH$_3$ | CH$_3$ | H |
| CH$_3$ | OCH$_3$ | C$_2$H$_5$ | H |
| C$_2$H$_5$ | OC$_2$H$_5$ | CH$_3$ | CH$_3$ |
| CH$_3$ | SCH$_3$ | CH$_3$ | H |
| CH$_3$ | SCH$_3$ | C$_2$H$_5$ | H |
| C$_7$H$_7$ | SCH$_3$ | C$_2$H$_5$ | H |
| C$_2$H$_5$ | OC$_2$H$_5$ | C$_2$H$_5$ | CH$_3$ |
| C$_7$H$_7$ | OC$_7$H$_7$ | CH$_3$ | H |
| C$_7$H$_7$ | OC$_7$H$_7$ | C$_2$H$_5$ | H |
| C$_2$H$_5$ | SCH$_3$ | CH$_3$ | CH$_3$ |
| C$_7$H$_7$ | SCH$_3$ | CH$_3$ | H |
| CH$_3$ | OCH$_3$ | C$_2$H$_5$ | C$_2$H$_5$ |
| CH$_3$ | SCH$_3$ | C$_2$H$_5$ | CH$_3$ |
| CH$_3$ | OCH$_3$ | CH$_3$ | CH$_3$ |
| CH$_3$ | OCH$_3$ | n-C$_3$H$_7$ | H |
| CH$_3$ | OCH$_3$ | n-C$_4$H$_9$ | H |
| CH$_3$ | OCH$_3$ | n-C$_6$H$_{13}$ | H |
| CH$_3$ | SCH$_3$ | n-C$_3$H$_7$ | H |
| CH$_3$ | SCH$_3$ | n-C$_5$H$_{11}$ | CH$_3$ |
| C$_7$H$_7$ | OC$_7$H$_7$ | i-C$_3$H$_7$ | H |
| CH$_3$ | OCH$_3$ | n-C$_4$H$_9$ | CH$_3$ |
| CH$_3$ | OC$_2$H$_5$ | n-C$_6$H$_{13}$ | CH$_3$ |
| CH$_3$ | OCH$_3$ | CH$_2$C$_6$H$_5$ | H |
| CH$_3$ | OCH$_3$ | CH$_2$C$_6$H$_5$ | CH$_3$ |
| CH$_3$ | OCH$_3$ | (CH$_2$)$_4$C$_6$H$_5$ | CH$_3$ |
| CH$_3$ | SCH$_3$ | CH$_2$C$_6$H$_5$ | CH$_3$ |
| CH$_3$ | OCH$_3$ | (CH$_2$)$_3$C$_6$H$_5$ | CH$_3$ |
| CH$_3$ | SCH$_3$ | (CH$_2$)$_2$C$_6$H$_5$ | C$_2$H$_5$ |
| CH$_3$ | SCH$_3$ | CH$_2$C$_6$H$_5$ | H |
| C$_2$H$_5$ | OC$_2$H$_5$ | C$_2$H$_5$ | C$_2$H$_5$ |
| C$_7$H$_7$ | SCH$_3$ | (CH$_2$)$_4$C$_6$H$_5$ | C$_2$H$_5$ |
| C$_7$H$_7$ | OC$_7$H$_7$ | CH$_3$ | CH$_3$ |
| C$_2$H$_5$ | OC$_2$H$_5$ | (CH$_2$)$_2$C$_6$H$_5$ | CH$_3$ |

PREPARATION H dl-Methyl 3-{[3-hydroxy-5-(5-phenyl-2-pentyl)]anilino}propionate

A mixture of 3-hydroxy-5-(5-phenyl-2-pentyl)-aniline (1.0 g.), methyl acrylate (345 mg.), and acetic acid (0.1 ml.) is heated at 106°–110° C. overnight. The cooled residue is dissolved in 100 ml. ethyl acetate and washed twice with 100 ml. of saturated sodium bicarbonate solution. The organic phase is then dried (MgSO$_4$) and evaporated to a crude residue which is chromatographed on 130 g. of silica gel using benzene-ether (2:1) as the eluant. After elution of less polar impurities, 540 mg. (40%), dl-methyl 3-{[3-hydroxy-5-(5-phenyl-2-pentyl)]anilino}propionate is collected. It has the following spectral characteristics:

$^1$H NMR (60 MHz) (CDCl$_3$) ppm (delta): 7.14 (s, 5H, aromatic), 5.83–6.13 (m, 3H, aromatic), 3.66 (s, 3H, —COOCH$_3$), 3.37 (t, 2H, —NCH$_2$), 2.16–2.78 (m, 5H, —CH$_2$COO and benzylic), 1.28–1.69 (m, 4H, —(CH$_2$)$_2$—), 1.11 (d, 3H, >—CH$_3$), 4.4–5.2 and 1.28–2.78 (variable, 1H, NH, OH).

m/e-341 (m+)

PREPARATION I

Methyl 3-[(3,5-Dimethoxy-N-ethoxycarbonyl)anilino]propionate

Ethyl chloroformate (2.0 g., 8.4 mmole) is added dropwise over a 10 minute period to a mixture of methyl 3-(3,5-dimethoxyanilino)propionate (1.0 ml., 10.5 mmole), methylene chloride (5 ml.) and pyridine (5 ml.) at 0° C. under a nitrogen atmosphere. The mixture is stirred at 0° C. for 20 minutes following addition of the ethyl chloroformate and then at room temperature for an additional 20 minutes, and is then poured into a mixture of methylene chloride (75 ml.) and ice-water (50 ml.). The methylene chloride layer is separated, washed successively with 10% hydrochloric acid (2×50 ml.), saturated aqueous sodium bicarbonate (1×30 ml.) and saturated aqueous sodium chloride (1×40 ml.) and dried (MgSO$_4$). It is then decolorized with activated charcoal and concentrated under reduced pressure to an oil (2.72 g.). The product is used as is.

Similarly, dl-methyl-3-[3-hydroxy-5-(5-phenyl-2-pentyl)anilino]propionate is converted to dl-methyl-3-{[3-hydroxy-5-(5-phenyl-2-pentyl)-N-ethoxycarbonyl-]anilino}propionate and the following compounds are prepared from compounds of Preparations F and G by reaction with the appropriate alkyl chloroformate or other reactant of formula R$_6$ Br where R$_6$ is other than hydrogen:

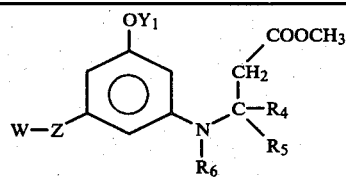

| Y$_1$ | Z—W | R$_4$ | R$_6$ | R$_5$ |
|---|---|---|---|---|
| CH$_3$ | OCH$_3$ | H | COO—n-C$_4$H$_9$ | H |
| C$_2$H$_5$ | OC$_2$H$_5$ | H | CH$_2$COOC$_2$H$_5$ | H |
| C$_7$H$_7$ | OC$_7$H$_7$ | H | COOCH$_3$ | H |
| C$_7$H$_7$ | SCH$_3$ | H | COOC$_2$H$_5$ | H |
| CH$_3$ | SCH$_3$ | H | COO—n-C$_3$H$_7$ | H |
| C$_2$H$_5$ | SCH$_3$ | H | (CH$_2$)$_2$COOCH$_3$ | H |
| CH$_3$ | OCH$_3$ | CH$_3$ | CH$_2$COOC$_2$H$_5$ | H |
| CH$_3$ | OCH$_3$ | C$_2$H$_5$ | COOCH$_3$ | H |
| C$_2$H$_5$ | SCH$_3$ | CH$_3$ | COOCH$_3$ | H |
| CH$_3$ | SCH$_3$ | CH$_3$ | COOC$_2$H$_5$ | H |
| C$_2$H$_5$ | OC$_2$H$_5$ | C$_2$H$_5$ | CH$_2$COO—n-C$_4$H$_9$ | H |
| C$_7$H$_7$ | OC$_2$H$_5$ | C$_2$H$_5$ | COOC$_2$H$_5$ | H |
| C$_7$H$_7$ | OC$_7$H$_7$ | CH$_3$ | COOCH$_3$ | H |
| C$_7$H$_7$ | SCH$_3$ | C$_2$H$_5$ | COOC$_2$H$_5$ | H |
| C$_7$H$_7$ | OC$_7$H$_7$ | C$_2$H$_5$ | COOCH$_3$ | H |
| C$_2$H$_5$ | SCH$_3$ | CH$_3$ | COO—i-C$_3$H$_7$ | H |
| C$_7$H$_7$ | SCH$_3$ | CH$_3$ | (CH$_2$)$_3$COOC$_2$H$_5$ | H |
| CH$_3$ | OCH$_3$ | H | COOC$_7$H$_7$ | H |
| CH$_3$ | OCH$_3$ | CH$_3$ | COOC$_7$H$_7$ | H |
| CH$_3$ | OCH$_3$ | CH$_3$ | CH$_3$ | H |
| CH$_3$ | OCH$_3$ | CH$_3$ | C$_2$H$_5$ | H |
| CH$_3$ | OCH$_3$ | CH$_3$ | n-C$_4$H$_9$ | H |
| C$_2$H$_5$ | SCH$_3$ | H | i-C$_3$H$_7$ | H |
| C$_2$H$_5$ | OCH$_3$ | CH$_3$ | CH$_2$C$_6$H$_5$ | H |
| CH$_3$ | OC$_2$H$_5$ | CH$_3$ | (CH$_2$)$_2$C$_6$H$_5$ | H |
| C$_2$H$_5$ | OCH$_3$ | CH$_3$ | (CH$_2$)$_4$C$_6$H$_5$ | H |
| C$_2$H$_5$ | SCH$_3$ | H | CH$_3$ | H |
| CH$_3$ | OCH$_3$ | C$_2$H$_5$ | CH$_2$C$_6$H$_5$ | H |
| CH$_3$ | OCH$_3$ | C$_2$H$_5$ | CH$_3$ | H |
| CH$_3$ | SCH$_3$ | C$_2$H$_5$ | (CH$_2$)$_3$C$_6$H$_5$ | H |
| C$_2$H$_5$ | OCH$_3$ | CH$_3$ | COOC$_2$H$_5$ | CH$_3$ |
| C$_2$H$_5$ | OCH$_3$ | CH$_3$ | COOCH$_3$ | C$_2$H$_5$ |
| CH$_3$ | OCH$_3$ | C$_2$H$_5$ | COOC$_2$H$_5$ | C$_2$H$_5$ |
| C$_2$H$_5$ | SCH$_3$ | CH$_3$ | COOC$_2$H$_5$ | CH$_3$ |
| CH$_3$ | OC$_2$H$_5$ | CH$_3$ | CH$_3$ | CH$_3$ |
| CH$_3$ | SCH$_3$ | C$_2$H$_5$ | COOC$_2$H$_5$ | CH$_3$ |
| CH$_3$ | OCH$_3$ | CH$_3$ | COOCH$_2$C(CH$_3$)$_3$ | CH$_3$ |
| CH$_3$ | OCH$_3$ | CH$_3$ | CH$_2$COOCH$_3$ | H |
| CH$_3$ | OCH$_3$ | CH$_3$ | (CH$_2$)$_4$COOCH$_3$ | H |
| CH$_3$ | OCH$_3$ | CH$_3$ | n-C$_6$H$_{13}$ | H |
| CH$_3$ | OCH$_3$ | n-C$_3$H$_7$ | COOCH$_3$ | H |
| CH$_3$ | OCH$_3$ | n-C$_4$H$_9$ | COOCH$_3$ | H |
| CH$_3$ | OCH$_3$ | n-C$_6$H$_{13}$ | COOCH$_3$ | H |
| CH$_3$ | OC$_7$H$_7$ | n-C$_4$H$_9$ | CH$_3$ | CH$_3$ |
| CH$_3$ | SCH$_3$ | n-C$_5$H$_{11}$ | CH$_2$C$_6$H$_5$ | CH$_3$ |
| CH$_3$ | OC$_7$H$_7$ | CH$_2$C$_6$H$_5$ | (CH$_2$)$_4$C$_6$H$_5$ | CH$_3$ |
| C$_2$H$_5$ | OC$_2$H$_5$ | (CH$_2$)$_2$C$_6$H$_5$ | C$_2$H$_5$ | CH$_3$ |
| C$_7$H$_7$ | SCH$_3$ | (CH$_2$)$_4$C$_6$H$_5$ | n-C$_5$H$_{11}$ | C$_2$H$_5$ |
| CH$_3$ | OCH$_3$ | (CH$_2$)$_4$C$_6$H$_5$ | COOC$_2$H$_5$ | CH$_3$ |
| CH$_3$ | OCH$_3$ | CH$_2$C$_6$H$_5$ | CH$_3$ | CH$_3$ |
| CH$_3$ | OCH$_3$ | CH$_3$ | COCH$_3$ | CH$_3$ |
| CH$_3$ | SCH$_3$ | (CH$_2$)$_2$C$_6$H$_5$ | CHO | CH$_3$ |
| C$_7$H$_7$ | OC$_7$H$_7$ | CH$_3$ | COC$_5$H$_{11}$ | CH$_3$ |
| CH$_3$ | OCH$_3$ | CH$_3$ | COCH$_2$C$_6$H$_5$ | CH$_3$ |
| CH$_3$ | OCH$_3$ | CH$_3$ | CO(CH$_2$)$_3$C$_6$H$_5$ | H |

-continued

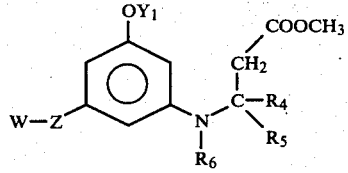

| Y$_1$ | Z—W | R$_4$ | R$_6$ | R$_5$ |
|---|---|---|---|---|
| CH$_3$ | SCH$_3$ | H | COCH$_3$ | H |
| CH$_3$ | SCH$_3$ | H | n-C$_6$H$_{13}$ | H |
| CH$_3$ | SCH$_3$ | n-C$_3$H$_7$ | n-C$_4$H$_9$ | H |
| CH$_3$ | OCH$_3$ | CH$_2$C$_6$H$_5$ | COOCH$_3$ | H |
| C$_7$H$_7$ | OC$_7$H$_7$ | i-C$_3$H$_7$ | COOC$_2$H$_5$ | H |
| CH$_3$ | OC$_2$H$_5$ | n-C$_6$H$_{13}$ | i-C$_3$H$_7$ | CH$_3$ |
| CH$_3$ | SCH$_3$ | CH$_2$C$_6$H$_5$ | COOC$_7$H$_7$ | CH$_3$ |
| CH$_3$ | OCH$_3$ | (CH$_2$)$_3$C$_6$H$_5$ | COCH$_2$C$_6$H$_5$ | CH$_3$ |
| CH$_3$ | SCH$_3$ | CH$_2$C$_6$H$_5$ | COO—n-C$_4$H$_9$ | H |
| C$_2$H$_5$ | OC$_2$H$_5$ | CH$_3$ | COOC$_7$H$_7$ | CH$_3$ |

PREPARATION J

3-[(3,5-Dimethoxy-N-ethoxycarbonyl)anilino]propionic Acid

Methyl 3-[(3,5-dimethoxy-N-ethoxycarbonyl)anilino]propionate (2.72 g., 8.36 mmoles), aqueous sodium hydroxide (8.4 ml. of 1 N) and ethanol (8.4 ml.) are combined and stirred overnight under nitrogen at room temperature. The reaction mixture is then concentrated under reduced pressure to half-volume, diluted with water (35 ml.) and then extracted with ethyl acetate. The aqueous phase is acidified to pH 2 with 10% hydrochloric acid and extracted with methylene chloride (3×50 ml.). The combined extracts are washed with brine, dried (MgSO$_4$) and concentrated to give the product as an oil (2.47 g.) which is used as is.

In like manner, the remaining compounds of Preparation I are hydrolyzed to their corresponding alkanoic acids having the formula

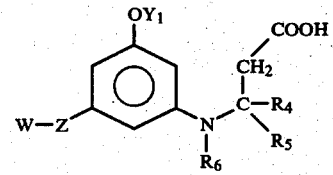

PREPARATION K

1-Carbethoxy-5,7-dimethoxy-4-oxo-1,2,3,4-tetrahydroquinoline

A mixture of 3-[(3,5-dimethoxy-N-ethoxycarbonyl)anilino]propionic acid (1.10 g., 3.7 mmole) and polyphosphoric acid (4 g.) is heated at 65° C. for 45 minutes under an atmosphere of nitrogen and is then cooled to 0° C. It is then taken up in a mixture of methylene chloride-water (200 ml. of 1:1). The organic layer is separated and the aqueous phase extracted again with methylene chloride (2×100 ml.). The combined extracts are washed with saturated sodium bicarbonate (3×100 ml.), brine (1×100 ml.) and then dried (MgSO$_4$). Concentration of the dried extract gives the product as an oil which crystallizes from benzene. Yield=645 mg., m.p. 109°–111° C.

Analysis: Calcd for C$_{14}$H$_{17}$O$_5$N: C, 60.21; H, 6.14; N, 5.02%. Found: C, 60.11; H, 6.14; N, 4.80%.

PREPARATION L 5,7-Dihydroxy-4-oxo-1,2,3,4-tetrahydroquinoline

A mixture of glacial acetic acid (60 ml.), 48% hydrobromic acid (60 ml.) and 1-carbethoxy-5,7-dimethoxy-4-oxo-1,2,3,4-tetrahydroquinoline (4.0 g., 14.3 mmole) is refluxed overnight and is then concentrated in vacuo to a dark oil. The oil is dissolved in water (50 ml.) and the aqueous solution neutralized to pH 6–7 with 1 N sodium hydroxide. A saturated solution of salt water (50 ml.) is added and the resulting mixture extracted with ethyl acetate (3×150 ml.). The extracts are combined, dried (MgSO4) and concentrated under reduced pressure to an oil. The oil is taken up in benzene-ethyl acetate (1:1) and the solution charged to a silica gel column. The column is eluted with a volume of benzene equal to the volume of the column and then with benzene-ethyl acetate (250 ml. of 4:1) and benzene-ethyl acetate (250 ml. of 1:1). Fractions (75 ml.) are collected. Fractions 4–9 are combined and evaporated under reduced pressure. The oily residue is crystallized from ethanol-hexane (1:10). Yield=1.86 g., m.p. 166°–169° C. Further recrystallization raises the melting point to 171°–172.5° C. m/e-179 (m+)

Analysis: Calcd for $C_9H_9O_3N$: C, 60.33; H, 5.06; N, 7.82%. Found: C, 60.25; H, 4.94; N, 7.55%.

By means of the procedure of Preparation K and this procedure, 3-{[3-hydroxy-5-(5-phenyl-2-pentyl)-N-ethoxycarbonyl]anilino}propionic acid is transformed to 5-hydroxy-7-(5-phenyl-2-pentyl)-4-oxo-1,2,3,4-tetrahydroquinoline, and the following compounds are prepared from compounds of Preparation J:

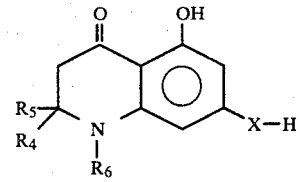

| $R_6$ | $R_4$ | X—H | $R_5$ |
|---|---|---|---|
| H | $C_2H_5$ | OH | H |
| H | H | SH | H |
| H | $CH_3$ | SH | H |
| H | $C_2H_5$ | SH | H |
| $CH_3$ | H | OH | H |
| $CH_3$ | $CH_3$ | OH | H |
| $C_2H_5$ | $CH_3$ | OH | H |
| $n-C_4H_9$ | $CH_3$ | OH | H |
| $i-C_3H_7$ | H | SH | H |
| $CH_2C_6H_5$ | $CH_3$ | OH | H |
| $(CH_2)_2C_6H_5$ | $CH_3$ | OH | H |
| $(CH_2)_4C_6H_5$ | $CH_3$ | OH | H |
| $CH_3$ | H | SH | H |
| $CH_3$ | $C_2H_5$ | OH | H |
| $CH_2C_6H_5$ | $CH_3$ | SH | H |
| $(CH_2)_3C_6H_5$ | $C_2H_5$ | SH | H |
| $C_2H_5$ | H | OH | H |
| $CH_3$ | $CH_3$ | SH | H |
| H | $CH_3$ | OH | $CH_3$ |
| H | $C_2H_5$ | OH | $C_2H_5$ |
| H | $CH_3$ | OH | $C_2H_5$ |
| $n-C_6H_{13}$ | $CH_3$ | OH | H |
| H | $CH_3$ | SH | $CH_3$ |
| H | $C_2H_5$ | SH | $C_2H_5$ |
| $CH_2COOH$ | H | OH | H |
| $CH_2COOH$ | $C_2H_5$ | OH | H |
| $CH_2COOH$ | $CH_3$ | OH | H |
| $(CH_2)_2COOH$ | H | SH | H |
| $(CH_2)_3COOH$ | $CH_3$ | SH | H |
| $(CH_2)_4COOH$ | $CH_3$ | OH | H |
| H | $n-C_3H_7$ | OH | H |
| H | $n-C_4H_9$ | SH | H |
| H | $n-C_6H_{13}$ | OH | H |
| H | $CH_3$ | OH | $CH_3$ |
| H | $n-C_4H_9$ | OH | $CH_3$ |
| H | $n-C_4H_9$ | OH | $C_2H_5$ |
| H | $n-C_6H_{13}$ | OH | $CH_3$ |
| H | $CH_2C_6H_5$ | OH | $CH_3$ |
| H | $(CH_2)_2C_6H_5$ | OH | $CH_3$ |
| H | $(CH_2)_4C_6H_5$ | OH | $CH_3$ |
| H | $CH_2C_6H_5$ | SH | $CH_3$ |
| H | $(CH_2)_3C_6H_5$ | SH | $C_2H_5$ |
| $CH_3$ | $CH_3$ | OH | $CH_3$ |
| $n-C_3H_7$ | $CH_3$ | OH | $CH_3$ |
| $n-C_6H_{13}$ | $CH_3$ | OH | $CH_3$ |
| $n-C_4H_9$ | $CH_2C_6H_5$ | OH | $CH_3$ |
| $CH_3$ | $n-C_4H_9$ | OH | $CH_3$ |
| $CH_2C_6H_5$ | $CH_3$ | OH | $CH_3$ |
| $(CH_2)_4C_6H_5$ | $CH_3$ | OH | $CH_3$ |
| $CH_2C_6H_5$ | $(CH_2)_3C_6H_5$ | OH | $CH_3$ |
| $CH_2COOH$ | $CH_3$ | OH | $CH_3$ |
| $(CH_2)_2COOH$ | $CH_3$ | OH | $CH_3$ |
| $(CH_2)_4COOH$ | $C_2H_5$ | OH | $CH_3$ |
| $CH_2COOH$ | $C_2H_5$ | OH | $CH_3$ |
| $CH_2C_6H_5$ | $CH_3$ | SH | $CH_3$ |
| $(CH_2)_3C_6H_5$ | $CH_3$ | SH | $CH_3$ |
| $CH_3$ | $CH_3$ | SH | $CH_3$ |
| $CH_3$ | $CH_2C_6H_5$ | SH | $CH_3$ |
| $i-C_3H_7$ | $n-C_4H_9$ | SH | $C_2H_5$ |
| $CH_2COOH$ | $(CH_2)_2C_6H_5$ | SH | $C_2H_5$ |
| $n-C_5H_{11}$ | $CH_3$ | SH | $CH_3$ |
| $(CH_2)_4COOH$ | $CH_3$ | SH | $CH_3$ |
| $CH_2C_6H_5$ | $(CH_2)_3C_6H_5$ | SH | $CH_3$ |
| H | $n-C_6H_{13}$ | SH | $CH_3$ |
| $CH_2C_6H_5$ | $C_2H_5$ | OH | H |
| $n-C_4H_9$ | $C_2H_5$ | OH | H |
| $CH_2C_6H_5$ | H | OH | H |
| $(CH_2)_2COOH$ | $CH_3$ | SH | H |
| $(CH_2)_4COOH$ | H | OH | H |
| H | $CH_2C_6H_5$ | SH | H |
| $i-C_3H_7$ | $CH_3$ | SH | $CH_3$ |
| $(CH_2)_3C_6H_5$ | $CH_3$ | SH | $CH_3$ |

PREPARATION M dl-1-Carbethoxy-5,7-dimethoxy-2-methyl-4-oxo-1,2,3,4-tetrahydroquinoline A solution of 3-[(3,5-dimethoxy-N-ethoxycarbonyl)anilino]butyric acid (4.0 g., 12.8 mmole) in chloroform (2 ml.) is added dropwise with stirring to polyphosphoric acid (5.0 g.) heated to 60° C. on a steam bath. The reaction mixture is held at 60°–65° C. for two hours and is then poured into a mixture of ice (100 g.) and ethyl acetate (100 ml.). The aqueous layer is further extracted with ethyl acetate (2×100 ml.) and the combined organic extracts washed successively with saturated sodium bicarbonate solution (3×100 ml.), brine (1×100 ml.), and then dried over anhydrous magnesium sulfate. Concentration of the dried extract under reduced pressure gives 2.6 g. of crude product.

Purification is accomplished by column chromatography of a benzene solution of the crude product (2.5 g.) on silica gel (95 g.). The column is eluted with a volume of benzene equal to one-half the volume of the column, followed by benzene/ethyl acetate (1:1). Fractions (40 ml.) are collected. Fractions 9–18 are combined and evaporated in vacuo to give 1.55 g. of product which is purified further by recrystallization from petroleum ether-1.33 g., m.p. 92.5°–94° C.

Recrystallization of this product from hot ethyl acetate/hexane (1:1) affords an analytical sample; m.p. 94°–95° C.

Analysis: Calcd for $C_{15}H_{12}O_5N$: C, 61.42; H, 6.53; N, 4.78%. Found: C, 61.54; H, 6.55; N, 4.94%.

m/e-293 (m+)

IR (KBr)—5.85, 5.95μ (>=O)

PREPARATION N dl-5,7-Dihydroxy-2-methyl-4-oxo-1,2,3,4-tetrahydroquinoline

Method A

A mixture of glacial acetic acid (240 ml.), 48% hydrobromic acid (240 ml.) and 1-carbethoxy-5,7-dimethyox-2-methyl-4-oxo-1,2,3,4-tetrahydroquinoline (16.0 g., 55 mmole) is refluxed overnight and is then concentrated in vacuo to a dark oil. The oil is dissolved in water (200 ml.) and the aqueous solution neutralized to pH 6–7 with 1 N sodium hydroxide. A saturated solution of salt water (200 ml.) is added and the resulting mixture extracted with ethyl acetate (3×500 ml.). The extracts are combined, dried ($MgSO_4$) and concentrated under reduced pressure to a dark oil (12.8 g.). Hexane-ethyl acetate (10:1) is added to the oil and the resulting crystals recovered by filtration (3.8 g.); m.p. 158°–165° C. Trituration of the crystals in ethyl acetate gives 1.65 g. of product; m.p. 165°–168° C.

Additional material separates from the mother liquors on standing (2.9 g.); m.p. 168°–170° C. Column chromatography of the filtrate on silica gel using benzeneether (1:1) as solvent gives an additional 4.6 g. of product, m.p. 167°–169° C.

Further purification is achieved by recrystallizing the product from ethyl acetate; m.p. 173°–174° C.

Analysis: Calcd for $C_{10}H_{11}O_3N$: C, 62.16; H, 5.74; N, 7.25%. Found: C, 62.00; H, 5.83; N, 7.14%.

m/e-193 (m+).

Method B

A mixture of dl-3-[(3,5-dimethoxy-N-ethoxycarbonyl)anilino]butyric acid (100 g., 0.32 mole) and 48% hydrobromic acid (500 ml.)/glacial acetic acid (300 ml.) is heated in an oil bath at 110° C. for 2 hours. The oil-bath temperature is then increased to 145° C., and heating is continued for an additional 2 hours. During this last heating period an azeotropic mixture distills (boiling point 42°–110° C., ~200–300 ml.) and the deep-red homogeneous solution is allowed to cool to room temperature. The mixture is poured onto ice-water (3 liters) and ether (2 liters), the layers are separated and the aqueous solution is washed with ether (2×1000 ml.). The ether layers are combined and washed successively with water (2×1000 ml.), brine (1×500 ml.), saturated $NaHCO_3$ solution (4×250 ml.) and brine (1×500 ml.) and then dried ($MgSO_4$). Decolorization with charcoal and evaporation of the ether affords a yellow foam which is crystallized from ca. 300 ml. methylene chloride to give 31.3 g. (50.4%) of pure 5,7-dihydroxy-2-methyl-4-oxo-1,2,3,4-tetrahydroquinoline. Additional product can be isolatml. $CDCl_3$/0.2 ml. $CD_3SOCD_3$) (ppm): 1240 (s, 1H, $C_5$—OH), 5.72 (d, 2H, meta H), 5.38–5.60 (bs, 1H, $C_7$—OH), 3.50–4.00 (m, 1H, $C_2$H), 2.38–2.60 (m, 2H, $C_3$—$H_2$), 1.12 (d, 3H, methyl).

m/e-193 (m+)

Analysis: Calcd for $C_{10}H_{11}O_3N$: C, 62.16; H, 5.74; N, 7.25%. Found: C, 62.01; H, 5.85; N, 7.02%.

Similarly, methyl dl-3-{[3-hydroxy-5-(5-phenyl-2-pentyl)]anilino}propionate is converted to dl-5-hydroxy-7-(5-phenyl-2-pentyl)-4-oxo-1,2,3,4-tetrahydroquinoline which is purified by column chromatography using silica gel and benzene/ether (5:1) as eluant.

m/e-309 (m+)

$^1$H NMR (60 MHz) $\delta_{CDCl_3}^{TMS}$ (ppm): 12.22 (s, 1H, 5OH), 7.14 (s, 5H, $C_6H_5$), 6.04 (d, J=2.5 Hz, 1H meta H), 5.87 (d, J=2.5 Hz, 1H meta H), 4.19–4.60 (b, 1H, NH), 3.48 (t, 2H, $CH_2N$), 2.18–2.89 (m, 5H, ArCH, $ArCH_2$, $CH_2$—C=O), 1.38–1.86 (m, 4H, —[$CH_2$]$_2$—), 1.13 (d, 3H, $CH_3$).

and ethyl dl-3-(3,5-dimethoxyanilino)hexanoate hydrochloride is converted to dl-5,7-dihydroxy-2-propyl-4-oxo-1,2,3,4-tetrahydroquinoline; m.p. 117°–119° C. (from methylene chloride).

m/e-221 (m+), 135 (base peak, m+-propyl).

and 1,3-[(3,5-dimethoxy-(N-ethoxycarbonyl)anilino]butyric acid is converted to d-5,7-dihydroxy-2-methyl-4-oxo-1,2,3,4-tetrahydroquinoline, m.p. 167°–168° C.

[alpha]$_D^{25}$ = +167.8° (c=1.0, $CH_3OH$).

m/e-193 (m+)

Analysis: Calcd for $C_{10}H_{11}O_3N$: C, 62.16; H, 5.74; N, 7.25%. Found: C, 61.87; H, 5.62; N, 6.96%.

and d-3-[3,5-dimethoxy-(N-ethoxycarbonyl)anilino]butyric acid is converted to l-5,7-dihydroxy-2-methyl-4-oxo-1,2,3,4-tetrahydroquinoline; m.p. 166°–168° C.

[alpha]$_D^{25}$ = −168.5° (c=1.0, $CH_3OH$).

m/e-193 (m+)

Analysis: Calcd for $C_{10}H_{11}O_3N$: C, 62.16; H, 5.74; N, 7.25%. Found: C, 61.82; H, 5.83; N, 7.22%.

PREPARATION O

Following the procedures of Preparations H–N, the compounds tabulated below are prepared from appropriate 3-hydroxy-5-(Z-W)anilines and appropriate esters of the formula $R_4R_5C=CH—COOCH_3$ wherein each of $R_4,R_5$ is hydrogen, methyl or ethyl.

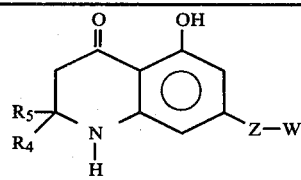

| $R_5$ | $R_4$ | Z | W |
| --- | --- | --- | --- |
| H | H | $CH(CH_3)(CH_2)_3$ | $C_6H_5$ |
| H | $CH_3$ | $CH(CH_3)(CH_2)_3$ | $C_6H_5$ |
| H | $C_2H_5$ | $CH(CH_3)(CH_2)_3$ | $C_6H_5$ |
| H | $CH_3$ | $CH(CH_3)(CH_2)_4$ | $C_6H_5$ |

-continued

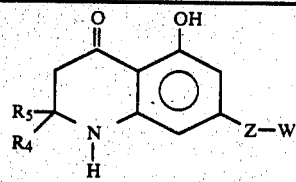

| R5 | R4 | Z | W |
|---|---|---|---|
| H | H | CH(CH3)(CH2)3 | C6H5 |
| H | H | (CH2)3 | C6H5 |
| H | H | (CH2)4 | C6H5 |
| H | C2H5 | (CH2)4 | C6H5 |
| H | H | (CH2)2CH(C2H5) | C6H5 |
| H | CH3 | CH(C2H5)(CH2)3 | C6H5 |
| H | H | C(CH3)2 | C6H5 |
| H | CH3 | C(CH3)2(CH2)3 | C6H5 |
| H | H | (CH2)6 | C6H5 |
| H | CH3 | (CH2)8 | C6H5 |
| H | H | CH(CH3)(CH2)7 | C6H5 |
| H | H | CH2 | C6H5 |
| H | H | CH(CH3)(CH2)3 | 4-FC6H4 |
| H | CH3 | CH(CH3)(CH2)3 | 4-FC6H4 |
| H | H | CH(CH3)CH2 | 4-FC6H4 |
| H | C2H5 | CH(CH3)CH2 | 4-FC6H4 |
| H | C2H5 | CH(CH3)(CH2)2 | 4-ClC6H4 |
| H | H | CH(CH3)(CH2)2CH(CH3) | C6H5 |
| H | CH3 | CH2 | C6H5 |
| H | H | (CH2)3 | C5H9 |
| CH3 | CH3 | CH(CH3)(CH2)3 | C6H5 |
| H | CH3 | CH(CH3)CH2 | C5H9 |
| H | H | CH(CH3)(CH2)2 | C5H9 |
| H | H | CH(CH3)(CH2)4 | C5H9 |
| H | H | CH(CH3)CH2 | C3H5 |
| H | H | CH(CH3)CH(CH3) | C6H11 |
| H | C2H5 | CH(CH3)CH(CH3) | C6H11 |
| H | H | CH(CH3)(CH2)5 | C6H11 |
| H | CH3 | CH(CH3)(CH2)5 | C6H11 |
| H | H | (CH2)4 | C3H5 |
| H | H | (CH2)8 | C6H11 |
| H | C2H5 | (CH2)8 | C6H11 |
| H | H | (CH2)3CH(CH3) | C6H11 |
| H | CH3 | CH(CH3)(CH2)3 | C6H11 |
| H | H | CH(CH3)(CH2)2CH(CH3) | C6H11 |
| H | CH3 | CH(CH3)CH(CH3)CH2 | C6H11 |
| H | H | (CH2)3 | 2-pyridyl |
| H | H | (CH2)3 | 4-pyridyl |
| H | H | (CH2)4 | 2-pyridyl |
| H | CH3 | (CH2)4 | 4-pyridyl |
| H | C2H5 | (CH2)4 | 3-pyridyl |
| H | CH3 | CH2CH(CH3)CH2 | 4-pyridyl |
| H | C2H5 | CH(CH3)(CH2)2 | 3-pyridyl |
| H | CH3 | CH(CH3)CH(C2H5)CH2 | 4-pyridyl |
| H | H | CH(C2H5)(CH2)3 | 3-pyridyl |
| H | H | CH2CH(C2H5)CH2 | 3-pyridyl |
| H | H | CH(CH3)(CH2)2 | 4-piperidyl |
| H | CH3 | CH(C2H5)(CH2)2 | 2-piperidyl |
| H | CH3 | CH(CH3)(CH2)2CH(CH3) | 4-piperidyl |
| H | CH3 | CH(CH3)(CH2)2 | C7H13 |
| H | H | CH(CH3)(CH2)2 | C7H13 |
| H | CH3 | CH(CH3)CH2—O—(CH2)2 | C6H5 |
| H | H | (CH2)4 | CH3 |
| H | CH3 | CH(CH3)CH(CH3)(CH2)5 | H |
| H | H | CH(CH3)CH(CH3)(CH2)5 | H |
| H | H | CH2 | H |
| H | CH3 | CH2 | CH3 |
| H | H | (CH2)3 | CH3 |
| H | H | (CH2)6 | CH3 |
| H | CH3 | (CH2)6 | CH3 |
| H | H | CH(CH3) | CH3 |
| H | CH3 | (CH2)3 | H |
| H | H | CH(CH3) | C6H11 |
| H | C2H5 | CH(CH3)(CH2)4 | CH3 |
| H | H | (CH2)3—O— | C6H5 |
| H | CH3 | (CH2)3—O— | 4-FC6H4 |
| H | CH3 | (CH2)3—O— | C6H11 |
| H | C2H5 | (CH2)3—O— | C4H7 |
| H | H | (CH2)3—O— | CH3 |
| H | CH3 | (CH2)3—O— | 4-(4-FC6H4)C6H10 |
| H | C2H5 | (CH2)3—O—(CH2)2 | 4-ClC6H4 |
| H | H | (CH2)3—O—(CH2)2 | C6H5 |

-continued

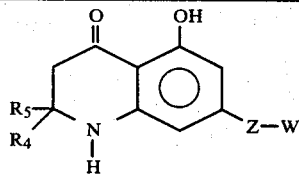

| R5 | R4 | Z | W |
|---|---|---|---|
| H | CH3 | (CH2)3—O—CH(CH3) | 4-piperidyl |
| H | CH3 | (CH2)3—O—CH(CH3)(CH2)2 | C6H5 |
| H | H | (CH2)3—O—CH(CH3)(CH2)2 | CH3 |
| H | H | CH(CH3)(CH2)2—O— | C6H5 |
| H | CH3 | CH(CH3)(CH2)2—O—CH2 | CH3 |
| H | CH3 | CH(CH3)(CH2)2—O—(CH2)4 | C6H5 |
| H | CH3 | CH(CH3)(CH2)2—O—CH(CH3) | C7H13 |
| H | H | CH(CH3)(CH2)2—O—CH2CH—(C2H5) | CH3 |
| H | CH3 | (CH2)4—O— | C6H5 |
| H | H | (CH2)4—O—CH(CH3)CH2 | 3-piperidyl |
| H | C2H5 | (CH2)4—O—(CH2)5 | 4-pyridyl |
| H | C2H5 | (CH2)4—O—CH2 | 4-FC6H4 |
| H | H | CH(CH3)(CH2)3—O— | 2-(4-FC6H4)C5H8 |
| H | CH3 | CH(CH3)(CH2)3—O—(CH2)2 | C6H5 |
| H | C2H5 | CH(CH3)(CH2)3—O—(CH2)2 | CH3 |
| H | H | CH(C2H5)(CH2)2—O—(CH2)4 | C6H5 |
| H | CH3 | CH(C2H5)(CH2)2—O—CH(CH3) | 4-piperidyl |
| H | H | CH(C2H5)(CH2)2—O—(CH2)2—CH(CH3) | C7H13 |
| H | CH3 | CH(CH3)—O—CH2 | C5H9 |
| H | CH3 | CH(C2H5)(CH2)2—O— | C3H5 |
| H | H | CH(C2H5)(CH2)2—O— | 2-(4-FC6H4)C7H12 |
| H | H | (CH2)3—S— | C6H5 |
| H | C2H5 | (CH2)3—S—CH2 | 4-FC6H4 |
| H | CH3 | (CH2)3—S— | C5H9 |
| H | C2H5 | (CH2)3—S—(CH2)2 | CH3 |
| H | H | (CH2)3—S—(CH2)4 | C6H5 |
| H | CH3 | CH(CH3)(CH2)2—S— | 4-piperidyl |
| H | CH3 | CH(CH3)(CH2)2—S— | 4-(C6H5)C6H10 |
| H | CH3 | CH(CH3)(CH2)2—S—(CH2)4 | 4-pyridyl |
| H | CH3 | CH(CH3)(CH2)2—S—(CH2)4 | C6H5 |
| H | C2H5 | CH(C2H5)(CH2)2—S— | C6H11 |
| H | CH3 | CH(C2H5)(CH2)2—S—(CH2)2—CH(CH3) | CH3 |
| H | H | CH(C2H5)(CH2)2—S—CH(CH3) | 4-ClC6H4 |
| H | H | CH(CH3)(CH2)3—S—(CH2)4 | 4-FC6H4 |
| H | CH3 | CH(CH3)(CH2)3—S—(CH2)4 | 4-pyridyl |
| H | H | CH(CH3)CH2—O—(CH2)6 | CH3 |
| H | CH3 | CH(CH3)CH2—O—(CH2)6 | C6H5 |
| H | H | CH(CH3)CH2—O—(CH2)4 | CH3 |
| H | H | CH(CH3)CH2—O—CH(CH3)CH2 | C6H5 |
| H | CH3 | CH(CH3)CH2—O—CH(CH3)CH2 | C6H5 |
| H | C2H5 | CH(CH3)CH2—O—CH(CH3)CH2 | C6H5 |
| H | CH3 | CH(CH3)CH2—O—CH2 | 4-FC6H4 |
| H | CH3 | CH(CH3)CH2—O—(CH2)2 | 4-pyridyl |
| H | H | CH(CH3)CH2—O—CH(CH3) | CH3 |
| H | H | CH2CH(CH3)—O—CH2 | CH3 |
| H | C2H5 | CH2CH(CH3)—O—CH2 | CH3 |
| H | CH3 | CH2CH(CH3)—O—(CH2)6 | CH3 |
| H | CH3 | CH2CH(CH3)—O—CH(CH3)CH2 | C6H5 |
| H | H | CH2CH(CH3)—O—(CH2)2 | 4-FC6H4 |
| H | CH3 | C(CH3)2(CH2)6 | H |
| H | C2H5 | C(CH3)2(CH2)6 | H |
| CH3 | CH3 | CH(CH3)(CH2)3 | C6H5 |
| C2H5 | C2H5 | CH(CH3)(CH2)3 | C6H5 |
| C2H5 | CH3 | CH(CH3)(CH2)4 | C6H5 |
| CH3 | CH3 | CH(CH3)(CH2)3 | C6H5 |
| H | CH2C6H5 | (CH2)3 | C6H5 |
| H | n-C6H13 | (CH2)4 | C6H5 |
| CH3 | C2H5 | (CH2)4 | C6H5 |
| H | (CH2)4C6H5 | (CH2)2CH(C2H5) | C6H5 |
| CH3 | CH3 | C(CH3)2 | C6H5 |
| CH3 | CH3 | C(CH3)2(CH2)3 | C6H5 |
| C2H5 | C2H5 | (CH2)6 | C6H5 |
| CH3 | CH3 | (CH2)8 | C6H5 |
| CH3 | CH3 | CH(CH3)(CH2)7 | C6H5 |
| H | n-C4H9 | CH2 | C6H5 |
| CH3 | CH3 | CH(CH3)(CH2)3 | 4-FC6H4 |
| CH3 | n-C6H13 | CH(CH3)CH2 | 4-FC6H4 |
| H | (CH2)2C6H5 | CH(CH3)(CH2)2CH(CH3) | C6H5 |
| H | CH3 | CH2 | C6H5 |

-continued

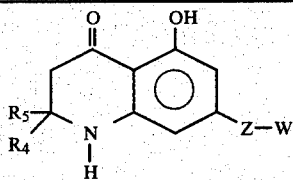

| R5 | R4 | Z | W |
|---|---|---|---|
| H | CH2C6H5 | (CH2)3 | C5H9 |
| CH3 | CH3 | CH(CH3)CH2 | C5H9 |
| CH3 | CH2C6H5 | CH(CH3)(CH2)2 | C5H9 |
| CH3 | CH3 | CH(CH3)CH2 | C3H5 |
| H | (CH2)3C6H5 | CH(CH3)(CH2)5 | C6H11 |
| CH3 | CH3 | CH(CH3)(CH2)5 | C6H11 |
| CH3 | n-C4H9 | (CH2)4 | C3H5 |
| CH3 | CH3 | (CH2)9 | C6H11 |
| CH3 | CH3 | (CH2)3 | 2-pyridyl |
| CH3 | CH2C6H5 | (CH2)3 | 4-pyridyl |
| CH3 | CH3 | (CH2)4 | 4-pyridyl |
| C2H5 | C2H5 | (CH2)4 | 3-pyridyl |
| CH3 | CH3 | CH(CH3)CH(C2H5)CH2 | 4-pyridyl |
| H | n-C5H11 | CH(C2H5)(CH2)3 | 3-pyridyl |
| H | i-C3H7 | CH(CH3)(CH2)2 | 4-piperidyl |
| CH3 | CH3 | CH(C2H5)(CH2)2 | 2-piperidyl |
| CH3 | CH3 | CH(CH3)(CH2)2CH(CH3) | 4-piperidyl |
| CH3 | CH3 | CH(CH3)(CH2)2 | C7H13 |
| H | n-C4H9 | CH(CH3)(CH2)2 | C7H13 |
| CH3 | CH3 | CH(CH3)CH2—O—(CH2)2 | C6H5 |
| CH3 | CH2C6H5 | (CH2)4 | CH3 |
| CH3 | CH3 | CH(CH3)CH(CH3)(CH2)5 | H |
| C2H5 | C2H5 | CH(CH3)CH(CH3)(CH2)5 | H |
| CH3 | CH3 | CH2 | H |
| CH3 | C2H5 | (CH2)3 | CH3 |
| H | n-C6H13 | (CH2)6 | CH3 |
| CH3 | (CH2)3C6H5 | CH(CH3) | CH3 |
| CH3 | CH3 | (CH2)3 | H |
| H | n-C4H9 | CH(CH3) | C6H11 |
| CH3 | CH3 | (CH2)3—O— | C6H5 |
| CH3 | CH3 | (CH2)3—O— | 4-FC6H4 |
| CH3 | CH3 | (CH2)3—O— | C6H11 |
| C2H5 | C2H5 | (CH2)3—O— | C4H7 |
| H | CH2C6H5 | (CH2)3—O— | CH3 |
| CH3 | CH3 | (CH2)3—O— | 4-(4-FC6H4)C6H10 |
| C2H5 | C2H5 | (CH2)3—O—(CH2)2 | 4-ClC6H4 |
| CH3 | CH3 | (CH2)3—O—CH(CH3) | 4-piperidyl |
| H | n-C5H11 | CH(CH3)(CH2)2—O— | C6H5 |
| CH3 | CH3 | CH(CH3)(CH2)2—O—CH2 | CH3 |
| CH3 | CH3 | CH(CH3)(CH2)2—O—(CH2)4 | C6H5 |
| CH3 | CH3 | CH(CH3)(CH2)2—O—CH—(CH3) | C7H13 |
| CH3 | CH3 | CH(CH3)(CH2)2—O—CH2—CH(C2H5) | CH3 |
| CH3 | CH3 | (CH2)4—O— | C6H5 |
| C2H5 | C2H5 | (CH2)4—O—CH(CH3)CH2 | 3-piperidyl |
| CH3 | C2H5 | (CH2)4—O—CH2 | 4-FC6H4 |
| H | n-C3H7 | CH(CH3)(CH2)3—O— | 2-(4-FC6H4)C5H8 |
| CH3 | CH3 | CH(CH3)(CH2)3—O—(CH2)2 | C6H5 |
| CH3 | CH3 | CH(C2H5)(CH2)2—O—CH(CH3) | 4-piperidyl |
| CH3 | CH3 | CH(C2H5)(CH2)2—O— | C3H5 |
| CH3 | CH3 | CH(C2H5)(CH2)2—O— | 2-(4-FC6H4)C7H12 |
| CH3 | CH3 | (CH2)3—S— | C6H5 |
| C2H5 | C2H5 | (CH2)3—S—CH2 | 4-FC6H4 |
| CH3 | CH3 | (CH2)3—S— | C5H9 |
| CH3 | CH2C6H5 | (CH2)3—S—(CH2)4 | C6H5 |
| CH3 | CH3 | CH(CH3)(CH2)2—S— | 4-piperidyl |
| CH3 | CH3 | CH(CH3)(CH2)2—S—(CH2)4 | 4-pyridyl |
| CH3 | CH3 | CH(CH3)(CH2)2—S—(CH2)4 | C6H5 |
| C2H5 | C2H5 | CH(C2H5)(CH2)2—SO | C6H11 |
| H | n-C6H13 | CH(C2H5)(CH2)2—S—CH(CH3) | 4-ClC6H4 |
| CH3 | n-C4H9 | CH(CH3)(CH2)3—S—(CH2)4 | 4-FC6H4 |
| CH3 | CH3 | CH(CH3)(CH2)3—S—(CH2)4 | 4-pyridyl |
| CH3 | CH3 | CH(CH3)CH2—O—(CH2)6 | C6H5 |

-continued

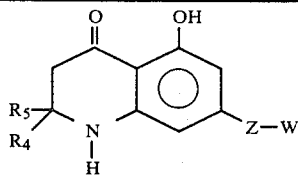

| R5 | R4 | Z | W |
|---|---|---|---|
| CH3 | CH3 | C(CH3)2(CH2)6 | H |
| C2H5 | C2H5 | C(CH3)2(CH2)6 | H |

Of course, when Z contains an ether or thioether linkage, the procedure of Preparation M is used for the cyclization step.

PREPARATION P dl-5-Hydroxy-2-methyl-7-(2-heptyloxy)-4-oxo-1,2,3,4-tetrahydroquinoline Potassium hydroxide pellets (325 mg., 52 mmole) is added to a solution of dl-5,7-dihydroxy-2-methyl-4-oxo-1,2,3,4-tetrahydroquinoline (1.0 g., 52 mmole) in N,N-dimethylformamide (10 ml.). The mixture is slowly heated to 100° C. and to the resulting solution dl-2-bromoheptane (1.08 g., 60 mmole) is added all at once with good stirring. After 10 minutes additional potassium hydroxide (160 mg.) is added followed by additional dl-2-bromoheptane (500 mg.). The addition of potassium hydroxide and dl-2-bromoheptane was repeated two more times using 80 mg. potassium hydroxide and 250 mg. dl-2-bromoheptane each time. The reaction mixture is stirred an additional 10 minutes and is then cooled. Chloroform (50 ml.) and aqueous sodium hydroxide (25 ml. of 1 N) are added, the mixture stirred for 10 minutes and the layers separated. The chloroform extraction is repeated, the extracts combined, dried (MgSO4) and concentrated under reduced pressure to a dark oil. The oil is chromatographed on silica gel (120 g.) using benzene as solvent. Fractions of 30 ml. each are collected. The 12th–18th fractions are combined and concentrated under reduced pressure to a light yellow oil (850 mg.) which crystallizes upon standing.

The desired product is separated by filtration and recrystallized from hot hexane, m.p. 76°–77° C.

The above procedure is repeated on a 20-fold scale but using benzene-ethyl acetate (9:1) as chromatographic solvent. Fractions of 750 ml. each are collected. Combination of the 2nd–6th fractions affords 32 g. of oil which partially crystallizes from hexane upon standing and cooling to give 18.2 g. of product. An additional 3.2 g. is obtained by concentrating the mother liquor and allowing it to crystallize by standing in the cold. Total yield=21.4 g.

Analysis: Calcd for $C_{17}H_{25}O_3N$: C, 70.07; H, 8.65; N, 4.81%. Found: C, 69.82; H, 8.67; N, 4.93%.

m/e-291 (m+)

IR (KBr): 6.01μ (=O)

In like manner, 5,7-dihydroxy-4-oxo-1,2,3,4-tetrahydroquinoline converted to dl-5-hydroxy-7-(2-heptyloxy)-4-oxo-1,2,3,4-tetrahydroquinoline, an oil.

$^1$H NMR (60 MHz) (CDCl3) ppm (delta): 13.3 (s, 1H, phenolic), 5.5 and 5.7 (d, 2H, J=2 Hz, aromatic), 4.6 (bs, 1H, —NH), 4.1–4.6 (m, 1H, —O—CH—), 3.3 (t, 2H, J=7 Hz, —CH2—), 2.6 (t, 2H, J=7 Hz, —CH2—), 2.0–2.7 (m, remaining protons).

PREPARATION Q

The following compounds are prepared according to the procedure of Preparation P but using the appropriate Br—(alk2)n—W reactant and the appropriate 5,7-dihydroxy-2-R4R5-4-oxo-1,2,3,4-tetrahydroquinoline or 5-hydroxy-7-thiol-2-R4R5-4-oxo-1,2,3,4-tetrahydroquinoline.

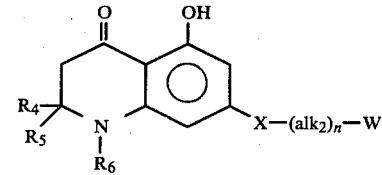

| R5 | R4 | X | —alk2— | W | R6 |
|---|---|---|---|---|---|
| H | H | O | CH2 | H | H |
| H | CH3 | O | CH2 | H | H |
| H | CH3 | O | (CH2)2 | H | H |
| H | H | O | (CH2)4 | H | CH3 |
| H | CH3 | O | (CH2)6 | H | H |
| H | CH3 | O | (CH2)9 | H | H |
| H | H | O | CH(CH)3CH2 | H | C2H5 |
| H | CH3 | O | CH(CH3)(CH2)3 | H | CH3 |
| H | H | O | CH(CH3)(CH2)4 | CH3 | H |
| H | C2H5 | O | CH2 | C6H5 | CH2C6H5 |
| H | H | O | (CH2)2 | C6H5 | CH2COOH |
| H | CH3 | O | (CH2)4 | C6H5 | CH2COOH |
| H | C2H5 | O | CH2 | 4-ClC6H4 | H |
| H | H | O | CH2 | 4-FC6H4 | H |
| H | CH3 | O | CH(CH3)CH2 | C6H5 | CH3 |
| H | H | O | CH(CH3)(CH2)2 | C6H5 | CH3 |

-continued

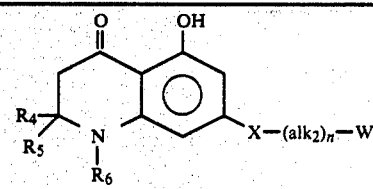

| R5 | R4 | X | —alk2— | W | R6 |
|---|---|---|---|---|---|
| H | CH3 | O | CH(CH3)(CH2)3 | C6H5 | H |
| H | C2H5 | O | (CH2)7 | C6H5 | H |
| H | H | O | CH(CH3)CH(CH3)(CH2)4 | CH3 | H |
| H | H | O | (CH2)2 | 4-pyridyl | C2H5 |
| H | CH3 | O | (CH2)3 | 4-pyridyl | H |
| H | C2H5 | O | (CH2)3 | 3-pyridyl | n-C4H9 |
| H | CH3 | O | CH(CH3)CH2 | 2-pyridyl | H |
| H | H | O | CH2 | C3H5 | H |
| H | CH3 | O | CH2 | C3H5 | H |
| H | CH3 | O | CH(CH3) | C4H7 | H |
| H | CH3 | O | (CH2)2 | C5H9 | H |
| H | CH3 | O | CH2 | C6H11 | H |
| H | CH3 | O | (CH2)3 | C6H11 | H |
| H | C2H5 | O | (CH2)3 | C5H9 | H |
| H | CH3 | O | (CH2)4 | C7H13 | H |
| H | H | O | — | C6H5 | H |
| H | CH3 | O | — | C6H5 | CH3 |
| H | H | O | — | 4-FC6H4 | H |
| H | H | O | — | 4-ClC6H4 | (CH2)2C6H5 |
| H | C2H5 | O | — | C6H5 | H |
| H | H | O | — | C5H9 | H |
| H | C2H5 | O | — | C5H9 | H |
| H | CH3 | O | — | C6H11 | H |
| H | H | O | — | C7H13 | H |
| H | H | O | — | 2-(C6H5)C3H4 | H |
| H | C2H5 | O | — | 2-(C6H5)C3H4 | CH3 |
| H | C2H5 | O | — | 4-(C6H5)C6H10 | H |
| H | H | O | — | 3-(C6H5)C7H12 | H |
| H | H | O | — | 4-pyridyl | C2H5 |
| H | CH3 | O | — | 4-pyridyl | H |
| H | C2H5 | O | — | 4-piperidyl | H |
| H | CH3 | O | — | 2-pyridyl | H |
| H | CH3 | O | — | 3-piperidyl | H |
| H | H | S | CH2 | H | H |
| H | CH3 | S | CH2 | H | H |
| H | H | S | (CH2)3 | H | (CH2)2COOH |
| H | CH3 | S | (CH2)3 | H | (CH2)2COOH |
| H | H | S | (CH2)5 | H | H |
| H | CH3 | S | (CH2)5 | H | H |
| H | C2H5 | S | (CH2)4 | H | H |
| H | H | S | (CH2)9 | H | H |
| H | CH3 | S | CH(CH3)(CH2)5 | H | (CH2)3COOH |
| H | H | S | CH(CH3)(CH2)3 | H | H |
| H | CH3 | S | CH2 | C3H5 | H |
| H | H | S | CH2 | C6H11 | H |
| H | CH3 | S | (CH2)3 | C6H11 | H |
| H | C2H5 | S | (CH2)4 | C7H13 | H |
| H | H | S | CH(CH3) | C4H7 | H |
| H | H | S | CH(CH3)CH(CH3)(CH2)4 | CH3 | H |
| H | CH3 | S | CH(CH3)CH(CH3)(CH2)4 | CH3 | H |
| H | H | S | C(CH3)2(CH2)5 | CH3 | H |
| H | CH3 | S | C(CH3)2(CH2)5 | CH3 | H |
| H | CH3 | S | CH2 | C6H5 | H |
| H | CH3 | S | (CH2)4 | C6H5 | H |
| H | H | S | CH(CH3)(CH2)2 | C6H5 | H |
| H | CH3 | S | CH(CH3)(CH2)3 | C6H5 | CH3 |
| H | CH3 | S | CH2 | 4-FC6H4 | H |
| H | H | S | CH2 | 4-ClC6H4 | H |
| H | CH3 | S | (CH2)3 | 4-pyridyl | H |
| H | C2H5 | S | CH(CH3)CH2 | 2-pyridyl | H |
| H | H | S | — | C6H5 | H |
| H | CH3 | S | — | 4-FC6H4 | H |
| H | C2H5 | S | — | C5H9 | H |
| H | CH3 | S | — | C6H11 | H |
| H | H | S | — | 4-pyridyl | H |
| H | CH3 | S | — | 4-piperidyl | CH2C6H5 |
| H | CH3 | S | — | C7H13 | H |
| H | CH3 | S | — | 2-(C6H5)C3H4 | H |
| H | CH3 | S | — | 4-(C6H5)C6H10 | H |
| H | H | S | — | 4-ClC6H4 | H |
| H | H | S | CH(CH3)(CH2)4 | CH3 | CH3 |

-continued

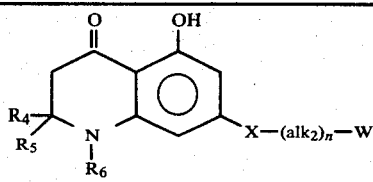

| R5 | R4 | X | —alk2— | W | R6 |
|---|---|---|---|---|---|
| H | CH3 | S | CH(CH3)(CH2)3 | C6H5 | CH3 |
| H | H | S | C(CH3)2(CH2)5 | CH3 | i-C3H7 |
| H | C2H5 | S | (CH2)4 | CH3 | (CH2)3C6H5 |
| H | CH3 | O | CH(CH3)(CH2)4 | CH3 | (CH2)4C6H5 |
| H | CH3 | O | CH(CH3)(CH2)3 | C6H5 | n-C4H9 |
| H | CH3 | O | CH(CH3)(CH2)3 | C6H5 | CH2COOH |
| H | H | O | CH(CH3)(CH2)3 | C6H5 | CH2COOH |
| H | H | O | CH(CH3)(CH2)3 | C6H5 | (CH2)4COOH |
| CH3 | CH3 | O | CH2 | H | H |
| C2H5 | CH3 | O | (CH2)4 | H | CH3 |
| CH3 | CH3 | O | (CH2)9 | H | H |
| CH3 | CH3 | O | CH(CH3)(CH2)3 | CH3 | H |
| CH3 | CH3 | O | CH(CH3)(CH2)4 | CH3 | H |
| CH3 | n-C6H13 | O | CH(CH3)CH(CH3)(CH2)4 | CH3 | H |
| C2H5 | C2H5 | O | C(CH3)2(CH2)4 | CH3 | H |
| CH3 | CH3 | O | CH(CH3)(CH2)3 | C6H5 | H |
| H | n-C6H13 | O | CH(CH3)(CH2)4 | CH3 | CH3 |
| CH3 | CH3 | O | CH(CH3)(CH2)3 | 4-FC6H4 | n-C3H7 |
| H | CH3 | O | CH(CH3)(CH2)4 | CH3 | n-C6H13 |
| H | C2H5 | O | CH(CH3)(CH2)3 | CH3 | CH2COOH |
| H | CH3 | O | CH(CH3)(CH2)3 | 4-ClC6H4 | (CH2)4COOH |
| CH3 | CH3 | O | (CH2)3 | 4-pyridyl | CH2C6H5 |
| CH3 | CH2C6H5 | O | CH(CH3)(CH2)3 | 3-pyridyl | H |
| CH3 | n-C4H9 | O | — | C6H5 | H |
| CH3 | (CH2)3C6H5 | O | — | 4-FC6H4 | CH2C6H5 |
| CH3 | CH3 | O | — | 4-pyridyl | (CH2)4C6H5 |
| CH3 | CH3 | O | — | C5H9 | H |
| C2H5 | C2H5 | O | — | C7H13 | H |
| H | C2H5 | O | — | 3-piperidyl | H |
| CH3 | CH3 | O | — | 2-(C6H5)C3H4 | CH3 |
| CH3 | CH3 | O | — | 3-(C6H5)C7H12 | H |
| CH3 | CH3 | O | CH2 | C3H5 | H |
| CH3 | CH3 | O | (CH2)3 | C6H11 | (CH2)2COOH |
| CH3 | C2H5 | O | (CH2)4 | C7H13 | (CH2)4COOH |
| CH3 | CH3 | S | — | C6H5 | n-C5H11 |
| CH3 | CH3 | S | — | 4-ClC6H4 | H |
| CH3 | CH3 | S | — | C7H13 | H |
| CH3 | CH3 | S | — | 4-(C6H5)C6H10 | H |
| H | n-C4H9 | S | — | C6H5 | H |
| CH3 | (CH2)3C6H5 | S | — | 4-pyridyl | CH2C6H5 |
| CH3 | CH2C6H5 | S | — | C6H11 | CH3 |
| C2H5 | (CH2)2C6H5 | S | — | 4-FC6H4 | CH2COOH |
| CH3 | CH3 | S | — | 4-(C6H5)C6H10 | (CH2)4COOH |
| CH3 | n-C6H13 | S | — | C6H5 | H |
| CH3 | CH2C6H5 | S | — | C6H5 | H |
| C2H5 | C2H5 | S | CH2 | H | H |
| CH3 | CH3 | S | (CH2)5 | H | CH3 |
| CH3 | CH3 | S | (CH2)9 | H | i-C3H7 |
| CH3 | CH3 | S | C(CH3)2(CH2)6 | H | (CH2)3C6H5 |
| CH3 | CH3 | S | CH(CH3)(CH2)4 | CH3 | CH2C6H5 |
| CH3 | CH3 | S | CH(CH3)(CH2)3 | C6H5 | H |
| C2H5 | n-C4H9 | S | CH(CH3)(CH2)3 | C6H11 | i-C3H7 |
| H | CH2C6H5 | S | C(CH3)2(CH2)6 | H | H |
| CH3 | (CH2)2C6H5 | S | — | H | H |
| H | n-C3H7 | O | C(CH3)2(CH2)6 | H | H |
| C2H5 | n-C4H9 | O | CH2 | 4-pyridyl | H |
| CH3 | (CH2)4C6H5 | O | (CH2)4 | CH3 | H |
| C2H5 | (CH2)3C6H5 | S | — | C6H5 | H |
| CH3 | CH3 | O | CH2 | C6H5 | n-C6H13 |
| CH3 | CH2C6H5 | O | (CH2)6 | 4-FC6H4 | n-C4H9 |
| CH3 | n-C4H9 | O | CH(CH3)(CH2)3 | H | CH3 |
| CH3 | CH3 | O | C(CH3)2(CH2)5 | CH3 | CH2COOH |

PREPARATION R dl-5-Hydroxy-2-methyl-7-(5-phenyl-2-pentyloxy)-4-oxo-1,2,3,4-tetrahydroquinoline A mixture of 5-phenyl-2-(R,S)-pentanol (16.4 g., 100 mmole), triethylamine (28 ml., 200 mmole) and dry tetrahydrofuran (80 ml.) under a nitrogen atmosphere is cooled in an ice/water bath. Methanesulfonyl chloride (8.5 ml., 110 mM) in dry tetrahydrofuran (20 ml.) is added dropwise at such a rate that the temperature holds essentially constant. The mixture is allowed to warm to room temperature and is then filtered to remove triethylamine hydrochloride. The filter cake is washed with dry tetrahydrofuran and the combined wash and filtrate evaporated under reduced pressure to give the product as an oil. The oil is dissolved in chloroform (100 ml.) and the solution washed with water (2×100 ml.) and then with saturated brine (1×20 ml.). Evaporation of the solvent affords 21.7 g. (89.7%) yield of the mesylate of dl-5-phenyl-2-pentanol which is used in the next step without further purification.

A mixture of dl-5,7-dihydroxy-2-methyl-4-oxo-1,2,3,4-tetrahydroquinoline (1.0 g., 5.2 mmole), potassium carbonate (14.35 g., 0.104 mole), N,N-dimethylformamide (60 ml.) and dl-5-phenyl-2-pentanol mesylate (13.68 g., 57 mmole), under a nitrogen atmosphere, is heated to 80°–82° C. in an oil bath for 1.75 hours. The mixture is cooled to room temperature and then poured into ice/water (300 ml.). The aqueous solution is extracted with ethyl acetate (2×50 ml.) and the combined extracts washed successively with water (3×50 ml.) and saturated brine (1×50 ml.). The extract is then dried ($MgSO_4$), decolorized with charcoal and evaporated to give the product.

m/e-339 (m+)

The above procedure is repeated but using 114.8 g. (0.594 mole) of dl-5,7-dihydroxy-2-methyl-4-oxo-1,2,3,4-tetrahydroquinoline, 612 ml. of N,N-dimethylformamide, 174.8 g. (1.265 moles) of potassium carbonate and 165.5 g. (0.638 mole) of dl-5-phenyl-2-pentanol mesylate. The reaction mixture is cooled and poured onto ice water (4 liters) and the aqueous solution extracted with ethyl acetate (2×4 liters). The combined extract is washed with water (4×2 liters), brine (1×2 liters) and dried ($MgSO_4$). Evaporation affords 196 g. of the title product. It is used without further purification.

$^1H$ NMR (60 MHz) ($CDCl_3$) ppm (delta): 12.73 (s, 1H, OH), 7.22 (s, 5H, aromatic), 5.80 (d, J=3 $H_3$, 1H, meta H), 5.58 (d, J=3 $H_3$, 1H, meta H), 1.25 (d, 6H, $CH_3$—CH—N and $CH_3$—CH—O—), 1.41–4.81 (m, 11H, remaining protons).

PREPARATION S dl-5-Hydroxy-7-(5-phenyl-2-pentyloxy)-4-oxo-1,2,3,4-tetrahydroquinoline Repetition of the procedure of Preparation R but using 5,7-dihydroxy-4-oxo-1,2,3,4-tetrahydroquinoline in place of the 5,7-dihydroxy-2-methyl-4-oxo-1,2,3,4-tetrahydroquinoline affords dl-5-hydroxy-7-(5-phenyl-2-pentyloxy)-4-oxo-1,2,3,4-tetrahydroquinoline as an oil in 74% yield.

m/e-325 (m+)

Analysis: Calcd for $C_{20}H_{23}NO_3$: C, 73.70; H, 7.12; N, 4.31%. Found: C, 73.69; H, 7.15; N, 4.08%.

$^1H$ NMR (60 MHz) ($CDCl_3$) ppm (delta): 12.6 (bs, 1H, phenolic), 7.3 (s, 5H, aromatic), 5.8 (d, 1H, aromatic, J=2 Hz), 5.6 (d, 1H, aromatic, J=2 Hz), 4.7–4.1 (m, 2H, NH and O—CH), 3.5 (t, 2H, $CH_2$, J=7 Hz), 3.1–2.1 (m, 4H, 2—$CH_2$—), 2.1–1.5 (m, 4H, 2—$CH_2$), 1.3 (d, 3H, —CH—$CH_3$, J=6 Hz).

Similarly, dl-5,7-dihydroxy-2-methyl-4-oxo-1,2,3,4-tetrahydroquinoline (27 g., 0.14 mole) is alkylated with 4-phenylbutyl methanesulfonate (35.2 g., 0.154 mole) to yield 41.1 g. (90%) of the desired dl-5-hydroxy-2-methyl-7-(4-phenylbutyloxy)-4-oxo-1,2,3,4-tetrahydroquinoline, m.p. 88°–90° C. Recrystallization from ethyl acetate/hexane (1:2) gives the analytical sample, m.p. 90°–91° C.

Analysis: Calcd for $C_{20}H_{23}O_3N$; C, 73.82; H, 7.12; N, 4.30%. Found: C, 73.60; H, 7.09; N, 4.26%.

m/e-325 (m+)

$^1H$ NMR (60 MHz) ($CDCl_3$) ppm (delta): 12.58 (s, 1H, —OH), 7.21 (s, 5H, $C_6H_5$), 5.74 (d, J=2.5 Hz, 1H, meta H), 5.5 (d, J=2.5 Hz, 1H, meta H), 4.36 (bs, 1H, NH), 3.33–4.08 (m, 3H, —O—$CH_2$, —CH—N), 2.29–2.83 (m, 4H, —$CH_2$—C=O, $C_6H_5$—$CH_2$), 1.51–1.92 (m, 4H, —$[CH_2]_2$), 1.23 (d, 3H, $CH_3$—).

In the like manner, alkylation of d-5,7-dihydroxy-4-oxo-1,2,3,4-tetrahydroquinoline with d-2-octylmethanesulfonate gives d-5-hydroxy-2-methyl-7-(2-(R)-octyloxy)-4-oxo-1,2,3,4-tetrahydroquinoline, m.p. 64°–68° C.

$[alpha]_D^{25}$ = +110.2° (c=1.0, $CHCl_3$).

and alkylation of dl-5,7-dihydroxy-2-propyl-4-oxo-1,2,3,4-tetrahydroquinoline with dl-5-phenyl-2-pentanol mesylate gives dl-5-hydroxy-7-(5-phenyl-2-pentyloxy)-2-propyl-4-oxo-1,2,3,4-tetrahydroquinoline; m/e-367 (m+).

PREPARATION T

The following compounds are prepared from appropriate reactants by the procedures of Preparations P and R.

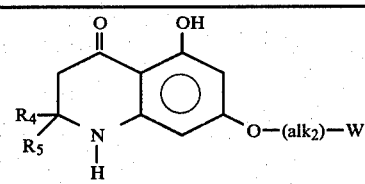

| $R_5$ | $R_4$ | $alk_2$ | W |
|---|---|---|---|
| H | $CH_3$ | $CH_2C(CH_3)_2(CH_2)_4$ | $CH_3$ |
| H | $CH_3$ | $CH_2CH(CH_3)(CH_2)_2CH(CH_3)CH_2$ | $CH_3$ |
| H | $CH_3$ | $CH(CH_3)CH_2CH(CH_3)CH_2CH(CH_3)$ | $CH_3$ |
| H | H | $CH(CH_3)(CH_2)_2C(CH_3)_2$ | $CH_3$ |
| H | $C_2H_5$ | $CH_2CH(C_2H_5)$ | $C_6H_5$ |
| H | $CH_3$ | $CH_2CH_2CH(CH_3)$ | $C_6H_5$ |
| H | $CH_3$ | $(CH_2)_7$ | $C_6H_5$ |
| H | H | $CH(CH_3)(CH_2)_5$ | $C_6H_5$ |
| H | $C_2H_5$ | $(CH_2)_9$ | $C_6H_5$ |
| H | H | $(CH_2)_9$ | $CH_3$ |
| H | H | $CH(CH_3)CH_2$ | 2-pyridyl |
| H | $C_2H_5$ | $(CH_2)_2$ | 2-pyridyl |
| H | $C_2H_5$ | $(CH_2)_4$ | 2-pyridyl |
| H | H | $(CH_2)_3$ | 2-piperidyl |
| H | $CH_3$ | $(CH_2)_3$ | 4-piperidyl |

-continued

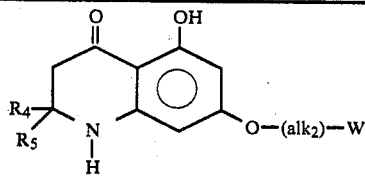

| R5 | R4 | alk2 | W |
|---|---|---|---|
| H | CH$_3$ | (CH$_2$)$_3$ | 4-FC$_6$H$_4$ |
| H | H | (CH$_2$)$_3$ | 4-ClC$_6$H$_4$ |
| H | C$_2$H$_5$ | (CH$_2$)$_4$ | 4-FC$_6$H$_4$ |
| H | H | CH(CH$_3$)(CH$_2$)$_2$ | 2-pyridyl |
| H | C$_2$H$_5$ | CH(CH$_3$)(CH$_2$)$_2$ | 3-pyridyl |
| H | CH$_3$ | CH$_2$C(CH$_3$)$_2$ | C$_6$H$_5$ |
| H | CH$_3$ | CH(CH$_3$)(CH$_2$)$_3$ | 4-pyridyl |
| H | CH$_3$ | CH(CH$_3$)(CH$_2$)$_2$ | 4-piperidyl |
| H | C$_2$H$_5$ | CH(C$_2$H$_5$)(CH$_2$)$_2$ | 4-piperidyl |
| H | H | CH(CH$_3$)(CH$_2$)$_2$ | 4-FC$_6$H$_4$ |
| H | CH$_3$ | CH(CH$_3$)(CH$_2$)$_2$ | 4-ClC$_6$H$_4$ |
| H | H | CH$_2$ | C$_6$H$_5$ |
| H | CH$_3$ | CH$_2$ | 4-FC$_6$H$_4$ |
| H | CH$_3$ | — | 4-FC$_6$H$_4$ |
| H | C$_2$H$_5$ | — | 4-ClC$_6$H$_4$ |
| H | H | — | 4-FC$_6$H$_4$ |
| H | CH$_3$ | — | C$_3$H$_5$ |
| H | H | — | C$_3$H$_5$ |
| H | CH$_3$ | — | C$_4$H$_7$ |
| H | C$_2$H$_5$ | — | C$_5$H$_9$ |
| H | CH$_3$ | — | C$_6$H$_{11}$ |
| H | CH$_3$ | — | C$_7$H$_{13}$ |
| H | CH$_3$ | — | 2-(C$_6$H$_5$)C$_3$H$_4$ |
| H | CH$_3$ | — | 1-(C$_6$H$_5$)C$_4$H$_6$ |
| H | CH$_3$ | — | 2-(C$_6$H$_5$)C$_5$H$_8$ |
| H | CH$_3$ | — | 4-(C$_6$H$_5$)C$_6$H$_{10}$ |
| H | C$_2$H$_5$ | — | 3-(C$_6$H$_5$)C$_6$H$_{10}$ |
| H | CH$_3$ | — | 4-pyridyl |
| H | CH$_3$ | — | 4-piperidyl |
| H | CH$_3$ | — | 2-(C$_6$H$_5$)C$_6$H$_{10}$ |
| H | H | — | 4-(C$_6$H$_5$)C$_6$H$_{10}$ |
| H | CH$_3$ | — | 3-(C$_6$H$_5$)C$_7$H$_{12}$ |
| H | CH$_3$ | —CH$_2$— | CH$_3$ |
| H | CH$_3$ | —(CH$_2$)$_3$— | CH$_3$ |
| H | CH$_3$ | —(CH$_2$)$_6$— | CH$_3$ |
| H | CH$_3$ | —(CH$_2$)$_9$— | CH$_3$ |
| H | H | —(CH$_2$)$_6$— | CH$_3$ |
| H | C$_2$H$_5$ | —(CH$_2$)$_3$— | CH$_3$ |
| H | CH$_3$ | —C(CH$_3$)$_2$(CH$_2$)$_5$— | CH$_3$ |
| H | CH$_3$ | —C(CH$_3$)$_2$(CH$_2$)$_5$— | CH$_3$ |
| H | CH$_3$ | —CH(CH$_3$)CH(CH$_3$)(CH$_2$)$_4$ | CH$_3$ |
| CH$_3$ | CH$_3$ | —CH(CH$_3$)(CH$_2$)$_3$ | C$_6$H$_5$ |
| CH$_3$ | CH$_3$ | —(CH$_2$)$_4$— | C$_6$H$_5$ |
| CH$_3$ | CH$_3$ | —C(CH$_3$)$_2$(CH$_2$)$_6$— | H |
| CH$_3$ | CH$_3$ | — | C$_6$H$_5$ |
| CH$_3$ | CH$_3$ | — | 4-ClC$_6$H$_4$ |
| CH$_3$ | CH$_3$ | —CH(CH$_3$)(CH$_2$)$_2$— | 2-pyridyl |
| H | CH$_2$C$_6$H$_5$ | —CH(CH$_3$)(CH$_2$)$_4$— | H |
| H | CH$_2$C$_6$H$_5$ | —C(CH$_3$)$_2$(CH$_2$)$_6$ | H |
| CH$_3$ | CH$_2$C$_6$H$_5$ | — | 4-FC$_6$H$_4$ |
| H | (CH$_2$)$_3$C$_6$H$_5$ | —CH$_2$— | C$_6$H$_5$ |
| H | (CH$_2$)$_4$C$_6$H$_5$ | —(CH$_2$)$_6$— | CH$_3$ |
| C$_2$H$_5$ | C$_2$H$_5$ | —(CH$_2$)$_4$— | C$_6$H$_5$ |
| C$_2$H$_5$ | CH$_3$ | —CH$_2$— | 4-FC$_6$H$_4$ |
| H | i-C$_3$H$_7$ | —CH(CH$_3$)(CH$_2$)$_3$— | 4-piperidyl |
| H | n-C$_4$H$_9$ | —CH(CH$_3$)CH(CH$_3$)(CH$_2$) | H |
| H | n-C$_6$H$_{13}$ | —C(CH$_3$)$_2$(CH$_2$)$_6$ | H |
| CH$_3$ | n-C$_6$H$_{13}$ | —(CH$_2$)$_3$— | CH$_3$ |
| CH$_3$ | CH$_3$ | — | C$_5$H$_9$ |
| CH$_3$ | CH$_3$ | — | 4-(C$_6$H$_5$)C$_6$H$_{10}$ |

PREPARATION U dl-1-Formyl-5-hydroxy-3-hydroxymethylene-2-methyl-7-(2-heptyloxy)-4-oxo-1,2,3,4-tetrahydroquinoline To sodium hydride (18.2 g., 0.38 mole) obtained by washing 50% sodium hydride in mineral oil dispersion with pentane is added dropwise, over a half-hour period, a solution of dl-5-hydroxy-2-methyl-7-(2-heptyloxy)-4-oxo-1,2,3,4-tetrahydroquinoline (11.1 g., 0.038 mole) in ethyl formate (110 g., 1.48 moles). Exothermic reaction occurs with vigorous evolution of hydrogen and formation of a yellow precipitate. The reaction mixture is cooled, ether (750 ml.) added and the resulting mixture then heated at reflux and stirred for 3 hours. It is then cooled to 0° C. and neutralized by addition of 1 N hydrochloric acid (400 ml.). The ether layer is separated and the aqueous phase extracted with ether (2×150 ml.). The ether extracts are combined, washed successively with saturated sodium bicarbonate solution (2×100 ml.) and brine (1×150 ml.) and then dried (MgSO$_4$). Concentration of the dried extract affords an orange foam (10.8 g.). An additional 2.3 g. is obtained by acidifying the sodium bicarbonate wash solutions with concentrated hydrochloric acid followed by extraction of the acid solution with ether (2×100 ml.). Concentration of the combined ethereal extracts after drying gives 2.3 g. of product (Total=13.1 g.). The product is used as is.

$^1$H NMR (60 MHz) (CDCl$_3$) ppm (delta): 12.27 (bs, 1H, ArOH), 8.8–11.9 (m, 1H, variable, =COH), 8.73 (s, 1H, N—CHO), 7.41 (s, 1H, =CH), 6.32 (s, 2H, aromatic), 5.52 (q, 1H, —CH—N), 4.18–4.77 (m, 1H, —O—CH), 0.6–2.08 (m, 17H, CH$_3$—C—C$_5$H$_{11}$ and CH$_3$—C—N).

In like manner, dl-5-hydroxy-2-methyl-7-(5-phenyl-2-pentyloxy)-4-oxo-1,2,3,4-tetrahydroquinoline is converted to dl-1-formyl-5-hydroxy-3-hydroxymethylene-2-methyl-7-(5-phenyl-2-pentyloxy)-4-oxo-1,2,3,4-tetrahydroquinoline.

$^1$H NMR: (60 MHz) (CDCl$_3$) ppm (delta): 12.22 (bs, 1H, ArOH), 8.8–11.6 (variable, 1H, =COH), 8.64 (s, 1H, —CHO), 7.21 (bs, shoulder at 7.30, 6H, aromatic and =CH), 6.23 and 6.17 (two 1H doublets, J=2 Hz, meta), 5.42 (bq, 1H, N—CH), 4.18–4.70 (m, 1H, —OCH), 2.4–3.0 (m, 2H, Ar—CH$_2$), 1.53–2.0 (m, 4H, —(CH$_2$)$_2$—), 1.29 (overlapping doublets, 6H, CH$_3$—C—N and CH$_3$—C—O).

dl-5-hydroxy-7-(2-heptyloxy)-4-oxo-1,2,3,4-tetrahydroquinoline is converted to dl-1-formyl-5-hydroxy-3-hydroxymethylene-7-(2-heptyloxy)-4-oxo-1,2,3,4-tetrahydroquinoline, an oil.

$^1$H NMR (60 MHz) (CDCl$_3$) ppm (delta): 12.1 (bs, 1H, phenolic), 8.8 (s, 1H, —N—CHO), 8.1 (s, 1H), 7.3 (s, 1H), 6.1 (s, 2H, aromatic), 4.5 (bs, 2H, —CH$_2$—), 4.2–4.8 (m, —O—CH$_2$—), 2.0–0.7 (remaining protons).

dl-5-hydroxy-7-(5-pentyl-2-pentyloxy)-4-oxo-1,2,3,4-tetrahydroquinoline is converted to dl-1-formyl-5-hydroxy-3-hydroxymethylene-7-(5-phenyl-2-pentyloxy)-4-oxo-1,2,3,4-tetrahydroquinoline.

$^1$H NMR (60 MHz) (CDCl$_3$) ppm (delta): 12.4 (bs, 1H, phenolic), 8.5 (s, 1H, CHO), 7.2 (m, 6H, aromatic and =CH—), 6.2 (m, 2H, aromatic), 4.5 (s, 2H, —CH$_2$—), 4.4 (m, 1H, —CH—CH$_3$), 2.6 (bt, 2H, —CH$_2$—), 1.7 (m, 5H, remaining protons), 1.3 (d, 3H, —CH—CH$_3$, J=6 Hz). and dl-5-hydroxy-2-methyl-7-(4-phenylbutyloxy)-4-oxo-1,2,3,4-tetrahydroquinoline is converted to dl-1-formyl-5-hydroxy-3-hydroxymethylene-2-methyl-7-(4-phenylbutyloxy)-4-oxo-1,2,3,4-tetrahydroquinoline, m.p. 132°–135° C. (from hexane). Recrystallization from hot methanol provides the analytical sample, m.p. 131°–132° C.

Analysis: Calcd for C$_{22}$H$_{23}$O$_5$N: C, 69.27; H, 6.08; N, 3.67%. Found: C, 69.25; H, 5.88; N, 3.88%.

m/e-381 (m+)

$^1$H NMR (60 MHz) (CDCl$_3$) ppm (delta): 12.4–13.6

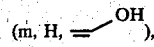

(m, H, =⟨OH⟩), 12.26 (s, 1H, 5—OH), 8.62 (s, 1H, —C(=O)—H), ca. 7.18–7.48

(m, 1H, =⟨H⟩), 7.27 (s, 5H, C$_6$H$_5$), 6.26 (bs, 2H, meta H's), 5.46 (q, 1H, CH—N), 3.82–4.23 (m, 3H, —CH$_2$—O), 2.49–2.80 (m, 3H, ArCH$_2$), 1.67–2.02 (m, 4H —[CH$_2$]$_2$—), 1.27 (d, 3H, CH$_3$).

PREPARATION V dl-1-Formyl-5-hydroxy-2-methyl-7-(5-phenyl-2-pentyloxy)-4-oxo-3-(3-oxobutyl)-1,2,3,4-tetrahydroquinoline To a solution of dl-1-formyl-3-hydroxymethylene-5-hydroxy-2-methyl-7-(5-phenyl-2-pentyloxy)-4-oxo-1,2,3,4-tetrahydroquinoline (229 g., ca. 0.58 mole) in methanol (880 ml.) under a nitrogen atmosphere is added triethylamine (27.2 ml.) with stirring. Methyl vinyl ketone (97.0 ml.) is then added and the mixture stirred overnight at room temperature.

The reaction is complete at this point and comprises a mixture of the title compound and dl-1,3-diformyl-5-hydroxy-2-methyl-7-(5-phenyl-2-pentyloxy)-4-oxo-3-(3-oxobutyl)-1,2,3,4-tetrahydroquinoline. The following steps are required to convert the diformyl compound to the desired title compound.

The reaction mixture is diluted with ether (6 liters) and then washed successively with 10% aqueous sodium carbonate (4×1700 ml.) brine (1×2 liters) and then dried (MgSO$_4$). Concentration of the solution affords 238 g. of a red-brown oil. The oil is dissolved in methanol (1920 ml.) and the solution cooled to 0° C. Potassium carbonate (21.2 g.) is added, the mixture stirred for 3 hours at 0° C. and then treated with acetic acid (18.7 g.). The methanol is removed under reduced pressure and the resultant oil stirred with water (2 liters) and ethyl acetate (2 liters) for 10 minutes. The aqueous phase is separated, extracted with ethyl acetate (1×2 liters) and the combined ethyl acetate solutions washed with water (2×2 liters), brine (1×2 liters) and dried (MgSO$_4$). Concentration under reduced pressure and chromatography of the concentrate on silica gel (1.8 kg.) gives 159 g. of the title product.

m/e-437 (m+)

$^1$H NMR (60 MHz) (CDCl$_3$) ppm (delta): 12.7 (s, 1H, OH), 8.78 (bs, 1H, —CHO), 7.22 (s, 5H, aromatic), 6.22 (bs, 2H, meta H's), 2.12, 2.07 (s, 3H, —CH$_3$—CO—), 1.31 (d, 3H, —CH$_3$—C—O—), and 1.57–5.23 (m, 13H, remaining protons).

Similar treatment of 35 g. (0.09 mole) of dl-1-formyl-5-hydroxy-3-hydroxymethylene-2-methyl-7-(4-phenylbutyloxy)-4-oxo-1,2,3,4-tetrahydroquinoline gives 22.7 g. (60%) of dl-1-formyl-5-hydroxy-2-methyl-7-(4-phenylbutyloxy)-4-oxo-3-(3-oxobutyl)-1,2,3,4-tetrahydroquinoline, m.p. 101°–103° C. The analytical sample is obtained by recrystallization from methanol, m.p. 104°–105° C.

Analysis: Calcd for C$_{25}$H$_{29}$O$_5$N: C, 70.90; H, 6.90; N, 3.31% Found: C, 70.77; H, 6.81; N, 3.46%

$^1$H NMR (60 MHz) (CDCl$_3$) ppm (delta): 12.88 (s, 1H, —OH), 9.08 (bs, 1H, —CHO), 7.29 (s, 5H, C$_6$H$_5$), 6.25 (bs, 2H, meta H's), 4.88–5.43 (m, 1H, —CHN), 3.86–4.21 (m, 2H, —CH$_2$—O—), ca. 2.49–3.02 [m, 7H, ArCH$_2$, —(CH$_2$)$_2$—C(=O)—, —CH—C(=O)], 2.18 [s, 3H, CH$_3$—C(=O)], 1.68–2.03 [m, 4H, —(CH$_2$)$_2$—], 1.13 (d, 3H, CH$_3$).

m/e-423 (m+);

and dl-1-formyl-5-hydroxy-3-hydroxymethylene-7-(5-phenyl-2-pentyloxy)-2-propyl-4-oxo-1,2,3,4-tetrahydroquinoline affords dl-1-formyl-5-hydroxy-7-(5-phenyl-2-pentyloxy)-4-oxo-3-(3-oxobutyl)-1,2,3,4-tetrahydroquinoline which is used as is.

PREPARATION W dl-1-Formyl-5-hydroxy-2-methyl-7-(2-heptyloxy)-4-oxo-3-(3-oxobutyl)-1,2,3,4-tetrahydroquinoline and dl-1,3-Diformyl-5-hydroxy-2-methyl-7-(2-heptyloxy)-4-oxo-3-(3-oxobutyl)-1,2,3,4-tetrahydroquinoline To a solution of dl-5-hydroxy-3-hydroxymethylene-2-methyl-7-(2-heptyloxy)-4-oxo-1,2,3,4-tetrahydroquinoline (13.1 g., 37.7 mmol.), in methanol (56 ml.) and methyl vinyl ketone (5.52 mg., 68 mmol.) is added triethylamine (1.3 ml., 9.3 mmol.). The mixture is stirred for 18 hours under a nitrogen atmosphere at room temperature and is then diluted with ether (550 ml.). The solution is washed with 10% aqueous sodium bicarbonate solution (4×60 ml.), followed by brine (1×100 ml.) and dried (MgSO4). Removal of the ether by evaporation gives a dark oil (16 g.). The oil is dissolved in a minimum volume of benzene and the solution charged to a column of silica gel (500 g.). The column is then eluted with a volume of benzene equal to the volume of the column. The eluting solvent is then changed to 15% ether-benzene and 100 ml. fractions collected when the first color band begins to elute off the column. Fractions 5-13 are combined and concentrated under reduced pressure to give dl-1,3-diformyl-5-hydroxy-2-methyl-7-(2-heptyloxy)-4-oxo-3-(3-oxobutyl)-1,2,3,4-tetrahydroquinoline as a yellow oil (8.7 g.).

The column is eluted further with 15% ether-benzene. Fractions 19-37 are combined and concentrated under reduced pressure to give dl-1-formyl-5-hydroxy-2-methyl-7-(2-heptyloxy)-3-(3-oxobutyl)-1,2,3,4-tetrahydroquinoline as an oil (4.6 g.). Additional monoformyl product is obtained in the following manner:

1 g. of diformyl product is stirred with 200 mg. potassium carbonate in methanol (25 ml.) for two hours at 0° C. The solvent is then evaporated in vacuo and the residue suspended in ether and filtered. The filtrate is concentrated and the residue partitioned between ether and water. The organic layer is separated, the aqueous phase acidified with 10% hydrochloric acid and extracted with ether. The combined ether extracts are washed successively with saturated sodium bicarbonate and brine, and then dried (MgSO4), filtered and concentrated to yield additional monoformyl product.

The monoformyl derivative has the following NMR spectrum:

$^1$NMR (60 MH$_2$) (CDCl$_3$) ppm (delta): 12.73 (s, 1H, ArOH), 8.87 (s, 1H, N—CHO), 6.12 (s, 2H aromatic), 4.78-5.50 (m, 1H, N—CH), 4.11-4.72 (m, 1H, —O—CH), 2.21 (s, 3H, CH$_3$—C(=O)—), 0.63-3.12 (m, 22H, remaining hydrogens).

Similarly, the following compounds are prepared from appropriate reactants:

dl-1-formyl-5-hydroxy-7-(2-heptyloxy)-4-oxo-3-(3-oxobutyl)-1,2,3,4-tetrahydroquinoline, an oil.

$^1$H NMR (60 MH$_2$) (CDCl$_3$) ppm (delta): 12.8 (s, 1H, phenolic), 8.7 (s, 1H, N—CHO), 6.1 (s, 2H, aromatic), 4.1-4.6 (m, 1H, —O—CH), 4.1 (d, 2H, J=5H$_2$, —CH$_2$—), 2.3-3.0 [m, 3H, CH$_2$ and CH-C(=O)], 2.2 [s, 3H, -C(=O)-CH$_3$], 2.3-0.7 (remaining protons).

dl-1-formyl-5-hydroxy-2-methyl-7-(5-phenyl-2-pentyloxy)-4-oxo-3-(3-oxobutyl)-1,2,3,4-tetrahydroquinoline.

$^1$H NMR (60 MH$_2$) (CDCl$_3$) ppm (delta): 12.68 (s, 1H, —OH), 8.82 (b, s, 1H, —C(O)H), 7.20 (b, s, 5H, C$_6$H$_5$), 6.18 (b, s, 2H, aro(m, 1H, —O—CH), 2.17 (s, 3H, —C(O)CH$_3$), 1.30 (d, 3H, —O—C—CH$_3$), 1.12 (d, 3H, —N—C—CH$_3$), 1.4-3.1 (m, 11H, remaining H's).

dl-1-formyl-5-hydroxy-7-(5-phenyl-2-pentyloxy)-4-oxo-3-(3-oxobutyl)-1,2,3,4-tetrahydroquinoline.

m/e-423 (m+)

Also produced as by-product in each of these preparations is the corresponding 1,3-diformyl derivative.

PREPARATION X

Following the procedures of Preparations U and W, the 5-hydroxy-2-R$_4$-7-(Z-W)-4-oxo-1,2,3,4-tetrahydroquinolines of Preparations O, Q and T are converted to compounds having the formula below wherein R$_4$, R$_5$, Z and W are as defined in Preparations O, Q and T. When R$_6$ of the tetrahydroquinoline reactants is hydrogen, it is converted to formyl (CHO).

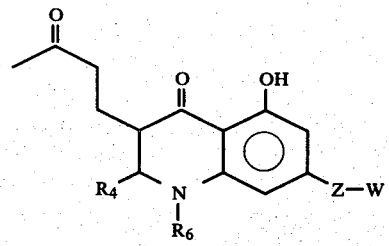

PREPARATION Y dl-5,6,6a,7-Tetrahydro-1-hydroxy-6-beta-methyl-3-(5-phenyl-2-pentyloxy)benzo[c]quinolin-9(8H)-one A solution of dl-1-formyl-5-hydroxy-2-methyl-7-(5-phenyl-2-pentyloxy)-4-oxo-3-(3-oxobutyl)-1,2,3,4-tetrahydroquinoline (174 g., 0.398 mole) in methanolic 2 N KOH (5.9 liters) and methanol (5.9 liters) is stirred and heated at reflux overnight under a nitrogen atmosphere. To the cooled solution is added acetic acid (708 g.) dropwise with stirring over a 15 minute period. The resulting solution is concentrated by rotary evaporation (in vacuo, water aspirator) to a semisolid which is filtered and washed first with water to remove potassium acetate and then with ethyl acetate until all the black tar is removed. Yield=68 g. (44%) yellow solids, m.p. 188°-190° C. Recrystallization from hot ethyl acetate affords the pure product, m.p. 194°-195° C.

m/e-391 (m+)

Analysis: Calcd for C$_{25}$H$_{29}$O$_3$N: C, 76.09; H, 7.47; N, 3.58%. Found: C, 76.43; H, 7.48; N, 3.58%.

$^1$H NMR (60 MHz) $\delta^{TMS}$ (100 mg. dissolved in 0.3 ml. CD$_3$OD and 0.3 ml. CD$_3$S(O)CD$_3$) (ppm): 7.21 (s, 5H, aromatic), 5.80 (s, 2H, meta H's), 1.20 (d, 6H, CH$_3$—CHO and CH$_3$—CH—N).

From the mother liquors, a small amount of the corresponding axial methyl derivative is obtained upon evaporation. It is purified by column chromatography on silica gel using benzene/ether (1:1) as eluant. Evaporation of the eluate and recrystallization of the residue from ether/hexane (1:1) affords analytically pure material, m.p. 225°-228° C.

Its R$_f$ value upon thin layer chromatography on silica gel using 2.5% methanol in ether as eluant and visualization with fast blue is 0.34. The 6-beta methyl derivative exhibits $R_f=0.41$.

m/e-391 (m+)

$^1$H NMR (60 MHz) $\delta^{TMS}$ (100 mg. dissolved in 0.3 ml. CD$_3$OD and 0.3 ml. CD$_3$S(O)CH$_3$) (ppm): 7.19 (s, 5H, aromatic), 5.75 (s, 2H, meta H's), 1.21 (d, 3H, CH$_3$—CHO—), and 0.95 (d, 3H, CH$_3$—CH—N).

Similar treatment of 22 g. of dl-1-formyl-5-hydroxy-2-methyl-7-(4-phenylbutyloxy)-4-oxo-3-(3-oxobutyl)-1,2,3,4-tetrahydroquinolines gives 17.1 g. (87%) of dl-5,6,6a,7-tetrahydro-1-hydroxy-6-beta-methyl-3-(4-phenylbutyloxy)benzo[c]quinolin-9(8H)-one, m.p. 222°–224° C. The analytical sample is obtained by recrystallization from methanol, m.p. 224°–225° C.

Analysis: Calcd for C$_{24}$H$_{27}$O$_3$N: C, 76.36; H, 7.21; N, 3.71%. Found: C, 76.03; H, 7.08; N, 3.68%.

$^1$H NMR (60 MHz) [1:1 mixture of (CD$_3$)$_2$SO and CD$_3$OD]: 1.24 (d, 3H, 6-beta-CH$_3$)

m/e-377 (m+)

Evaporation of the mother liquor gives 2.8 g. (m.p. 185°–195° C.) of product shown by NMR to be a mixture of the 6-beta-methyl derivative (ca. 40%) and dl-5,6,6a,7-tetrahydro-1-hydroxy-6-alpha-methyl-3-(4-phenyl butyloxy)benzo[c]quinoline-9(8H)-one.

$^1$H NMR (60 MHz) [1:1 mixture of (CD$_3$)$_2$SO and CD$_3$OD]: 1.24 (d, 1.2H, 6-beta-CH$_3$) and 0.95 (d, 1.8H, 6-alpha-CH$_3$).

PREPARATION Z dl-5,6,6a,7-Tetrahydro-1-hydroxy-6-beta-methyl-3-(2-heptyloxy)benzo[c]quinolin-9(8H)-one A solution of dl-1-formyl-5-hydroxy-2-methyl-7-(2-heptyloxy)-4-oxo-3-(3-oxobutyl)-1,2,3,4-tetrahydroquinoline (4.5 g., 11.5 mmol.) in methanol (150 ml.) is treated with 2 N methanolic potassium hydroxide solution (150 ml.). The mixture is stirred for one hour at room temperature and then heated at reflux under a nitrogen atmosphere for 20 hours. The dark red mixture is allowed to cool to room temperature, neutralized with acetic acid and concentrated under pressure to about 100 ml. The concentrate is diluted with water (400 ml.) and the brown-red solid separated by filtration, washed with water and dried (6 g.). It is triturated first in ether and then in methanol, filtered and dried (1.96 g.); m.p. 223°–229° C. Recrystallization from hot methanol affords crystals melting at 235°–237° C.

Analysis: Calcd for C$_{21}$H$_{29}$O$_3$N: C, 73.43; H, 8.51; N, 4.08%. Found: C, 73.22; H, 8.30; N, 4.11%.

Additional material is recovered by evaporation of all mother liquors and by chloroform extraction of the aqueous solution from which the brown-red crude product is obtained and subsequent evaporation of the extract. The combined residues are purified by silica gel chromatography using ether as eluant.

In like manner, the following compounds are prepared from appropriate reactants:

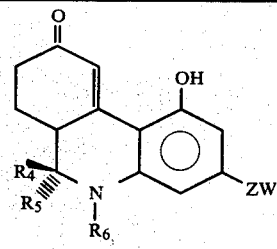

| ZW | R$_4$ | R$_5$ | R$_6$ | m/e (m+) | (°C.) m.p. | Formula | Calc'd C, H, N | Found C, H, N |
|---|---|---|---|---|---|---|---|---|
| —O—CH(CH$_3$)(CH$_2$)$_3$C$_6$H$_5$ | C$_2$H$_5$ | H | H | 405 | 155-6 | C$_{26}$H$_{31}$O$_3$N | C - 77.00<br>H - 7.71<br>N - 3.45 | C - 76.86<br>H - 7.62<br>N - 3.45 |
| —O—CH(CH$_3$)(CH$_2$)$_3$C$_6$H$_5$ | C$_6$H$_{13}$ | H | H | 461 | 139-141 | C$_{30}$H$_{39}$O$_3$N | C - 78.05<br>H - 8.52<br>N - 3.03 | C - 78.16<br>H - 8.53<br>N - 3.09 |
| —O—CH(CH$_3$)(CH$_2$)$_3$C$_6$H$_5$ | C$_5$H$_{11}$ | H | H | 447 | 150-3 | C$_{29}$H$_{37}$O$_3$N | C - 77.81<br>H - 8.33<br>N - 3.13 | C - 77.73<br>H - 8.19<br>N - 3.13 |
| —O—CH(CH$_3$)(CH$_2$)$_3$C$_6$H$_5$ | C$_4$H$_9$ | H | H | 433 | 160-2 | C$_{28}$H$_{35}$O$_3$N | C - 77.56<br>H - 8.14<br>N - 3.23 | C - 77.28<br>H - 7.92<br>N - 3.18 |
| —O—CH(CH$_3$)(CH$_2$)$_3$C$_6$H$_5$ | H | C$_4$H$_9$ | H | 433 | 95-98 | C$_{28}$H$_{35}$O$_3$N | C - 77.56<br>H - 8.14<br>N - 3.23 | C - 77.86<br>H - 8.37<br>N - 3.17 |
| —O—CH(CH$_3$)(CH$_2$)$_3$C$_6$H$_5$ | —(CH$_2$)$_2$—C$_6$H$_5$ | H | H | 481 | 200-201 | C$_{32}$H$_{35}$O$_3$N | C - 79.80<br>H - 7.33<br>N - 2.91 | C - 79.64<br>H - 7.34<br>N - 2.93 |
| —O(CH$_2$)$_3$C$_6$H$_5$ | CH$_3$ | H | H | 363 | 246-7 | C$_{23}$H$_{25}$O$_3$N | C - 76.00<br>H - 6.93<br>N - 3.85 | C - 76.19<br>H - 7.14<br>N - 3.89 |
| —C(CH$_3$)$_2$—C$_6$H$_5$ | CH$_3$ | H | H | 355 | 261-2 | C$_{23}$H$_{33}$O$_2$N | C - 77.70<br>H - 9.36<br>N - 3.94 | C - 77.94<br>H - 9.21<br>N - 3.99 |
| —O(CH$_2$)$_2$C$_6$H$_5$ | CH$_3$ | H | H | 349 | 248-250 | C$_{22}$H$_{23}$O$_3$N | C - 75.62<br>H - 6.63<br>N - 4.01 | C - 75.26<br>H - 6.66<br>N - 3.93 |
| —OCH(CH$_3$)(CH$_2$)$_3$C$_6$H$_5$ | H | H | H | 377 | 170-173 | C$_{24}$H$_{27}$O$_3$N | C - 76.36<br>H - 7.21<br>N - 3.71 | C - 76.38<br>H - 7.21<br>N - 3.85 |
| —O—CH(CH$_3$)(CH$_2$)$_4$CH$_3$ | H | H | H | 329 | 208-209 | C$_{20}$H$_{27}$O$_3$N | C - 72.92 | C - 72.92 |

-continued

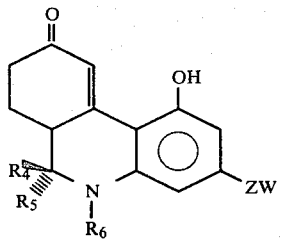

| ZW | R4 | R5 | R6 | m/e (m+) | (°C.) m.p. | Formula | Calc'd C, H, N | Found C, H, N |
|---|---|---|---|---|---|---|---|---|
| —O—CH(CH₃)(CH₂)₃C₆H₅ | n-C₃H₇ | H | H | — | 164–166 | C₂₇H₃₃O₃N | H - 8.26<br>N - 4.25<br>C - 77.29<br>H - 7.93<br>N - 3.34 | H - 8.31<br>N - 4.42<br>C - 76.97<br>H - 7.98<br>N - 3.41 |
| —O—CH(CH₃)(CH₂)₃C₆H₅(a) | CH₃ | H | H | 391 | 176–178 | C₂₅H₂₉O₃N | C - 76.69<br>H - 7.47<br>N - 3.58 | C - 76.32<br>H - 7.36<br>N - 3.33 |
| —O—CH(CH₃)(CH₂)₃C₆H₅(b) | CH₃ | H | H | 391 | 172–174 | C₂₅H₂₉O₃N | C - 76.69<br>H - 7.47<br>N - 3.58 | C - 76.40<br>H - 7.39<br>N - 3.51 |

(a) l-enantiomer; [alpha]$_D^{25}$ = −416.0° (C = 0.33, CH₃OH)
(b) d-enantiomer; [alpha]$_D^{25}$ = +412.9° (C = 1.0, CH₃OH)

PREPARATION AA

The compounds of Preparation X are reacted according to the procedure of Preparation Z to produce compounds having the formula shown below wherein R₄, R₅, R₆, Z and W are as defined in Preparation X.

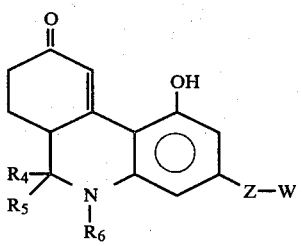

PREPARATION BB dl-5,6,6a,7,10,10a-Hexahydro-1-hydroxy-6-beta-methyl-3-(2-heptyloxy)benzo[c]quinolin-9(8H)-one A suspension of dl-5,6,6a,7-tetrahydro-1-hydroxy-6-beta-methyl-3-(2-heptyloxy)benzo[c]quinolin-9(8H)-one (1.0 g., 2.91 mmole) in tetrahydrofuran (20 ml.) is added dropwise via an addition funnel to a rapidly stirred solution of lithium (0.1 g.) in liquid ammonia (75 ml., distilled through potassium hydroxide pellets). The addition funnel is rinsed with tetrahydrofuran (10 ml.). The mixture is stirred for 10 minutes and then solid ammonium chloride is added to discharge the blue color. The excess ammonia is allowed to evaporate and the residue taken up in water (100 ml.) and ethyl acetate (50 ml.). The ethyl acetate layer is separated and the aqueous phase extracted with ethyl acetate (2×50 ml.). The combined extracts are washed with brine, dried (MgSO₄) and concentrated under reduced pressure to a brown semi-solid product (1.35 g.). Trituration of the semi-solid in pentane/ether (1:1) gives a light brown solid (0.884 g.); m.p. 130°–138° C.

The above procedure is repeated but using 1.84 g. (5.36 mmole) of the benzo[c]quinolin-9-one reactant, 0.184 g. of lithium, 140 ml. of liquid ammonia and 45 ml. of tetrahydrofuran. The residue (2.1 g.) remaining after evaporation of the ammonia is dissolved in benzene and charged to a chromatography column (3.8×61 cm) containing silica gel (250 g.). The column is eluted with a volume of degassed benzene equal to the volume of the column and then with 1700 ml. of degassed benzene-ether (9:1). Continued elution (1100 ml.) gives a brilliant red eluate which is concentrated to a light purple solid (580 mg.) under reduced pressure and triturated in benzene-ether (1:1) to give 370 mg. of solid; m.p. 154°–156° C. It is stored under nitrogen and in the dark. The isolated solids are mixtures of the cis- and trans-forms of the title product.

m/e-345 (m+)

¹H NMR (100 MHz) (CDCl₃) ppm (delta); 6.85 and 7.49 (1H, broad variable, OH), 5.67, 5.71, 5.85, 5.93 (d, J=2 Hz, 2H total, aromatic hydrogens for cis/trans mixture), 0.90 (t, 3H, terminal CH₃), 1.12–4.43 (m, remaining H).

PREPARATION CC

Following the procedure of Preparation BB, the compounds of Preparation Z and AA are converted to products having the formula

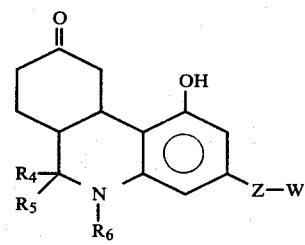

wherein R₄, R₅, R₆, and W are as defined in Preparations Z and AA. Both cis- and trans-forms are produced.

PREPARATION DD

Isomeric
5,6,6a,7,10,10a-Hexahydro-1-acetoxy-6-beta-methyl-3-(2-heptyloxy)benzo[c]quinolin-9(8H)-ones Pyridine (2.2 ml.) is added to a suspension of 5,6,6a,7,10,10a-hexahydro-1-hydroxy-6-beta-methyl-3-(2-heptyloxy)benzo[c]quinolin-9(8H)-one (222 mg., 0.642 mmole) in acetic anhydride (2.2 ml.) under a nitrogen atmosphere. The mixture is stirred for 1.5 hours at room temperature and is then poured onto ice (50 ml.). The gum which separates is extracted with ether (3×50 ml.) and the combined extracts washed first with water (4×50 ml.) and then with brine (1×60 ml.). The extract is dried (MgSO4) and evaporated under reduced pressure to a red oil (250 mg.).

The oil is dissolved in a minimum of hot ether and charged to a silica gel (45 g.) column, packed and eluted with pentane-ether (3:1). The column is eluted with pentane-ether (3:1, 200 ml.). Elution is continued and fractions (10 ml.) collected. Fractions 22–32 are combined and concentrated to a foam (113.5 mg.) which is crystallized from petroleum ether as white crystals; m.p. 112°–114° C.

Fractions 33–50 are combined and concentrated to a foam (89.7 mg.) which is recrystallized from petroleum ether as white crystals; m.p. 78°–82° C.

The products are the isomeric mono-acetylated compounds.

By means of this procedure the products of Preparation CC are converted to their isomeric 1-acetoxy derivatives. Compounds having the formula below are thus prepared.

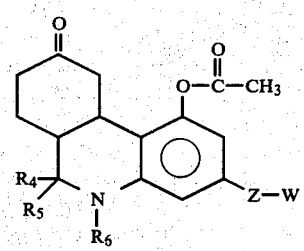

wherein $R_4$, $R_5$, $R_6$, Z and W are as defined in Preparation CC.

Substitution of acetic anhydride by benzoic anhydride, propionic anhydride, butyric anhydride or valeric anhydride in this procedure affords the corresponding isomeric 1-benzoyloxy, 1-propionyloxy, 1-butyryloxy and 1-valeryloxy derivatives.

PREPARATION EE dl-trans-5,6,6a-beta,7,10,10a-alpha-hexahydro-1-acetoxy-5-acetyl-6-beta-methyl-3-(5-phenyl-2-pentyloxy)benzo[c]quinoline-9(8H)-one 3.49 g. (0.008 mole) of dl-trans-5,6,6a-beta,7,10,10a-alpha-hexahydro-1-acetoxy-6-beta-methyl-3-(5-phenyl-2-pentyloxy)benzo[c]quinolin-9(8H)-one is dissolved in 20 ml. (alcohol-free) chloroform, the solution is cooled in an ice-water bath then added 14 ml. pyridine (dried over potassium hydroxide pellets) followed by 0.95 ml. (0.013 mole) of acetyl chloride which is dissolved in 5 ml. chloroform. The homogeneous solution is then stirred at ambient temperature for 18 hours. The reaction mixture is poured onto 50 ml. ice-water and extracted twice with chloroform (25 ml. each). The combined organic layers are washed with 25 ml. sat. sodium bicarbonate, 25 ml. water, 25 ml. brine, dried over magnesium sulfate, filtered and evaporated to dryness under reduced pressure. Purification is achieved via chromatography (200 g. Brinkman silica gel, solvent: cyclohexane 3, ether 1) to afford 2.20 g. (83.8% yield) of the above title compound.

Analysis: Calcd for $C_{29}H_{35}O_5N$: C, 72.90; H, 7.39; N, 2.80%. Found: C, 72.69; H, 7.48; N, 2.49%.

I.R. (KBr): 2.90μ (m), 3.38μ (s), 3.48μ (s), 5.62μ (s), 5.78μ (s), 6.00μ (s), 6.15μ (s), 6.30μ (s).

m/e-477 (m+)

$^1$HNMR (60 MHz) $\delta_{CDCl_3}{}^{TMS}$: 7.20 (m, 5H, arom.), 6.53 (d, 1H, $C_{-2}$), 6.39 (d, 1H, $C_{-4}$), 4.71–4.08 (m, 2H, methines), 2.29 (s, 3H, acetate Me), 2.02 & 2.04 (2s, 3H, amide Me), 1.25 & 1.23 (2d, 3H, $C_{-6}$Me), 1.12 (d, 3H, side chain Me), 3.20–1.36 (variable remaining protons).

In like manner, dl-cis-5,6,6a-beta,7,10,10a-beta-hexahydro-1-acetoxy-6-beta-methyl-3-(5-phenyl-2-pentyloxy)benzo[c]quinolin-9(8H)-one is converted to dl-cis-5,6,6a-beta,7,10,10a-beta-hexahydro-1-acetoxy-5-acetyl-6-beta-methyl-3-(5-phenyl-2-pentyloxy)benzo[c]quinolin-9(8H)-one.

m.p. 125°–128° C., yield 82%.

Analysis: Calcd for $C_{29}H_{35}O_5N$: C, 72.90; H, 7.39; N, 2.80%. Found: C, 72.80; H, 7.35; N, 2.70%.

$^1$HNMR (60 MHz) $\delta_{CDCl_3}{}^{TMS}$: 7.22 (m, 5H, arom.), 6.55 (2d, 2H, $C_2$ & $C_4$), 5.02–4.62 (m, 1H, $C_{-6}$methine), 4.52–2.11 (m, 1H, side chain methine), 2.28 (s, 3H, acetate Me), 2.11 & 2.13 (3H, amide Me), 1.26 & 1.28 (3H, $C_{-6}$Me), 1.22 (d, 3H, side chain Me), 3.42–1.65 (variable remaining protons).

I.R. (KBr): 2.95μ (w), 3.43μ (s), 5.65μ (s), 5.81μ (s), 6.02μ (s), 6.16μ (s), 6.32μ (s), 6.70μ (s).

m/e-477 (m+)

PREPARATION FF dl-5,6,6a-beta,7,10,10a-alpha-Hexahydro-1-acetoxy-6-beta-methyl-3-(2-heptyloxy)benzo[c]quinolin-9(8H)-one The procedure of Preparation BB is repeated but using double the quantities of reactants. The product (2.22 g.) is then directly acetylated according to the procedure of Preparation DD to give 2.35 g. of acetylated product. The product is triturated in pentane-ether (3:1) to a tan solid (905 mg.) which when recrystallized from ethanol gives 404 mg. of light tan crystals; m.p. 112°–113.5° C.

The mother liquors from which each of the above solids is separated, combined and concentrated. The residue is dissolved in a minimum of benzene-ether-methylene chloride (1:1:1) and charged to a silica gel (275 g.) column (packed and eluted with petroleum ether-ether [3:1]). The column is eluted first with 2 liters of petroleum ether-ether (3:1) followed by 1.5 liters of petroleum ether-ether (2:1) and 2 liters of petroleum ether-ether (1:1). Fractions 2–11 (50 ml. each) of eluate from the 1:1 solvent system are collected and concentrated under reduced pressure to a foam (496 mg.). Crystallization from petroleum ether affords white crystals; m.p. 100°–113° C. (410 mg.). Recrystallization from ethanol-water (1:1) gives dl-trans-5,6,6a-beta,7,10,10a-alpha-hexahydrol-1-acetoxy-6-beta-methyl-3-(2-heptyloxy)benzo[c]quinolin-9(8H)-one melting at 111°–112° C.

m/e-387 (m+)

Analysis: Calcd for $C_{23}H_{33}O_4N$: C, 71.29; H, 8.58; N, 3.61%. Found: C, 70.95; H, 8.64; N, 3.58%.

Fractions 12–18 and 19–27 (50 ml. each) are collected and concentrated to afford 273 mg. and 208 mg., respectively, of acetylated product. Crystallization of the residue from fractions 19–27 from petroleum ether gives white crystals (119 mg.); m.p. 84°–88° C. Recrystallization from ethyl acetate-hexane (1:10) gives dl-cis-5,6,6a-beta,7,10,10a-beta-hexahydro-1-acetoxy-3-(2-heptyloxy)-6-beta-methyl-benzo[c]quinolin-9(8H)-one, m.p. 84°–86° C.

Analysis: Calcd for $C_{23}H_{33}O_4N$: C, 71.29; H, 8.58; N, 3.61%. Found C, 71.05; H, 8.48; N, 3.56%.

Similarly, the following compounds are prepared from appropriate reactants:

dl-trans-5,6,6,a-beta,7,10,10a-alpha-hexahydro-1-acetoxy-6-beta-methyl-3-(5-phenyl-2-pentyloxy)benzo[c]quinolin-9(8H)-one, m.p. 80°–82° C.
m/e-435 (m+)

Analysis: Calcd for $C_{27}H_{33}O_4N$: C, 74.45; H, 7.64; N, 3.22%. Found: C, 74.43; H, 7.73; N, 3.28%.

dl-cis-5,6,6a-beta,7,10,10a-beta-hexahydro-1-acetoxy-6-beta-methyl-3-(5-phenyl-2-pentyloxy)benzo[c]quinolin-9(8H)-one, m.p. 172°–176° C. as the hydrochloride salt from acetone-ether (1:1).

Analysis: Calcd for $C_{27}H_{33}O_4N \cdot HCl$: C, 68.71; H, 7.26; N, 2.97%. Found: C, 68.86; H, 7.16; N, 2.97%.

dl-trans-5,6,6a-beta,7,10,10a-alpha-hexahydro-1-acetoxy-3-(5-phenyl-2-pentyloxy)-6-beta-propylbenzoic[c]quinolin-9-(8H)-one; m.p. 79°–80° C.
m/e-463 (m+)

dl-cis-5,6,6a-beta,7,10,10a-beta-hexahydro-1-acetoxy-3-(5-phenyl-2-pentyloxy)-6-beta-propylbenzo[c]quinolin-9(8H)-one; m.p. 144°–146° C., as the HCl salt.
m/e-463 (m+)

d-cis-5,6,6a-beta,7,10,10a-beta-hexahydro-1-acetoxy-3-(5-phenyl-2-pentyloxy)-6-beta-methylbenzo[c]quinolin-9(8H)-one; m.p. 90°–94° C. (dec.) as the hydrochloride salt.
$[alpha]_D^{25} = +22.8°$ (c=0.31, $CH_3OH$)
m/e-435 (m+)

Analysis: Calcd for $C_{27}H_{33}O_4N \cdot HCl$: C, 68.71; H, 7.26; N, 2.97%. Found: C, 69.24; H, 7.30; N, 3.01%.

d-trans-5,6,6a-beta,7,10,10a-beta-hexahydro-1-acetoxy-3-(5-phenyl-2-pentyloxy)-6-beta-methylbenzo[c]quinolin-9(8H)-one; m.p. 90°–95° C. (dec.) as the hydrochloride salt.
$[alpha]_D^{25} = +78.46°$ (c=0.13, $CH_3OH$).
m/e-435 (m+)

Analysis: Calcd for $C_{27}H_{33}O_4N \cdot HCl$: C, 68.71; H, 7.26; N, 2.97%. Found: C, 70.20; H, 7.23; N, 3.07%.

l-cis-5,6,6a-beta,7,10,10a-beta-hexahydro-1-acetoxy-3-(5-phenyl-2-pentyloxy)-6-beta-methylbenzo[c]quinolin-9(8H)-one; m.p. 90°–92° C. as the hydrochloride.
$[alpha]_D^{25} = -20.5°$ (c=0.19, $CH_3OH$)
m/e-435 (m+)

Analysis: Calcd for $C_{27}H_{33}O_4N \cdot HCl$: C, 68.71; H, 7.26; N. 2.97%. Found: C, 68.92; H, 7.23; N, 3.09%.

l-trans-5,6,6a-beta,7,10,10a-beta-hexahydro-1-acetoxy-3-(5-phenyl-2-pentyloxy)-6-beta-methyl-benoz[c]quinolin-9(8H)-one; m.p. 92°–96° C. as the hydrochloride.
$[alpha]_D^{25} = -79.0°$ (c=0.10, $CH_3OH$)
m/e-435 (m+)

Analysis: Calcd for $C_{27}H_{33}O_4N \cdot HCl$: C, 68.71; H, 7.26; N, 2.97%. Found: C, 68.67; H, 7.23; N, 3.02%.

PREPARATION GG dl-5,6,6a-beta-7,10,10a-hexahydro-1-acetoxy-3-(2-heptyloxy)-benzo[c]quinolin-9(8H)-one A solution of dl-5,6,6a,7-tetrahydro-1-hydroxy-3-(2-heptyloxy)benzo[c]quinolin-9(8H)-one (9.0 g.) in tetrahydrofuran (100 ml.) is added dropwise to a rapidly stirred solution of lithium (0.1 g.) in liquid ammonia (750 ml.). An additional 0.1 g. of lithium is added portionwise during the addition to insure a blue color. The mixture is stirred for 10 minutes and then the blue color discharged by addition of excess ammonium chloride. The excess ammonia is allowed to evaporate and the residue is taken up in a mixture of water and ethyl acetate. The organic layer is separated and the aqueous phase extracted twice more with ethyl acetate. The combined extracts are washed with water, brine, dried ($MgSO_4$) and evaporated to give 8.45 g. of crude product as a brown solid.

The crude product (8.0 g.) is suspended in methylene chloride (48 ml.) at 0° C. and treated with N,N-dimethyl-4-aminopyridine (3.24 g.) and triethylamine (3.72 ml.). Acetic anhydride (2.52 ml.) is then added to the mixture which is then stirred for 30 minutes at 0° C. It is diluted with methylene chloride (300 ml.) and the methylene chloride layer separated, washed with water (3×150 ml.), saturated sodium bicarbonate (1×100 ml.), brine (1×100 ml.), and dried ($MgSO_4$). Evaporation of the methylene chloride gives 13.7 g. of dark oil which is chromatographed on a silica gel (450 g.) column. The column is eluted sequentially with ether-hexane (1:1), ether-hexane (2:1) and ether. Fractions of 18 ml. each are collected. Fractions 176–224 are combined and concentrated to an oil which is crystallized from hexane to give 3.24 g. (32%) yield of the trans-isomer of the title compound as light yellow crystals; m.p. 65.5°–68° C.
m/e-373 (m+)

IR (KBr): 5.82 (ketone C=O), 5.75 (ester C=O), 295 (NH) $\mu$.

Fractions 246–290 are combined and concentrated to give 0.55 g. (5%) of crude cis-isomer of the title compound as an oil. It is purified further by column chromatography as described above to give the pure cis-isomer as an oil.
m/e-373 (m+).

IR ($CHCl_3$): 5.82 (ketone C=O), 5.67 (ester C=O), 2.92 (NH) $\mu$.

Analysis: Calcd for $C_{22}H_{31}O_4N$: C, 70.75; H, 8.37; N, 3.75%. Found: C, 70.90; H, 8.54; N, 3.79%.

Fractions 225–245 are combined and evaporated to give 2.69 g. (26%) of a mixture of cis- and trans-isomers which are separated by the procedure described above.

The following compounds are similarly prepared from dl-5,6,6a,7-tetrahydro-1-hydroxy-3-(5-phenyl-2-pentyloxy)benzo[c]quinolin-9(8H)-one:

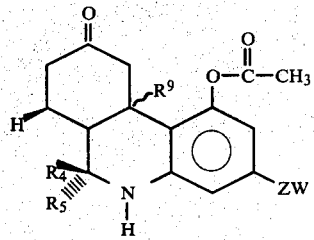

| ZW | R4 | R5 | R9 | m/e (m+) | (°C.) m.p. | Formula | Calc'd C, H, N | Found C, H, N |
|---|---|---|---|---|---|---|---|---|
| —O—CH(CH3)(CH2)3C6H5 | C2H5 | H | ◀H | 449 | 125–130 | C28H35O4N HCl | C-69.18 H-7.47 N-2.88 | C-68.89 H-7.45 N-2.90 |
| —O—CH(CH3)(CH2)3C6H5 | C2H5 | H | ⫼H | 449 | 153–155 | C28H35O4N HCl | C-69.18 H-7.47 N-2.88 | C-69.18 H-7.32 N-2.93 |
| —O—CH(CH3)(CH2)3C6H5 | C6H13 | H | ⫼H | 505 | 103–104 | C32H43O4N | C-76.00 H-8.57 N-2.77 | C-75.88 H-8.47 N-2.84 |
| —O—CH(CH3)(CH2)3C6H5 | C6H13 | H | ◀H | 505 | 100–101 | C32H43O4N | C-76.00 H-8.57 N-2.77 | C-75.62 H-8.39 N-2.63 |
| —O—CH(CH3)(CH2)3C6H5 | CH2CH2 C6H5 | H | ⫼H | 525 | 100–105 | C34H39O4N | C-77.68 H-7.48 N-2.66 | C-77.54 H-7.40 N-2.65 |
| —O—CH(CH3)(CH2)3C6H5 | CH2CH2 C6H5 | H | ◀H | 525 | 118–119 | C34H39O4N | C-77.68 H-7.48 N-2.66 | C-77.62 H-7.61 N-2.64 |
| —O—CH(CH3)(CH2)3C6H5 | C5H11 | H | ⫼H | 491 | 99–100 | C31H41O4N | C-75.73 H-8.41 N-2.85 | C-75.82 H-8.31 N-3.12 |
| —O—CH(CH3)(CH2)3C6H5 | C5H11 | H | ◀H | 491 | 129–130 | C31H41O4N | C-75.73 H-8.41 N-2.85 | C-75.68 H-8.26 N-2.95 |
| —O—CH(CH3)(CH2)3C6H5 | C4H9 | H | ⫼H | 477 | 86–88 | C30H39O4N | C-75.44 H-8.23 N-2.93 | C-75.50 H-8.12 N-2.91 |
| —O—CH(CH3)(CH2)3C6H5 | C4H9 | H | ◀H | 477 | 104–106 | C30H39O4N | C-75.44 H-8.23 N-2.93 | C-75.76 H-8.26 N-3.02 |
| —O(CH2)3C6H5 | CH3 | H | ◀H | 407 | 132–134 | C25H29O4N | C-73.68 H-7.17 N-3.44 | C-73.93 H-7.05 N-3.41 |
| —O—(CH2)3C6H5 | CH3 | H | ⫼H | 407 | 110–112 | C25H29O4N | C-73.68 H-7.17 N-3.44 | C-73.45 H-7.23 N-3.39 |
| —O—CH(CH3)(CH2)3C6H5 | H | H | ◀H | 421 | oil | C26H31O4N | C-74.08 H-7.41 N-3.32 | C-74.16 H-7.59 N-3.20 |
| —O—CH(CH3)(CH2)3C6H5 | H | H | ⫼H | 421 | oil | C26H31O4N | C-74.08 H-7.41 N-3.32 | C-74.04 H-7.49 N-3.54 |
| —O—CH(CH3)(CH2)3C6H5 | H | CH3 | ◀H | 435 | 107–110(a) | C27H33O4N HCl | C-68.71 H-7.26 N-2.96 | C-68.92 H-7.17 N-2.86 |
| —O—CH(CH3)(CH2)3C6H5 | H | CH3 | ⫼H | 435 | 94–102(b) | C27H33O4N HCl | C-68.71 H-7.26 N-2.96 | C-68.71 H-7.26 N-3.12 |

(a) and (b): Transformed to hydrochloride salts by general procedure of salt formation. On thin-layer chromatography in benzene/ether (1:1) $R_f$ of (a) = 0.74 and $R_f$ of (b) = 0.72.

PREPARATION HH dl-5,6,6a,7-Tetrahydro-1-acetoxy-6-beta-methyl-3-(5-phenyl-2-pentyloxy)benzo[c]quinolin-9(8H)-one To a stirred solution of dl-5,6,6a,7-tetrahydro-1-hydroxy-6-beta-methyl-3-(5-phenyl-2-pentyloxy)benzo[c]quinolin-9(8H)-one (4.5 g., 0.0115 mole) in pyridine (45 ml.) at room temperature is added acetic anhydride (45 ml.). The resulting solution is stirred for 3.5 hours and is then poured onto ice-water (250 ml.) and the mixture extracted with diisopropyl ether (2×250 ml.). The combined extracts are washed with water (3×200 ml.), dried (MgSO4) and evaporated under reduced pressure to a yellow-brown oil which solidifies on scratching the walls of the flask containing it. Trituration of the solid with n-heptane gives 2.0 g. of the 1-acetoxy derivative (40% yield). It is purified by recrystallization from hot chloroform-n-hexane (1:4) to give the pure ester: m.p. 136°–140° C.

m/e-433 (m+)

1H NMR (60 MHz) (CDCl3) ppm (delta): 7.21 (bs, 5H, aromatic), 6.62 (d, J=1.5 Hz, 1H, C=C—H), 5.97 (d, J=3 Hz, 1H, meta H), 5.86 (d, J=3 Hz, 1H, meta H), 2.27 [s, 3H, CH3—C(=O)], 1.21 (d, J=7 Hz, 6H, CH3—C—N, CH3—C—O), 1.49–4.51 (m, 14H, remaining protons).

The following tetrahydro-1-acetoxy-3-(ZW-substituted)-benzo[c]quinolin-9(8H)-ones are similarly prepared from appropriate reactants according to the above procedures.

converted to their corresponding benzoyl, acetyl, propionyl, butyryl, valeryl, 2-phenylacetyl and 4-phenylbutyryl derivatives by reaction with the appropriate acyl chloride. The compounds are tetrahydro- or hexahydro-benzo[c]quinolines of the formula

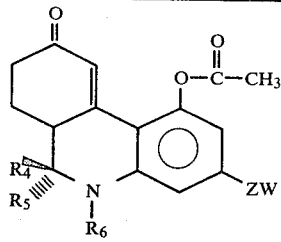

| ZW | R4 | R5 | R6 | m/e (m+) | (°C.) m.p. | Formula | Calc'd C, H, N | | Found C, H, N | |
|---|---|---|---|---|---|---|---|---|---|---|
| —C(CH3)2C6H13 | CH3 | H | H | 397 | 108–112 | C25H35NO3 | C | 75.53 | C | 75.62 |
| | | | | | | | H | 8.87 | H | 8.73 |
| | | | | | | | N | 3.52 | N | 3.52 |
| —OCH(CH3)(CH2)3C6H5 [6R,6aR] | H | CH3 | H | 433 | 125–130 | C27H31O4N | C | 74.80 | C | 74.96 |
| | | | | | | | H | 7.21 | H | 7.11 |
| | | | | | | | N | 3.23 | N | 3.19 |
| —OCH(CH3)(CH2)3C6H5 [6S,6aR] | CH3 | H | H | 433 | 145–146 | C27H31O4N | C | 74.80 | C | 74.91 |
| | | | | | | | H | 7.21 | H | 7.20 |
| | | | | | | | N | 3.23 | N | 3.24 |
| —OCH(CH3)(CH2)3C6H5 [2'S,6S,6aR] | CH3 | H | H | 433 | 167–168 | C27H31O4N | C | 74.80 | C | 74.66 |
| | | | | | | | H | 7.21 | H | 7.20 |
| | | | | | | | N | 3.23 | N | 3.33 |
| —OCH(CH3)(CH2)3C6H5 [2'R,6S,6aR] | CH3 | H | H | 433 | 120–121 | C27H31O4N | C | 74.80 | C | 74.58 |
| | | | | | | | H | 7.21 | H | 7.19 |
| | | | | | | | N | 3.23 | N | 3.27 |
| —OCH2CH2C6H5 | CH3 | H | H | 391 | 159–160 | C24H25O4N | C | 73.63 | C | 73.38 |
| | | | | | | | H | 6.44 | H | 6.41 |
| | | | | | | | N | 3.58 | N | 3.59 |

PREPARATION II dl-trans-5,6,6a-beta,7,10,10a-alphahexahydro-1-acetoxy-3-(2-heptyloxy)-5-benzoyl-6-beta-methylbenzo[c]quinolin-9(8H)-one To a stirred solution of the product of Preparation FF, dl-trans-5,6,6a-beta,7,10,10a-alpha-hexahydro-1-acetoxy-6-beta-methyl-3-(2-heptyloxy)-benzo[c]quinolin-9(8H)-one (812 mg.) in 2.5 ml. pyridine is added 421 mg. benzoyl chloride in 5 ml. chloroform. After two hours, the reaction mixture is poured onto ice and extracted twice with ether. The combined ether extracts are washed with water, sodium bicarbonate, dried (MgSO4) and filtered to yield, after concentration and crystallization from ether/petroleum ether, dl-trans-5,6,6a-beta,7,10,10a-alpha-hexahydro-1-acetoxy-3-(2-heptyloxy)-5-benzoyl-6-beta-methylbenzo[c]quinolin-9(8H)-one, m.p. 108°–110° C.

m/e-491 (m+)

Repetition of this procedure but using an equivalent amount of acetyl chloride in place of benzoyl chloride and the appropriate benzo[c]quinoline affords the following compound:

dl-trans-5,6,6a-beta,7,10,10a-alpha-hexahydro-1-acetoxy-3-(2-heptyloxy)-5-acetyl-6-beta-methylbenzo[c]quinolin-9(8H)-one.

m/e-433 (m+)

In like manner, the remaining compounds of Preparation FF and those of Preparations DD and HH are

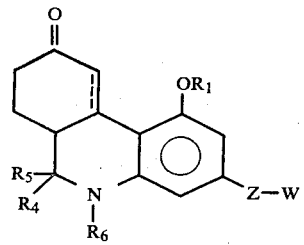

wherein the broken line is a bond or no bond; R4, R5, Z, W and R1 are as defined in Preparations DD, FF and HH and R6 is benzoyl, acetyl, propionyl, butyryl, valeryl, 2-phenylacetyl or 4-phenylvaleryl.

I claim:
1. A compound of the formula

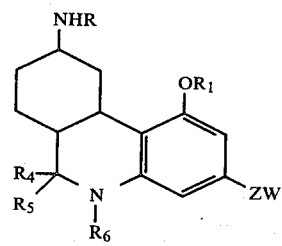

or a pharmaceutically acceptable acid addition salt thereof wherein R is hydrogen, COR7 or SO2R8 where R7 is a member selected from the group consisting of hydrogen, alkyl, having from one to five carbon atoms; alkenyl and alkynyl each having from two to six carbon atoms, trifluoromethyl, benzyl, furyl, thienyl, pyridyl and R$_9$C$_6$H$_4$ where R$_9$ is a member selected from the group cosisting of H, NH$_2$, F, Cl, Br, CH$_3$ and OCH$_3$; R$_8$ is alkyl having from one to five carbon atoms or R$_9$C$_6$H$_4$;

R$_1$ is selected from the group consisting of hydrogen, benzyl, benzoyl, alkanoyl having from one to five carbon atoms and —CO—(CH$_2$)$_p$—NR$_2$R$_3$ wherein p is 0 or an integer from 1 to 4; each of R$_2$ and R$_3$ when taken individually is selected from the group consisting of hydrogen and alkyl having from one to four carbon atoms; R$_2$ and R$_3$ when taken together with the nitrogen to which they are attached form a 5- or 6-membered heterocyclic ring selected from the group consisting of piperidino, pyrrolo, pyrrolidino, morpholino and N-alkylpiperazino having from one to four carbon atoms in the alkyl group;

R$_4$ is selected from the group consisting of hydrogen, alkyl having from 1 to 6 carbon atoms and —(CH$_2$)$_z$—C$_6$H$_5$ wherein z is an integer from 1 to 4;

R$_5$ is selected from the group consisting of hydrogen, methyl and ethyl;

R$_6$ is selected from the group consisting of hydrogen, —(CH$_2$)$_y$—carbalkoxy having from one to four carbon atoms in the alkoxy group and wherein y is 0 or an integer from 1 to 4, carbobenzyloxy, formyl, alkanoyl having from two to five carbon atoms, alkyl having from one to six carbon atoms, —(CH$_2$)$_x$—C$_6$H$_5$ wherein x is an integer from 1 to 4; and —CO(CH$_2$)$_{x-1}$—C$_6$H$_5$;

Z is selected from the group consisting of
(a) alkylene having from one to nine carbon atoms;
(b) —(alk$_1$)$_m$—X—(alk$_2$)$_n$— wherein each of (alk$_1$) and (alk$_2$) is alkylene having from one to nine carbon atoms, with the proviso that the summation of carbon atoms in (alk$_1$) plus (alk$_2$) is not greater than nine; each of m and n is 0 or 1; X is selected from the group consisting of O, S, SO and SO$_2$; and W is selected from the group consisting of hydrogen, methyl, pyridyl, piperidyl,

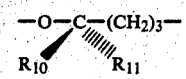

wherein W$_1$ is selected from the group consisting of hydrogen, fluoro and chloro; and

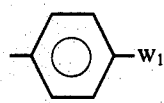

whrerein W$_2$ is selected from the group consisting of hydrogen and

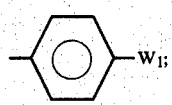

a is an integer from 1 to 5 and b is 0 or an integer from 1 to 5; with the proviso that the sum of a and b is not greater than 5.

2. A compound according to claim 1 wherein R is COR$_7$ or SO$_2$R$_8$ where R$_7$ is alkyl having from one to five carbon atoms or trifluoromethyl; R$_1$ hydrogen or alkanoyl having from one to five carbon atoms, R$_5$ is hydrogen or methyl and each of R$_4$ and R$_6$ is hydrogen or alkyl having from one to six carbon atoms.

3. A compound according to claim 2 wherein R$^1$ is hydrogen or acetyl, Z is —(alk$_1$)$_m$—X—(alk$_2$)$_n$— and W is hydrogen or phenyl.

4. A compound according to claim 3 wherein Z is —(alk$_1$)$_m$—O—(alk$_2$)$_n$—.

5. A compound according to claim 4 wherein Z is —O—(alk$_2$)$_n$—, W is phenyl and R$_1$ is acetyl.

6. A compound according to claim 5 wherein Z is

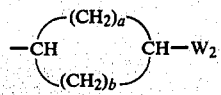

where one of R$_{10}$ and R$_{11}$ is hydrogen and the other is methyl.

7. A trans(6a,10a)diastereomeric compound according to claim 6.

8. A compound according to claim 7 wherein R$_4$ is methyl, R$_5$ is hydrogen and R$_6$ is hydrogen or methyl.

9. A compound according to claim 8 of the formula

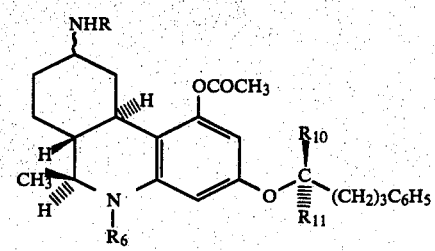

10. A compound according to claim 9 wherein R is CH$_3$CO, CF$_3$CO or CH$_3$SO$_2$.

11. A compound according to claim 10 of the formula

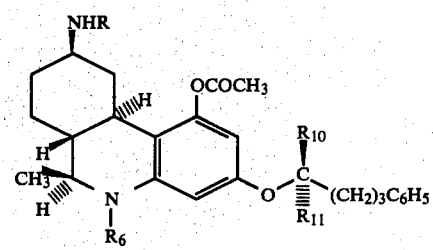

12. A compound according to claim 11 wherein R is CH$_3$SO$_2$ and R$_6$ is hydrogen.

13. A single enantiomer according to claim 11 wherein R$_6$ is methyl, R$_{10}$ is hydrogen and R$_{11}$ is methyl.

14. The compound according to claim 13 wherein R is CH$_3$CO.

15. A compound according to claim 10 of the formula

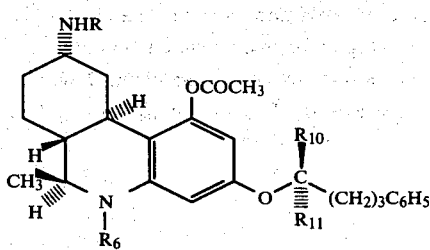

16. A compound according to claim 15 wherein R is $CH_3CO$ and $R_6$ is methyl.

17. A compound according to claim 15 wherein R is $CH_3SO_2$ and $R_6$ is methyl.

18. A compound according to claim 2 wherein Z is alkylene having from one to nine carbon atoms and W is hydrogen or phenyl.

19. A compound according to claim 18 wherein Z is

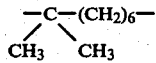

and W is hydrogen.

20. A compound according to claim 18 wherein Z is $-CH(CH_3)(CH_2)_3-$ and W is phenyl.

21. A compound according to claim 1 wherein R is hydrogen.

22. A compound according to claim 21 wherein $R^1$ is hydrogen or alkanoyl having from one to five carbon atoms, $R_5$ is hydrogen or methyl and each of $R_4$ and $R_6$ is hydrogen or alkyl having from one to six carbon atoms.

23. A method for producing analgesia in a mammalian subject in need of such treatment which comprises orally or parenterally administering to said subject an analgesic-producing amount of a compound according to claim 1.

24. A pharmaceutical composition for use as an analgesic which comprises a pharmaceutically-acceptable carrier and an analgesia-producing amount of a compound according to claim 1.

25. A method for prevention and treatment of nausea in a mammal subject to said nausea which comprises orally or parenterally administering to said mammal a compound according to claim 1 in an amount effective to prevent nausea.

26. A pharmaceutical composition for use in prevention and treatment of nausea which comprises a pharmaceutically-acceptable carrier and a compound according to claim 1 in an amount effective to prevent nausea.

* * * * *